(12) United States Patent
Arnold et al.

(10) Patent No.: US 9,322,007 B2
(45) Date of Patent: Apr. 26, 2016

(54) STABLE FUNGAL CEL6 ENZYME VARIANTS

(75) Inventors: Frances H. Arnold, La Canada, CA (US); Indira Wu, Pasadena, CA (US)

(73) Assignee: The California Institute of Technology, Pasadena, CA (US)

( * ) Notice: Subject to any disclaimer, the term of this patent is extended or adjusted under 35 U.S.C. 154(b) by 918 days.

(21) Appl. No.: 13/554,736

(22) Filed: Jul. 20, 2012

(65) Prior Publication Data

US 2015/0259657 A1    Sep. 17, 2015

Related U.S. Application Data

(60) Provisional application No. 61/510,914, filed on Jul. 22, 2011.

(51) Int. Cl.
| | | |
|---|---|---|
| *C12N 9/26* | (2006.01) | |
| *C12N 15/00* | (2006.01) | |
| *C12P 7/00* | (2006.01) | |
| *C07H 21/04* | (2006.01) | |
| *C12N 9/42* | (2006.01) | |
| *C12P 19/14* | (2006.01) | |
| *C12P 7/10* | (2006.01) | |
| *C12P 19/02* | (2006.01) | |

(52) U.S. Cl.
CPC .............. *C12N 9/2437* (2013.01); *C12N 15/00* (2013.01); *C12P 7/00* (2013.01); *C12P 7/10* (2013.01); *C12P 19/02* (2013.01); *C12P 19/14* (2013.01); *C12Y 302/01091* (2013.01); *C12P 2203/00* (2013.01)

(58) Field of Classification Search
CPC ........ C12N 9/2437; C12N 15/09; C12N 7/00; C12P 19/14
See application file for complete search history.

(56) References Cited

U.S. PATENT DOCUMENTS

| | | | |
|---|---|---|---|
| 4,894,338 A | 1/1990 | Knowles et al. | |
| 5,198,346 A | 3/1993 | Ladner et al. | |
| 5,223,409 A | 6/1993 | Ladner et al. | |
| 5,605,793 A | 2/1997 | Stemmer | |
| 5,741,691 A | 4/1998 | Arnold et al. | |
| 5,811,238 A | 9/1998 | Stemmer et al. | |
| 5,830,721 A | 11/1998 | Stemmer et al. | |
| 5,837,458 A | 11/1998 | Minshull et al. | |
| 5,906,930 A | 5/1999 | Arnold et al. | |
| 5,945,325 A | 8/1999 | Arnold et al. | |
| 6,090,604 A | 7/2000 | Golightly et al. | |
| 6,107,073 A | 8/2000 | Chen | |
| 6,316,216 B1 | 11/2001 | Ohto et al. | |
| 6,361,988 B1 | 3/2002 | Arnold et al. | |
| 6,498,026 B2 | 12/2002 | Delagrave et al. | |
| 6,524,837 B1 | 2/2003 | Arnold et al. | |
| 6,537,746 B2 | 3/2003 | Arnold et al. | |
| 6,643,591 B1 | 11/2003 | Korzekwa et al. | |
| 6,794,168 B1 | 9/2004 | Wong et al. | |
| 7,098,010 B1 | 8/2006 | Arnold et al. | |
| 7,115,403 B1 | 10/2006 | Arnold et al. | |
| 7,226,768 B2 | 6/2007 | Farinas et al. | |
| 7,435,570 B2 | 10/2008 | Arnold et al. | |
| 7,465,567 B2 | 12/2008 | Arnold et al. | |
| 7,524,664 B2 | 4/2009 | Arnold et al. | |
| 7,691,616 B2 | 4/2010 | Farinas et al. | |
| 7,867,744 B2 | 1/2011 | Wu et al. | |
| 2001/0051855 A1 | 12/2001 | Wang et al. | |
| 2002/0045175 A1 | 4/2002 | Wang et al. | |
| 2003/0100744 A1 | 5/2003 | Farinas et al. | |
| 2005/0003389 A1 | 1/2005 | Wang et al. | |
| 2005/0037411 A1 | 2/2005 | Arnold et al. | |
| 2005/0059045 A1 | 3/2005 | Arnold et al. | |
| 2005/0059128 A1 | 3/2005 | Arnold et al. | |
| 2005/0202419 A1 | 9/2005 | Cirino et al. | |
| 2008/0057577 A1 | 3/2008 | Arnold et al. | |
| 2008/0248545 A1 | 10/2008 | Arnold et al. | |
| 2008/0268517 A1 | 10/2008 | Arnold et al. | |
| 2008/0293928 A1 | 11/2008 | Farinas et al. | |
| 2009/0124515 A1 | 5/2009 | Arnold et al. | |
| 2009/0142821 A1 | 6/2009 | Cirino et al. | |
| 2009/0264311 A1 | 10/2009 | Arnold et al. | |
| 2009/0298148 A1 | 12/2009 | Arnold et al. | |
| 2010/0255542 A1* | 10/2010 | Arnold et al. ................... 435/72 |
| 2010/0304464 A1* | 12/2010 | Arnold et al. ................. 435/209 |

FOREIGN PATENT DOCUMENTS

| | | |
|---|---|---|
| EP | 0752008 | 1/1997 |
| WO | 95/22625 | 8/1995 |
| WO | 97/16553 | 5/1997 |
| WO | 97/20078 | 6/1997 |
| WO | 97/35957 | 10/1997 |
| WO | 97/35966 | 10/1997 |
| WO | 98/27230 | 6/1998 |

(Continued)

OTHER PUBLICATIONS

Moriya et al. Cloning and overexpression of the avi2 gene encoding a major cellulase produced by Humicola insolens FERM BP-5977. Biosci. Biotechnol. Biochem. 67:1434-1437(2003).*

Kim, Nam Kyung, International Search Report and Written Opinion, PCT Application No. PCT/US2012/047637, Korean Patent Office, Mar. 28, 2013.

Heinzelman, P. et al., "A family of thermostable fungal cellulases created by structure-guided recombination," Apr. 7, 2009, vol. 106, No. 14, pp. 5610-5615.

Abecassis et al., "High efficiency family shuffling based on multi-step PCR and in vivo DNA recombination in yeast: statistical functional analysis of a combinatorial library between human cytochrome 1A1 and 1A2," Nucleic Acids Res., 2000, vol. 28, E88.

Abecassis et al., "Design and characterization of a novel family-shuffling technology adapted to membrane enzyme: application to P450s involved in xenobiotic metabolism," adv. Exp. Med. Biol. 500, 2001, pp. 319-322.

Abecassis et al., "Exploration of natural and artificial sequence spaces: Towards a functional remodeling of membrane-bound cytochome P450," Biocatal. Biotransform, 2003, vol. 21, No. 2, pp. 55-66.

(Continued)

*Primary Examiner* — Yong Pak

(74) *Attorney, Agent, or Firm* — Joseph R. Baker, Jr.; Gavrilovich, Dodd & Lindsey LLP

(57) ABSTRACT

The disclosure provides variant Cel6a enzymes having increased thermostability, methods of making and using such polypeptides.

11 Claims, 8 Drawing Sheets

(56) References Cited

FOREIGN PATENT DOCUMENTS

| WO | 98/31837 | 7/1998 |
|---|---|---|
| WO | 98/41653 | 9/1998 |
| WO | 98/42832 | 10/1998 |
| WO | 00/00632 | 1/2000 |
| WO | 00/04190 | 1/2000 |
| WO | 00/06718 | 2/2000 |
| WO | 00/09679 | 2/2000 |
| WO | 00/18906 | 4/2000 |
| WO | 00/31273 | 6/2000 |
| WO | 00/42560 | 7/2000 |
| WO | 01/61344 | 8/2001 |
| WO | 01/62938 | 8/2001 |
| WO | 02/083868 | 10/2002 |
| WO | 03/008563 | 1/2003 |
| WO | 03/091835 | 11/2003 |
| WO | 2005/017105 | 2/2005 |
| WO | 2005/017106 | 2/2005 |
| WO | 2006/105082 | 10/2006 |
| WO | 2008/085900 | 7/2008 |
| WO | 2008/098198 | 8/2008 |
| WO | 2008/115844 | 9/2008 |
| WO | 2008/118545 | 10/2008 |
| WO | 2008/121435 | 10/2008 |
| WO | 2010/066411 A2 | 6/2010 |

OTHER PUBLICATIONS

Abkevich et al., "Impact of Local and Non-Local interactions on Thermodynamics and Kinetics of Protein Folding", J. Mol. Biol. 1995, 252, pp. 460-471.
Affholter et al., "Engineering a Revolution", Chembytes e-zine, Apr. 1999, [Website] 10 pages, printed Apr. 14, 2004, http://www.chemsoc.org/chembytes/ezine/1999/arnold_apr99.htm.
Anfinsen, "Principles that Govern the Folding of Protein Chains," Science, Jul. 20, 1973, pp. 223-230, vol. 181, No. 4096, American Asso for the Advancement of Science, Washington, DC, USA.
Appel et al., "A P450 BM-3 mutant hydroxylates alkanes, cycloalkanes, arenas and heteroarenes," Journal of Biotechnology, 2001, pp. 167-171, Elsevier Science B.V.
Arkin et al., "An algorithm for protein engine ring: Simulations of recursive ensemble mutagenesis," Proc. Natl. Acad. Sci.-USA, Aug. 1992, pp. 7811-7815, vol. 89, Applied Biological Sciences.
Arnold, "Engineering proteins for nonnatural environments," The FASEB Journal, Jun. 1993, pp. 744-749, vol. 7, No. 6, FASEB, Bethesda, MD, USA.
Arnold, Frances H., "Design by Directed Evolution," Accounts of Chemical Research, 1998, vol. 31, pp. 125-131.
Arnold et al., "Directed Evolution of Biocatalysts," Current Opinion in Chem. Biology, Current Biology Ltd, London GB 3(1):54-59, Feb. 1999.
Arnold et al., "Optimizing Industrial Enzymes by Directed Evolution," Advances in Biochemical Engineering/Biotechnology, 1997, pp. 1-14, vol. 58, Springer-Verlag, Berlin, Germany.
Arnold, "Advances in Protein Chemistry", Adv. Protein Chem., 2000, 55: ix-xi.
Arnold, "Combinatorial and Computational Challenges for Biocatalyst design", Nature, 2001, 409(6817), pp. 253-257.
Arnold & Wintrode, Enzymes, Directed Evolution, in Encyclopedia of bioprocess technology: fermentation, biocatalysis, and bioseparation, 1999, 2, 971.
Aust, S. D., "Commentary—Laboratory evolution of peroxide-mediated cytochrome P450 Hydroxylation," Redox Report, 1999, 4:195-7.
Bell et al., "Butane and propane oxidation by engineered cytochromes P450(cam)," Chemical Communications, 2002, vol. 5, pp. 490-491.
Bell et al., "Engineering Cytochrome P450cam into an alkane hydroxylase," Dalton Transactions, 2003, vol. 11, pp. 2133-2140.
Beratan, D. N.T., "The protein bridge between redox centres," Protein Electron Transfer, 1996, Oxford: Bios Scientific Publishers, pp. 23-42.
Berman et al., "The Protein Data Bank", Nucl. Acids Res., 2000, 28, pp. 235-242.
Better et al., "*Escherichia coli* Secretion of an Active Chimeric Antibody Fragment," Science, May 20, 1988, pp. 1041-1043, vol. 240, American Asso for the Advancement of Science, Washington, DC, USA.
Boder, et al., "Directed Evolution of Antibody Fragments with Monovalent Femtomolar Antigen-binding affinity", Proc Natl. Acad. Sci. USA, 2000 97(20), pp. 10701-10705.
Bogarad et al., "A hierarchical approach to protein molecular evolution," Proc. Natl. Acad. Sci USA, 1999,vol. 96, pp. 2591-2595.
Bohm, "New approaches in molecular structure prediction", Biophys Chem., 1996, 59, pp. 1-32.
Branden et al., "Introduction to protein structure," 1991, pp. 247, Garland Publishing Inc., New York.
Brenner, et al., "A quantitative methodology for the de novo design of proteins," Protein Science, vol. 3, pp. 1871-1882, 1994.
Brooks B.R. et al., "CHARMM: A Program for Macromolecular Energy, Minimization, and Dynamics Calculations", J. Comp. Chem., 1983, 4, pp. 187-217.
Campbell et al., "Chimeric proteins can exceed the sum of their parts: Implication for evolution and protein design," Nat. Biotechnol., May 1997, vol. 15, pp. 439-443.
Carmichael, A. et al., "Protein engineering of Bacillus megaterium CYP102," Eur. J. Biochem., 2001, pp. 3117-3125, vol. 268, FEBS.
Chang, C. et al., "Evolution of a cytokine using DNA family shuffling," Nature Biotechnology, Aug. 1999, pp. 793-797, vol. 17.
Chang, Yan-Tyang et al., "Homology Modeling, Molecular Dynamics Simulations, and Analysis of CYP119, a P450 Enzyme from Extreme Acidothermophilic Archaeon Sulfolobus solfataricus," Biochemistry, 2000, 39, pp. 2484-2498.
Chen, K. et al., "Tuning the activity of an enzyme for unusual environments: Sequential random mutagenesis of subtilisin E for catalysis in dimethylformamide," Proc. Natl. Acad. Sci. USA, Jun. 15, 1993, pp. 5618-5622, vol. 90, No. 12.
Christians, F. et al., "Directed evolution of thymidine kinase for AZT phosphorylation using DNA family shuffling," Nature Biotechnology, Mar. 1999, pp. 259-264, vol. 17, Nature America Inc., New York, NY, USA.
Cirino et al. "A self-sufficient peroxide-driven hydroxylation biocatalyst," Angewandte Chemie International Edition, 2003, vol. 42, No. 28, pp. 3299-3301.
Cirino et al., "Exploring the diversity of heme enzymes through directed evolution," In Directed Molecular Evolution of Proteins, 2002, pp. 215-243, S. Brakmann and K. Johnsson, eds., (Germany: Wiley-VCH).
Cirino, Patrick C., and R. Georgescu "Screening for Thermostability," Methods in Molecular Biology, May 2003, pp. 117-125, vol. 230.
Cirino & Arnold, "Protein engineering of oxygenases for biocatalysts", Current Opinion in Chemical Biology, 2002, vol. 6, pp. 130-135.
Cirino & Arnold, "Regioselectivity and Activity of Cytochrome P450 BM-3 and Mutant F87A in Reactions Driven by Hydrogen Peroxide", Adv. Synth. Catal., 2002, vol. 344, No. 9, pp. 932-937.
Cleland, J. et al., "Cosolvent Assisted Protein Refolding," Biotechnology, Dec. 1990, pp. 1274-1278, vol. 8.
Coco et al., "DNA shuffling method for generating highly recombined genes and evolved enzymes," Nat. Biotechnol., 2001, vol. 19, pp. 354-359.
Cornell et al., "A Second Generation Force Field for the Simulation of Proteins, Nucleic Acids, and Organic Molecules", J. Amer. Chem. Soc., 1995, 117, pp. 5179-5197.
Crameri, A. et al., "Molecular evolution of an arsenate detoxification pathway by DNA shuffling," Nature Biotechnology, May 1997, pp. 436-438, vol. 15, Nature America Inc., New York, NY, USA.
Crameri, A. et al., "Improved Green Fluorescent Protein by Molecular Evolution Using DNA Shuffling," Nature Biotechnology, Mar. 1996, pp. 315-319, vol. 14, Nature America Inc., New York, NY, USA.
Crameri, A. et al., "Construction and evolution of antibody-phage libraries by DNA shuffling," Nature Medicine, Jan. 1996, pp. 100-106, vol. 2, No. 1.

(56) References Cited

OTHER PUBLICATIONS

Crameri et al., "DNA shuffling of a family of genes from diverse species accelerates directed evolution," Nature, 1998, vol. 391, pp. 288-291.
Cui et al., "Recombinatoric exploration of novel folded structures: a heteropolymer-based model of protein evolutionary landscapes," Proc Natl Acad Sci USA, 2002, vol. 99, pp. 809-814.
Dahiyat et al., "Protein design automation", Protein Science, vol. 5, pp. 895-903, 1996.
Dahiyat et al. "De Novo Protein Design: Fully Automated Sequence Selection", Science, 1997, vol. 278, pp. 82-87.
Dahiyat, et al., "Probing the Role of packing specifically in protein design", Proc. Natl. Acad. Sci. USA, 1997, 94, pp. 10172-10177.
Dahiyat, et al., "Automated design of the surface positions of protein helices", Protein Science, 1997, 6, pp. 1333-1337.
De Maeyer et al., "All in one: a highly detailed roamer library improves both accuracy and speed in the modeling of sidechains by dead-end elimination", Folding & Design, 1997, 2, pp. 53-66.
De Visser et al., "Hydrogen bonding modulates the slectivity of enzymatic oxidation by P450: Chameleon oxidant behavior by compound I," Angewandte Chemie-International Edition, 2002, vol. 41, No. 11, pp. 1947.
De Visser et al., "What factors affect the regioselectivity of oxidation by cytochrome P450? A DFT study of allylic hydroxylation and double bond epoxidation in a model reaction," Journal of the American Chemical Society, 2002, vol. 124, No. 39, pp. 11809-11826.
Delagrave, S. et al., "Recursive ensemble mutagenesis," Protein Engineering, Apr. 1993, pp. 327-331, vol. 6, No. 3, Oxford University Press.
Delagrave, S. et al., "Searching Sequence Space to Engineer Proteins: Exponential Ensemble Mutagenesis," Bio/Technology, Dec. 1993, pp. 1548-1552, vol. 11, American Society for Cell Biology, New Orleans, LA, USA.
Desjarlais & Clarke N.D., "Computer search algorithms in protein modification and design", Curr. Opin. Struct. Biol., 1998, 8, pp. 471-475.
Desmet J., et al., 1994, in the Protein Folding Problem and Tertiary Structure Prediction (Jr., K.M. & Grand, S.L., eds.) pp. 307-337 (Birkhauser, Boston).
Desmet J., et al., 1992, "The dead-end elimination theorem and its use in protein side-chain positioning", Nature, 356, pp. 539-542.
Dordick, J., "Designing Enzymes for Use in Organic Solvents," Biotechnol. Prog., 1992, pp. 259-267, 8, American Chemical Society and American Institute of Chemical Engineers.
Dube et al., "Selection of new biologically active molecules from random nucleotide sequences", Gene, 1993, 137, pp. 41-47.
Dunbrack & Karplus, "Backbone-dependent Rotamer Library for Proteins Application to Sidechain prediction", J. Mol. Biol., 1993, 230, pp. 543-574.
Dunbrack & Karplus, "Conformational analysis of the backbone-dependent roamer preferences of protein sidechains", Nature Struct. Biol., 1994, 1, pp. 334-340.
Eisenberg et al., "Solvation Energy in Protein Folding and Binding", Nature, 319, 1986, pp. 199-203.
Eisenhaber et al., "Prediction of secondary structural content of proteins from their amino acid composition alone 2. The paradox with secondary structural class", Proteins, 24, 1996, pp. 169-179.
Eisenhaber et al., "Protein-structure prediction—recognition of primary, secondary, and tertiary structural features from amino-acid-sequence", Crit Rev Biochem Mol., 1995, 30, pp. 1-94.
Farinas, E., et al., "Directed Evolution of a Cytochrome P450 Monooxygenase for Alkane Oxidation," Adv. Synth. Catal., 2001, pp. 601-606, vol. 343, No. 6-7.
Fontana et al., "Continuity in Evolution: On the Nature of Transitions", Science, 1998, 280, pp. 1451-1455.
Foume et al., "Better structures from better data through better methods: a review of developments in de novo macromolecular phasing techniques and associated instrumentation at LURE", J. Synchrotron Radiat., 1999, 6, pp. 834-844.

Fruetel, J., et al., "Relationship of Active Site Topology to Substrate Specificity for Cytochrome P450terp (CYP108)," The Journal of Biological Chemistry, Nov. 18, 1994, pp. 28815-28821, vol. 269, No. 46, The American Society for Biochemistry and Molecular Biology, Inc.
Gardner et al., "The use of H-2, C-13, N-15, multidimensional NMR to study the structure and dynamics of proteins", Annu. Rev. Bioph. Biom., 1998, 27, pp. 357-406.
Gazaryan, I. G., "Heterologous Expressions of Heme Containing Peroxidases," Plant Peroxidase Newsletter, Sep. 1994, pp. 11-13, No. 4, LABPV Newsletters.
Gibbs et al., "Degenerate oligonucleotide gene shuffling (DOGS): a method for enhancing the frequency of recombination with family shuffling," Gene, 2001, vol. 271, pp. 13-20.
Goldstein R.F., 1994, "Efficient rotamer elimination applied to protein side-chains and related spin glasses", Biophysical Journal, 66, pp. 1335-1340.
Giver, L., et al., "Combinatorial Protein Design by In Vitro Recombination," Current Opinion in Chemical Biology, 1998, pp. 335-338, vol. 2, Current Biology Ltd.
Gleider et al., "Laboratory evolution of a soluble, self-sufficient, highly active alkane hydroxylase," Nature Biotech., 2002, vol. 20, pp. 1135-1139.
Glieder et al., "Laboratory evolution of a soluble, self-sufficient, highly active alkane hydroxylase," Nature Biotech., 2002, vol. 20, pp. 1-5.
Godzik, "In search of the ideal protein sequence", Protein Engineering, 1995, 8, pp. 409-416.
Goldman, E., et al., "An Algorithmically Optimized Combinatorial Library Screened by Digital Imaging Spectroscopy," Biotechnology, Dec. 1992, pp. 1557-1561, vol. 10.
Gonzalez et al., "Evolution of the P450 gene superfamily animal-plant 'warfare', molecular drive and human genetic differences in drug oxidation," Trends Genet. 1990, vol. 6, pp. 182-186.
Gordon & Mayo, "Energy functions for protein design", Curr Opin. Struct. Biol., 1999, 9(4), pp. 509-514.
Gordon, "Radical Performance Enhancements for Combinatorial Optimization Algorithms Based on the Dead-End Elimination Theorem" Journal of Computational Chemistry, 1998, 19(13), pp. 1505-1514.
Gotoh, Cytochrome P450, 2nd Edition, 1993, pp. 255-272.
Govindaraj and Poulos; "Role of the linker region connecting the reductase and heme domains in cytochrome P450BM-3"; Biochemistry; vol. 34, No. 35, Abstract, 1995.
Govindaraj and Poulos; "Role of the linker region connecting the reductase and heme domains in cytochrome P450BM-3"; Biochemistry; vol. 34, No. 35, 1995, pp. 11221-11226.
Graham-Lorence, S., et al., "An Active Site Substitution, F87V, Converts Cytochrome P450 BM-3 into a Regio-and Stereoselective (14S,15R)-Arachidonic Acid Epoxygenase," The Journal of Biological Chemistry, Jan. 10, 1997, pp. 1127-1135, vol. 272, No. 2, The American Society for Biochemistry and Molecular Biology, Inc.
Green, J., et al., "Substrate Specificity of Soluble Methane Monooxygenase Mechanistic Implications," The Journal of Biological Chemistry, Oct. 25, 1989, pp. 17698-17703, vol. 264, No. 30, The American Society for Biochemistry and Molecular Biology, Inc.
Groves, John et al., "Models and Mechanisms of Cytochrome P450 Action," Cytochrome P450: Structure, Mechanisms, and Biochemistry, 2nd Edition, New York, 1995, pp. 3-48.
Guengerich, F., et al., "Purification of Functional Recombinant P450s from Bacteria," Methods in Enzymology, 1996, pp. 35-44, vol. 272, Academic Press, Inc.
Haines, Donovan C. et al., "Pivotal Role of Water in the Mechanism of P450BM-3," Biochemistry, 2001, 40, pp. 13456-13465.
Hansson et al., "Evolution of differential substrate specificities in Mu class glutathione transferases probed by DNA shuffling," J. Mol. Biol., 1999, vol. 287, pp. 265-276.
Hendsch et al., "Do salt bridges stabilize proteins—a continuum electrostatic analysis", Protein Science, 1994, 3, pp. 211-226.
Hermes, J., et al., "Searching Sequence Space by Definably Random Mutagenesis: Improving the Catalytic Potency of an Enzyme," Proc. Natl. Acad. Sci. USA, Jan. 1990, pp. 696-700, vol. 87.

(56) References Cited

OTHER PUBLICATIONS

Hiraga et al., "General method for sequence-independent site-directed chimeragenesis," J. Mol. Biol. 2003, vol. 330, pp. 287-296.
Horton, et al., "Engineering hybrid genes with the use of restriction enzymes: gene splicing by overlap extention," Gene, 1989, vol. 77, pp. 61-68.
Ishima R. et al., "Protein Dynamics from NMR", Nat Struct. Biol, 2000, 7, pp. 740-743.
Jaeger et al., "Enantioselective biocatalysts optimized by directed evolution," Current Opinion in Biotechnology, 2004, vol. 15, No. 4, pp. 305-313.
Goomber et al., Enhancing thermostability of the biocatalysts beyond their natural function via protein engineering, International Journal for Biotechnology and Molecular Biology Research, (2012), vol. 3(3), pp. 24-29.
Buske et al., In silico characterization of protein chimeras: Relating sequence and function within the same fold, Proteins (2009), vol. 77, Issue 1, pp. 111-120.
Multiple Sequence Alignment (MSA) (last viewed on May 9, 2012).
Guo et al., Protein tolerance to random amino acid change, 2004, Proc. Natl. Acad. Sci. USA 101: 9205-9210.
Lazar et al., Transforming Growth Factor a: Mutation of Aspartic Acid 47 and Leucine 48 Results in Different Biological Activity,1988, Mol. Cell. Biol. 8:1247-1252.
Hill et al., Functional Analysis of conserved Histidines in ADP-Glucose Pyrophosphorylase from *Escherichia coli*, 1998, Biochem. Biophys. Res. Comm. 244:573-577.
Wacey et al., Disentangling the perturbational effects of amino acid substitutions in the DNA-binding domain of p53., Hum Genet, 1999, vol. 104, pp. 15-22.
Weber, Overview of Crystallization Methods. Methods in Enzymology, 1997, vol. 276, pp. 13-22.
Drenth, "Principles of Protein X-Ray Crystallography", 2nd Edition, 1999, Springer-Verlag New York Inc., pp. 1-21.
Klyushnichenko, Protein crystallization: From HTS to kilogram-scale, Curro Op. Drug Discovery, 2003, vol. 6(6), pp. 848-854.
Yang et al., Crystalline monoclonal antibodies for subcutaneous delivery, PNAS Jun. 10, 2003, vol. 100, pp. 6934-6939.
Bloom et al., Evolving strategies for enzyme engineering., Current Opinion in Structural Biology, 2005, vol. 15, pp. 447-452.
Shao, Z., et al., "Random-priming In Vitro Recombination: An Effective Tool for Directed Evolution," Nucleic Acids Research, Jan. 15, 1998, pp. 681-683, vol. 26, No. 2, Oxford University Press.
Sidelar et al., "Effects of salt bridges on protein structure and design", Protein Science, 1998, 7, pp. 1898-1914.
Sieber et al., "Libraries of hybrid proteins form distantly related sequences," Nat. Biotechnol., 2001, vol. 19, pp. 456-460.
Sirotkin, K., Advantages to Mutagenesis Techniques Generating Populations Containing the Complete Spectrum of single Codon Changes, J. Theor Biol., 1986, pp. 261-279, vol. 123, Academic Press Inc. (London) Ltd.
Skandalis, et al., "Creating novel enzymes by applied molecular evolution", Chem. Biol., 1997, 4, pp. 889-898.
Smith, A., et al., "Substrate Binding and Catalysis in Heme Peroxidases," Current Opinion in Chemical Biology, (1998), pp. 269-278, vol. 2.
Smith et al., "Current limitations to protein threading approaches", J. Comput. Biol., 1997, 4, pp. 217-225.
Sono et al., "Heme-containing oxygenases," Chemical Reviews, 1996, vol. 96, No. 7, pp. 2841-2887.
Staijen, I., et al., "Expression, Stability and Performance of the Three-Component Alkane Mono-oxygenase of Pseudomonas oleovorans in *Escherichia coli*," Eur. J. Biochem., 2000, pp. 1957-1965, vol. 267.
Stemmer, W., "DNA Shuffling by Random Fragmentation and Reassembly: In Vitro Recombination for Molecular Evolution," Proc. Natl. Acad. Sci. USA, Oct. 25, 1994, pp. 10747-10751, vol. 91, No. 22.
Stemmer, W., "Rapid Evolution of a Protein In Vitro by DNA Shuffling," Nature, Aug. 4, 1994, pp. 389-391, vol. 370, No. 6488.
Stemmer, W., et al., "Selection of an Active Single Chain Fv Antibody from a Protein Linker Library Prepared by Enzymatic Inverse PCR," BioTechniques, 1993, pp. 256-265, vol. 14, No. 2.
Stevenson, J., et al., "The Catalytic Oxidation of Linear and Branched Alkanes by Cytochrome P450cam," J. Am. Chem. Soc., 1996, pp. 12846-12847, vol. 118, No. 50, American Chemical Society.
Stevenson et al., "Engineering molecular recognition in alkane oxidation catalysed by cytochrome P450(cam)", New Journal of Chemistry, 1998, vol. 22, No. 6, pp. 551-552.
Stikoff et al., "Calculation of electrostatic effects at the amino-terminus of an alpha-helix", Biophys. J., 1994, 67, pp. 2251-2260.
Street & Mayo, "Computational protein design", Structure, 1999, 7(5), pp. R105-R109.
Street et al., "Pairwise Calculation of Protein Solvent-Accessible Surface Areas", Folding & Design, 1998, 3, pp. 253-258.
Swindells et al., "Structure prediction and modeling", Curr. Opin. Biotech., 1991, 2, pp. 512-519.
Taly et al., "A combinatorial approach to substrate discrimination in the P450 CYP1A subfamily," Biochimica et Biophysica Acta, 2007, vol. 1770, pp. 446-457.
Thatcher, D., et al., "Protein Folding in Biotechnology," Mechanisms of Protein Folding, 1994, pp. 229-261, IRL Press, Oxford.
Tsotsou et al., "High throughput assay for chytochroms P450BM3 for screening libraries of substrates and combinatorial mutants," Biosensors and Bioelectronics, 2002, vol. 17, No. 1-2, pp. 119-131.
Urlacher et al., "Biotransformations using prokaryotic P450 monooxygenases," Current Opinion in Biotechnology, 2002, vol. 13, pp. 557-564.
Urlacher et al., "Protein Engineering of cytochrome P450 monooxygenase from Bacillus megaterium." Methods in Enzymology, pp. 208-224, vol. 388, 2004.
Vidakovic, Momcilo et al., "Understanding the role of the essential Asp251 in cytochrome P450cam using site-directed mutagenesis, crystallography, and kinetic solvent isotope effect", Biochemistry, vol. 37, No. 26, Jun. 30, 1998, pp. 9211-9219, XP002187779.
Voight et al., "Protein building blocks preserved by recombination," Nat. Struct. Biol., 2002, vol. 9, pp. 553-558.
Volkov et al., "Recombination and chimeragenesis by in vitro heteroduplex formation and in vivo repair," Nucleic Acids Res., 1999, vol. 27, e18.
Wang et al., "MMDB: 3D structure date in Entrez", Nucl. Acids Res., 2000, 28, pp. 243-245.
Weiner et al., "A new force field for molecular mechanical simulation of nucleic acids and proteins", J. Amer. Chem. Soc., 1984, 106, pp. 765-784.
Weiner et al., "An all atom force field for simulations of proteins and nucleic acids", J. Comp. Chem., 1986, 7, pp. 230-252.
Wesson et al., "Atomic salvation parameters applied to molecular dynamics of proteins in solution", Protein Science, 1992, 1, pp. 227-235.
Wilson, et al., "Modeling Side-chain Conformation for Homologous Proteins Using an Energy-based Rotomer Search", J. Mol. Biol., 1993, 229, pp. 996-1006.
Xia et al., "Ab initio construction of protein tertiary structures using a hierarchical approach", J. Mol. Biol., 2000, 300, pp. 171-185.
Yeom, H., et al., "Oxygen Activation by Cytochrome P450BM-3: Effects of Mutating an Active Site Acidic Residue," Archieves of Biochemistry and Biophysics, Jan. 15, 1997, pp. 209-216, vol. 337, No. 2, Academic Press.
Yeom, Sligar H., et al., "The role of Thr268 in oxygen activation of cytochrome P450BM-3" Biochemistry, vol. 34, No. 45., Abstract 1995.
Zhang, J., et al., "Directed Evolution of a Fucosidase from a Galactosidase by DNA Shuffling and Screening," Proc. Natl. Acad. Sci. USA, Apr. 1997, pp. 4504-4509, vol. 94.
Zhao, H., et al., "Directed Evolution Converts Subtilisin E into a Functional Equivalent of Thermitase," Protein Engineering, 1999, pp. 47-53, vol. 12, No. 1, Oxford University Press.
Zhao, H. et al., "Functional and nonfunctional mutations distinguished by random recombination of homologous genes," Proc. Natl. Acad. Sci. USA, 1997, vol. 94, pp. 7997-8000.

(56) References Cited

OTHER PUBLICATIONS

Zhao, H. et al., "Molecular Evolution by Staggered Extension Process (StEP) In Vitro Recombination," Nature Biotechnology, Mar. 1998, pp. 258-261, vol. 16.
Zhao, H., et al., "Optimization of DNA Shuffling for High Fidelity Recombination," Nucleic Acids Research, 1997, pp. 1307-1308, vol. 25, No. 6, Oxford University Press.
Zhao, H. et al., "Methods for Optimizing Industrial Enzymes by Directed Evolution", Manual of Industrial Microbiology and Biotechnology, 2nd Edition, 1999, pp. 597-604.
Zimmer, T., et al., "The CYP52 Multigene Family of Candida maltosa Encodes Functionally Diverse n-Alkane-Inducible Cytochromes P450," Biochemical and Biophysical Research Communications, 1996, pp. 784-789, vol. 224, No. 3, Academic Press, Inc.
"Enzymology of cytochrme P450 reductase," printed Apr. 5, 2004 http://www/uky.edu/Pharmacy/ps/porter/CPR_enzymology.htm.
"Superfamily name: Cytochrome P450", From the Cytochrome P450 Webpage, printed Apr. 5, 2004, http://drnelson.uthsc.edu/PIR.P450.description.html, 2 pages.
Robert F. Service, "Tapping DNA for structures produces a trickle," News Focus, Science, Nov. 1, 2002, vol. 298, pp. 948-950.
Achutamarthy, Ponnathapu, International Search Report, Date of Mailing of Search: Sep. 25, 2007, International Application No. PCT/US04/18832.
Baharlou, Simin, International Preliminary Report on Patentability, Date of Issuance of Report: Nov. 27, 2008, International Application No. PCT/US06/11273.
Baharlou, Simin, International Preliminary Report on Patentability, Date of Issuance of Report: Aug. 11, 2009, International Application No. PCT/US08/53472.
Baharlou, Simin, International Preliminary Report on Patentability, Date of Issuance of Report: Sep. 22, 2009, International Application No. PCT/US08/057174.
Becamel, Philippe, International Preliminary Report on Patentability and Written Opinion, Date of Issuance of Report: Aug. 4, 2009, International Application No. PCT/US08/52795.
Brusca, John S., International Preliminary Examination Report, Date of Completion of Report: Aug. 7, 2002, International Application N. PCT/US01/05043.
Cook, Gareth, Australian Patent Office Search Report and Written Opinion, Application No. SG200708978-2, Date of Mailing : Dec. 16, 2008.
Cussac, Yolaine, International Preliminary Report on Patentability and Written Opinion, Date of Issuance of Report: Oct. 9, 2007 International Application No. PCT/US04/18832.
Griesinger, Irina, Supplementary European Search Report, Date of Completion of Search: Feb. 25, 2010, Application No. EP08705479.
Lundglen, Jeffrey S. International Search Report, Date of Mailing of Search: Jul. 16, 2001, International Application No. PCT/US01/05043.
Ly, Cheyrie D., International Search Report, Date of Mailing of Search: Aug. 18, 2004, International Application No. PCT/US02/34342.
Meah, Mohammad Y., International Search Report and Written Opinion, Date of Mailing: Sep. 10, 2008, International Application No. PCT/US06/11273.
Nashed, Nashaat, Transmittal of International Search Report and Written Opinion, International Search Report, and Written Opinion, PCT/US08/00135, Sep. 3, 2008.
Nashed, Nashaat, International Search Report and Written Opinion, Date of Mailing of Report: Sep. 26, 2008, International Application No. PCT/US08/53472.
Nickitas-Etienne, Athina, International Preliminary Report on Patentability and Written Opinion, Date of Issuance of Report: Jul. 7, 2009, International Application No. PCT/US08100135.
Nickitas-Etienne, Athina, International Preliminary Report on Patentability and Written Opinion, Date of Issuance of Report: Nov. 17, 2009, International Application No. PCT/US08/53344.
Sonnenschmidt-Rogge, Sandra, International Search Report and Written Opinion, Date of Mailing of Search: Mar. 19, 2009, International Application No. PCT/US08/057174.
Sprinks, Matthew, Supplementary European Search Report, Date of Completion of Search: Oct. 13, 2009, Application No. EP 06748800.
Young, Lee W., International Search Report and Written Opinion, Date of Mailing of Search: Feb. 11, 2009, International Application No. PCT/US08/52795.
Young, Lee W., International Search Report and Written Opinion, Date of Mailing of Search: Apr. 17, 2009, International Application No. PCT/US08/53344.
Cherry, J. et al., "Directed evolution of a fungal peroxidase," Nature Biotechnology, Apr. 1999, pp. 379-384, vol. 17, Nature America Inc., New York, NY, USA.
Dayie KT et al., "Theory and practice of nuclear spin relaxation in proteins", Annu Rev Phys Chem, 1996, 47, pp. 243-282.
Flickinger, et al., "Enzymes, Directed Evolution", in 2 Encyclopedia of Bioprocess Technology: Fermentation, Biocatalysts, and Bioseparation, 1999, 2, pp. 971-987.
Giver, L., et al., "Directed Evolution of a Thermostable Esterase," Proc. Natl. Acad. Sci. USA, Oct. 1998, pp. 12809-12813, vol. 95.
Gram, H., et al., "In Vitro Selection and Affinity Maturation of Antibodies from a Naive Combinatorial Immunoglobulin Library," Proc. Natl. Acad. Sci. USA, Apr. 1992, pp. 3576-3580, vol. 89.
Ito, N. et al., "Crystal Structure of a Free Radical Enzyme, Galactose Oxidase," Journal of Molecular Biology, 1994, pp. 794-814, vol. 238, No. 5, Academic Press Limited.
Ito, N. et al., "X-Ray Crystallographic Studies of Cofactors in Galactose Oxidase," Methods in Enzymology, Redox-Active Amino Acids in Biology, 1995, pp. 235-262, vol. 258, Academic Press, Inc.
Ito, N. et al., "Novel thioether bond revealed by a 1.7 Å crystal structure of galactose oxidase," Nature, Mar. 7, 1991, pp. 87-90.
Jackson et al., "Effect of Cavity-Creating Mutations in the Hydrophobic Core of Chymotrypsin Inhibitor 2", Biochemistry, 1993, 32, pp. 11259-11269.
Kumamaru et al., "Enhanced degradation of polychlorinated biphenyls by directed evolution of biphenyl dioxygenase", Nat. Biotechnol., 1998, vol. 16, pp. 663-666.
Meinhold, P. et al., "Direct Conversion of Ethane to Ethanol by Engineered Cytochrome P450 BM3," ChemBioChem, 2005, pp. 1-4, vol. 6, Wiley-VCH Verlag GmbH & Co. Weinheim, Germany.
Moore, J. et al., "Directed evolution of a para-nitrobenzyl esterase for aqueous-organic solvents," Nature Biotechnology, Apr. 1996, pp. 458-467, vol. 14.
Moser, Christopher, et al., "Biological Electron Transfer," Journal of Bioenergetics and Biomembranes, vol. 27, No. 3, 1995, pp. 263-274.
Nagayama, Y. et al., "Role of Asparagine-linked Oligosaccharides in Protein Folding, Membrane Targeting, and Thyrotropin and Autoantibody Binding of the Human Thyrotropin Receptor," Journal of Biological Chemistry, Dec. 1998, pp. 33423-33428, vol. 273, No. 5, The American Society for Biochemistry and Molecular Biology, Inc.
Nikolova, et al., "Semirational design of active tumor suppressor p53 DNA binding domain with enhanced stability", Proc. Natl. Acad. Sci, USA, 1998, 95, pp. 14675-14680.
Schmid, A., et al., "Industrial Biocatalysis Today and Tomorrow," Nature, Jan. 11, 2001, pp. 258-268, vol. 409, Macmillian Magazines Ltd.
Sun, L., et al., "Expression and Stabilization of Galactose Oxidase in *Escherichia coli* by Directed Evolution," Protein Engineering, Sep. 2001, pp. 699-704, vol. 14, No. 9, Oxford University Press.
Sun, L., et al., "Modification of Galactose Oxidase to Introduce Glucose 6-Oxidase Activity," ChemBioChem: A European Journal of Chemical Biology, Aug. 2, 2002, pp. 781-783, vol. 3, No. 8, Wiley-VCH-Vertag GmbH, Weinheim, Germany.
Tams, J., et al., "Glycosylation and Thermodynamic Versus Kinetic Stability of Horseradish Peroxidase," FEBS Letters, 1998, pp. 234-236, vol. 421, Federation of European Biochemical Societies.
Wan et al., "In vitro evolution of horse heart myoglobin to increase peroxidase activity," PNAS USA, 95 (22):12825-12831, Oct. 27, 1998.
Wilkinson, D., et al., "Structural and Kinetic Studies of a Series of Mutants of Galactose Oxidase Identified by Directed Evolution,"

(56) References Cited

OTHER PUBLICATIONS

Protein Engineering, Design & Selection, Jan. 12, 2004, pp. 141-148, vol. 17, No. 2, Oxford University Press.
Woods et al., "Molecular Mechanical and Molecular Dynamic Simulations of Glycoproteins and Oligosaccharides. 1. GLYCAM_93 Parameter Development", J. Phys. Chem., 1995, 99, pp. 3832-3846.
Yano, T., et al., "Directed Evolution of an Aspartate Aminotransferase with New Substrate Specificities," Proc. Natl. Acad. Sci. USA, May 1998, pp. 5511-5515, vol. 95.
You, L., et al., "Directed Evolution of Subtilisin E in Bacillus subtilis to Enhance Total Activity in Aqueous Dimethylformamide," Protein Engineering, 1996, pp. 77-83, vol. 9, Oxford University Press.
Branden and Tooze, Introduction to Protein Structure (1999), 2nd Edition, Garland Science Publisher, pp. 3-12.
Unger et al., "The Genetic Algorithm approach to Protein Structure Prediction", Structure and Bonding (2004), vol. 110, pp. 153-175.
Bhanothu et al., "Review on characteristic developments of computational protein engineering," Journal of Pharmaceutical Research and Opinion (2012), vol. 2:8, pp. 70-93.
Grunberg et al., "Strategies for protein synthetic biology," Nucleic Acids Research (2010), vol. 38(8), pp. 2663-2675.
Otey et al., "Table S1 of Supporting Information", Structure-Guided Recombination Creates an Artificial Family of Cytochromes P450 PLoS Biol 4(5): e112. Published Apr. 11, 2006.
Current Protocols in Protein Science, 1995 & 2002, Unit 5.1 and 6.1.
Li et al.-B (Current Approaches for Engineering Proteins with Diverse Biological Properties, Adv Exp Med Biol. (2007-B) vol. 620, pp. 18-33.
Someya et al., Biologicatlly-Implemented Genetic Algorithm for Protein Engineering, Proceeding GECCO '09 Proceedings of the 11 th Annual conference on Genetic and evolutionary computation, pp. 233-240 ACM New York, NY, USA © 2009.
Jones DT, "Protein structure prediction in the postgenomic era", Curr Opin Struc Biol, 2000, 10, pp. 371-379.
Joo, H. et al., "Laboratory evolution of peroxide-mediated cytochrome P450 hydroxylation," Nature, Jun. 17, 1999, pp. 670-673, vol. 399.
Joo, Hyun et al., "A high-throughput digital imaging screen for the discovery and directed evolution of oxygenases." Chemistry and Biology, 1999, pp. 699-706.
Kay, "NMR methods for the study of protein structure and dynamics", Biochem. Cell Biol., 1997, 75, pp. 1-15.
Kikuchi et al., "An effective family shuffling method using single-stranded DNA," Gene, 2000, vol. 243, pp. 133-137.
Knappik, A. et al., "Engineered turns of a recombinant antibody improve its in vivo folding," Protein Engineering, Jan. 1995, pp. 81-89, vol. 8, No. 1, Oxford University Press.
Koehl et al., "Application of a self-consistent mean field theory to predict protein side-chains conformation and estimate their conformational entropy", Journal of Molecular Biology, vol. 239, pp. 249-275, 1994.
Koehl & Delarue, "Mean-field Minimization Methods for Biological Macromolecules", Curr. Opin. In Struct. Biol., 1996, 6, pp. 222-226.
Kuchner, O. et al., "Directed evolution of enzyme catalysts," Trends in Biotechnology, Dec. 1997, pp. 523-530, vol. 15, Elsevier Science Ltd.
Kuhn-Velten, W., "Effects of Compatible Solutes on Mammalian Cytochrome P450 Stability," 1997, pp. 132-135, Verlag der Zeitschrift fur Naturforschung.
Landwehr, et al., "Diversification of Catalytic Function in a Synthetic Family of Chimeric Cytochrome P450s", Chemistry and Biology, Current Biology, vol. 14, No. 3, Mar. 23, 2007, pp. 269-278.
Lazar, "De Novo Design of the Hydrophobic Core of Ubiquitin" Protein Science, 1997, 6, pp. 1167-1178.
Lee & Richards, "The Interpretation of Protein Structures: Estimation of Static Accessibility", J. Mol. Biol., 1971, 55, pp. 379-400.
Lee & Subbiah, "Prediction of Protein Side-chain Conformation by Packing Optimization", J. Mol. Biol., 1991, 217, pp. 373-388.
Lee, "Predicting Protein Mutant Energetics by Self-consistent Ensemble Optimization", J. Mol. Biol., 1994, 236, pp. 918-939.
Lee C et al., "Accurate prediction of the stability and activity effects of site directed mutagenesis on a protein core", Nature, 1991, 352, pp. 448-451.
Leung, D. et al., "A Method for Random Mutagenesis of a Defined DNA Segment Using a Modified Polymerase Chain Reaction," Technique, A Journal of Methods in Cell and Molecular Biology, Aug. 1989, pp. 11-15, vol. 1, No. 1, Saunders Scientific Publications.
Levitt et al., "Protein folding: The endgame", Annu. Rev. Biochem., 1997, 66, pp. 549-579.
Lewis, D., "P450 Substrate Specificity and Metabolism," Cytochrome P450: Structure, Function and Mechanism, Aug. 2001, pp. 115-166, Taylor & Francis Publishers.
Lewis, D. F. W., et al., "Molecular modeling of CYP1 family enzymes CYP1A1, CYP1A2, CYP1A6 and CYP1B1 based on sequence homology with CYP102," Toxicology, 139, 1999, pp. 53-79.
Li, Huiying et al., "The Structure of the cytochrome p450BM-3 haem domain complexed with the fatty acid substrate, palmitoleic acid," Nature Structural Biology, 1997, pp. 140-146.
Li, et al., "Emergence of Preferred Structures in a Simple Model of Protein Folding", Science, 1996, 273, pp. 666-669.
Li, Q. et al., "Rational evolution of a medium chain-specific cytochrome P-450 BM-3 variant," Biochimica et Biophysica Acta, 2001, pp. 114-121, 1545, Elsevier Science B.V.
Li, Qing-Shan, J. Ogawa, R. D. Schmid, and S. Shimizu, "Engineering Cytochrome P450 BM-3 for Oxidation of Polycyclic Aromatic Hydrocarbon" Appl. and Env. Microbiol. Dec. 2001, 67(10): 5735-5739.
Li et al., "Directed evolution of the fatty-acid hydroxylase P450 BM-3 into an indole-hydroxylating catalyst," Chemistry 2000, vol. 6, pp. 1531-1536.
Li et al., "residue size at position 87 of cytochrome P450 BM-3 determines its stereo selectivity in propylbenzene and 3-chlorostyrene oxidation," FEBS Lett 508, 2001, pp. 249-252.
Li, H., et al., "Characterization of Recombinant Bacillus megaterium Cytochrome P-450BM-3 and Its Two Functional Domains", Journal of Biological Chemistry, vol. 266, No. 18, 1991:266: pp. 11909-11914.
Li, Q. S., et al.; "Critical Role of the residue size at position 87 in H2O2-dependent substrate hydroxylation activity in H2O2 inactivation of cytochrome P450-BM-3"; Biochem, Biophysics Res Commun. vol. 280, No. 5, Abstract, 2001: pp. 1258-1261.
Lipman, D. J. and Pearson W. R., Rapid and Sensitive Protein Similarity Searches, Science, vol. 227, 1985, pp. 1435-1441.
Lutz et al., "Creating multiple crossover DNA libraries independent of sequence identity," Proc. Natl Acad Sci USA, 2001. vol. 98, pp. 11248-11253.
Mackerell et al., In the Encyclopedia of Computational Chemistry, vol. 1, pp. 271-277, John Wiley & Sons, Chichester, 1998, AMBER.
Malakaukas & Mayo, "Design, structure and stability of a hyperthermophilic protein variant", Nature Struct. Biol., 1998, 5, pp. 470-475.
Marchler-Bauer et al., "MMDB: Entrez's 3D structure database", Nucl. Acids Res., 1999, 27, pp. 240-243.
Martineau, P. et al., "Expression of an Antibody Fragment at High Levels in the Bacterial Cytoplasm," J. Mol. Biol., 1998, pp. 117-127, vol. 280, No. 1, Academic Press.
Matson, R. et al., "Characteristics of a Cytochrome P-450-Dependent Fatty Acid ω-2 Hydroxylase From Bacillus Megaterium," Biochimica et Biophysica Acta, 1977, pp. 487-494, 487, Elsevier/ North Holland Biomedical Press.
Mayhew et al., "Benzocycloarene hydroxylation by P450 biocatalysis", New J. Chem., 2002, vol. 26, pp. 35-42.
Mayo et al., "DREIDING : A Generic Force Field for Molecular Simulations", J. Phys. Chem., 1990, 94, pp. 8897-8909.
Meyer et al., "Library analysis of SCHEMA-guided protein recombination," Prot. Sci., 2003, vol. 12, No. 8, pp. 1686-1693.
Miles, Caroline S. et al., "Protein engineering of cytochromes P-450," Biochimica et Biophysica Acta 1543, 2000, pp. 383-407.
Minshull, J. et al., "Protein evolution by molecular breeding," Chemical Biology, 1999, pp. 284-290, 3, Elsevier Science Ltd.
Mitraki, A. et al., "Amino acid substitutions influencing intracellular protein folding pathways," FEBS Letters, Jul. 1992, pp. 20-25, vol. 307, No. 1, Elsevier Science Publishers B.V.

(56) References Cited

OTHER PUBLICATIONS

Miura, Yoshiro, et al., "ω-1, ω-2 and ω-3 hydroxylation of long-chain fatty acids, amides and alcohols by a soluble enzyme system from Bacillus megaterium," Biochimica et Biophysica Acta 388, 1975, pp. 305-317.

Miyazaki, K. et al., "Directed Evolution Study of Temperature Adaptation in a Psychrophilic Enzyme," Journal Mol. Biol., 2000, pp. 1015-1026, 297, Academic Press.

Miyazaki, et al. "Exploring Nonnatural Evolutionary Pathways by Saturation Mutagenesis: Rapid Improvement of Protein Function", J. Molecular Evolution, 1999, 49, pp. 716-720.

Modi, S. et al., "NMR Studies of Substrate Binding to Cytochrome P450 BM3: Comparisons to Cytochrome P450 cam," Biochemistry, 1995, pp. 8982-8988, vol. 34, No. 28, American Chemical Society.

Moore, J. et al., "Strategies for the in vitro Evolution of Protein Function: Enzyme Evolution by Random Recombination of Improved Sequences," J. Mol. Biol., 1997, pp. 336-347, 272, Academic Press Limited.

Munro, A. et al., "Alkane Metabolism by Cytochrome P450 BM3," Biochemical Society Transactions, 1993, p. 412S, 21.

Munro, A. et al., "Probing electronic transfer in flavocytochrome P-450 BM3 and its component domains," Eur. J. Biochem., 1996, pp. 403-409, FEBS.

Murataliev et al., "Chimeragenesis of the Fatty Acid Binding Site of Cytochrome P450BM3. Replacement of Residues 73-84 with the Homologous Residues from the Insect Cytochrome P450 CYP4C7", Biochemistry, 2004, vol. 43, No. 7, pp. 1771-1780.

Narhi, L. et al., "Identification and Characterization of Two Functional Domains in Cytochrome P-450BM-3, a Catalytically Self-sufficient Monooxygenase Induced by Barbiturates in Bacillus megaterium," The Journal of Biological Chemistry, May 1987, pp. 6683-6690, vol. 262, No. 14, The American Society of Biological Chemists, Inc.

Narhi, L. et al., "Characterization of a Catalytically Self-sufficient 199,000-Dalton Cytochrome P-450 Monooxygenase Induced by Barbiturates in Bacillus megaterium," The Journal of Biological Chemistry, Jun. 1986, pp. 7160-7169, vol. 261, No. 16, The American Society of Biological Chemists, Inc.

Nelson, D., "Appendix A—Cytochrome P450 Nomenclature and Alignment of Selected Sequences," Cytochrome P450: Structure, Mechanism, and Biochemistry, Second Ed., 1995, pp. 575-606, Plenum Press, NY.

Ness, J. et al., "DNA shuffling of subgenomic sequences of subtilisin," Nature Biotechnology, Sep. 1999, pp. 893-896, vol. 17, No. 9, Nature Publishing Group.

Neylon, C., "Chemical and biochemical strategies for the randomization of protein encloding DNA sequences: library construction methods for directed evolution," Nucleic Acid Res., 2004, vol. 32, No. 4, pp. 1448-1459.

Nielsen et al., "Improving macromolecular electrostatics calculations", Protein Engineering, 1999, 12, pp. 657-662.

Noble, M. et al., "Roles of key active-site residues in flavocytochrome P450 BM3," Biochem. J., 1999, pp. 371-379, 339, Biochemical Society.

Oakley et al., "Macromolecular crystallography as a tool for investigating drug, enzyme and receptor interactions", Olin Exp Pharmacol P., 2000, 27, pp. 145-151.

Oliver, C. et al., "Engineering the substrate specificity of Bacillus megaterium cytochrome P-450 BM3: hydroxylation of alkyl trimethylammonium compounds," Biochem. J., 1997, pp. 537-544, 327, The Biochemical Society, London, England.

Oliver, C.F., et al., "A single Mutation in Cytochrome P450 BM3 Changes Substrate Orientation in a Catalytic Intermediate and the Regiospecificity of Hydroxylation", Biochemistry 1997; 36:1567-72.

O'Maille et al., Structure-based combinatorial protein engineering (SCOPE), J. Mol. Biol., 2002, vol. 321, pp. 677-691.

Ost, T. et al., "Rational re-design of the substrate binding site of flavocytochrome P450 BM3," FEBS Letters, 2000, pp. 173-177, 486, Elsevier Science B.V.

Ost, T. W., et al. "Rational re-design of the substrate binding site of flavocytochrome P450 BM3"; FEBS Lett., vol. 486, No. 2, Abstract 2000.

Ostermeier, M. et al., "Incremental Truncation as a Strategy in the Engineering of Novel Biocatalysts," Bioorganic & Medicinal Chemistry, 1999, pp. 2139-2144, 7, Elsevier Science Ltd.

Otey et al., "Functional evolution and structural conservation in chimeric cytochromes P450: Calibrating a structure-guided approach," Chemistry and Biology, 2004, vol. 11, pp. 309-318.

Otey, Christopher R. et al., "Structure-guided recombination creates an artificial family of cytochromes P450", PLOS Biology, vol. 4, No. 5, May 2006, pp. 789-798.

Pabo et al., "Computer-Aided Model-Building Strategies for Protein Design", Biochemistry, 1986, 25, pp. 5987-5991.

Patten, P. et al., "Applications of DNA shuffling to pharmaceuticals and vaccines," Biotechnology, 1997, pp. 724-733, vol. 8, Elsevier Science Ltd.

Paulsen, M. et al., "Dramatic Differences in the Motions of the Mouth of Open and Closed Cytochrome P450BM-3 by Molecular Dynamics Simulations," Proteins: Structure, Function and Genetics, 1995, pp. 237-243, Wiley-Liss, Inc.

Pearson W. R. and Lipman D. J., "Improved tools for biological sequence comparison", Proc. Natl Acad Sci USA 1988; 85:2444-2448.

Peters, Matthew W., "Regio- and Enantioselective Alkane Hydroxylation with Engineered Cytochromes P450 BM-3," J. Am. Chem. Soc., vol. 125, 2003, pp. 13442-13450.

Peterson, J. et al., "Chapter 5—Bacterial P450s—Structural Similarities and Functional Differences", Cytochrome P450: Structure, Mechanism, and Biochemistry, Second Ed., 1995, pp. 151-180.

Peterson et al., "The many faces of P450s and their structural and functional implications," Sixth International Symposium on Cytrochrome P450 Biodiversity: University of California, Los Angels, 2002, p. 26.

Petrounia, Ioanna and F. H. Arnold "Designed evolution of enzymatic properties," Current Opinion in Biotech., 11 (4): 325-330, Aug. 2000.

Pierce et al., "Conformational splitting: A more powerful criterion for dead-end elimination", Journal of Computational Chemistry, 2000, 21, pp. 999-1009.

Pjura, et al., "Development of an in vivo method to identify mutants of phage T4 lysozyme of enhanced thermostability", Protein Science, 1993, 2, pp. 2217-2225.

Pompon, et al., "Protein engineering by cDNA recombination in yeasts: shuffling of mammalian cytochrome P-450 functions," Gene, 1989, vol. 83, pp. 15-24.

Porter, et al., "Cytochrome P-450. Multiplicity of isoforms, substrates, and catalytic and regulatory mechanisms," J. Biol. Chem., 1991, vol. 266, pp. 13469-13472.

Porter, "Cytochrome P450 reductase", printed Apr. 5, 2004, http://www.uky.edu/Pharmacy/ps/porter/CPR.htm.

Ramarao et al., "Identification by in vitro mutagenesis of the interaction of two segments of C2MstC1, a chimera of cytochromes P450 2C2 and P450 2C1," The Journal of Biological Chemistry, Jan. 27, 1995, vol. 270, No. 4, pp. 1873-1880.

Reeck et al., "Homology" in proteins and nucleic acids: a terminology muddle and a way out of it, Cell, 1987, 50, pp. 667.

Ricki, Lewis, "DNA sequencing software teases meaning from genes," May 31, 1993, The Scientist, pp. 1-4, vol. 7, No. 11.

Roberts, "The power of evolution: accessing the synthetic potential of P450s", Chemistry & Biology, 1999, vol. 6, No. 10, pp. R269-R272.

Ruettinger, R., et al., "Coding Nucleotide, 5' Regulatory, and Deduced Amino Acid Sequences of P-450BM-3, a Single Peptide Cytochrome P-450:NADPH-P-450 Reductase from Bacillus megaterium," The Journal of Biological Chemistry, Jul. 5, 1989, pp. 10987-10995, vol. 264, No. 19, The American Society for Biochemistry and Molecular Biology, Inc.

Ruettinger, R., et al., "Epoxidation of Unsaturated Fatty Acids by a Soluble Cytochrome P-450-dependent System from Bacillus megaterium," The Journal of Biological Chemistry, Jun. 10, 1981, pp. 5728-5734, vol. 256, No. 11.

(56) References Cited

OTHER PUBLICATIONS

Salazar, Oriana, P. C. Cirino, F. H. Arnold "Thermostability of a Cytochrome P450 Peroxygenase," Chembiochem, 4 (9):891-893, Sep. 2003.

Sasai, "Conformation, energy, and folding ability of selected amino acid sequences", Proc. Natl. Acad. Sci. USA, 1995, 92, pp. 8438-8442.

Saven et al., "Statistical Mechanics of the Combinatorial Synthesis and Analysis of Folding Macromolecules", J Phys Chem, vol. 101, pp. 8375-8389, 1997.

Schein C., "Solubility as a Function of Protein Structure and Solvent Components," Bio/Technology, Apr. 1990, pp. 308-317, vol. 8, No. 4.

Schneider, S., et al., "Controlled Regioelectivity of Fatty Acid Oxidation by Whole Cells Producing Cytochrome P450BM-3 Monooxygenase Under Varied Dissolved Oxygen Concentrations," Biotechnology and Bioengineering, Aug. 5, 1999, pp. 333-341, vol. 64, No. 3, John Wiley & Sons, Inc.

Schneider, et al., "Production of chiral hydroxyl long chain fatty acids by whole cells producing cytochrome P450 (BM-3) monoxygenase," Tetrahedron Asymetry, 1998, Vool. 9, No. 16, pp. 2833-2844.

Schneider et al., "A designed buried salt bridge in a heterodimeric coil", J. Am. Chem. Soc., 1997, 119, pp. 5742-5743.

Schwaneberg, U., et al., "A Continuous Spectrophotometric Assay for P450 BM-3, a Fatty Acid Hydroxylating Enzyme, and Its Mutant F87A," Analytical Biochemistry, 1999, pp. 359-366, vol. 269, Academic Press.

Schwaneberg, U., et al., "Cost-Effective Whole-Cell Assay for Laboratory Evolution of Hydroxylases in *Escherichia coli*," Journal of Biomolecular Screening, 2001, pp. 111-117, vol. 6, No. 2, The Society for Biomolecular Screening.

Schwaneberg, U., et al., "P450 Monooxygenase in Biotechnology—Single-Step, Large-Scale Purification Method for Cytochrome P450 BM-3 by Anion-Exchange Chromatography," Journal of Chromatography, 1999, pp. 149-159, vol. 848, Elsevier Science B.V.

Seghezzi et al., "Identification of characterization of additional members of the cytochrome-P450 multigene family Cyp52 of candida-tropicalis," DNA and Cell Biology, 1992, vol. 11, No. 10, pp. 767-780.

Shafikhani, S., et al., "Generation of Large Libraries of Random Mutants in Bacillus subtilis by PCR-Based Plasmid Multimerization," BioTechniques, Aug. 1997, pp. 304-310, vol. 23, No. 2.

Shakhnovich, "Proteins with selected sequences fold into unique native conformation", Phys. Rev. Lett., 1994, 72, pp. 3907-3910.

Wittman-Regis, Agnes, International Preliminary Report on Patentability and Written Opinion, PCT Application No. PCT/US2012/047637, The International Bureau of WIPO, Date Mailed: Feb. 6, 2014.

\* cited by examiner

```
(SEQ ID NO:)
H_insolens     (6)   MAK-FFLTAAFAAAALAAPVVEERQNCAPTWGQCGGIGFNGPTCCQSGSTCVKQNDWYSQ  59
C_thermophilum (8)   MAKQLLLTAALAATSLAAPLLEERQSCSSVWGQCGGINYNGPTCCQSGSVCTYLNDWYSQ 60
HJPlus         (2)   ------------------------ASCSSVWGQCGGQNWSGPTCCASGSTCVYSNDYYSQ 36
H_jecorina     (4)   MIVGILTTLATLATLAASVPLEERQACSSVWGQCGGQNWSGPTCCASGSTCVYSNDYYSQ 60
                                             *:...******  .:.***** ***.*.  **:***

H_insolens           CLPG-SQVTTSTTSTSSSSTTSRATSTTRTGGVTSITTAPTRTVTIPGGATTTASYNGN  118
C_thermophilum       CIPGQAQPGTTSTTARTTSTSTTSTSSVRPTTSNTPVTTAPP-TTTIPGGASSTASYNGN 119
HJPlus               CLPG----AASSSSSTRAASTTSRVSPTTSRSSSATPPPGST-TTRVPPVGSGTATYSGN  91
H_jecorina           CLPG----AASSSSSTRAASTTSRVSPTTSRSSSATPPPGST-TTRVPPVGSGTATYSGN 115
                     *:**    ::*:::  ::::*: .:..    . :. .....  *. :*  .: **:*.**

H_insolens           PFEGVQLWANNYYRSEVHTLAIPQITDPALRAAASAVAEVPSFQWLDRNVTVDTLLVETL 178
C_thermophilum       PFSGVQLWANTYYSSEVHTLAIPSLS-PELAAKAAKVAEVPSFQWLDRNVTVDTLFSGTL 178
HJPlus               PFEGVQLWANNYYRSEVHTLAIPQITDPALRAAASAVAEVPSFMWLDT-LDKTPLMEQTL 150
H_jecorina           PFVGVTPWANAYYASEVSSLAIPSLTG-AMATAAAAVAKVPSFMWLDT-LDKTPLMEQTL 173
                     ** **   *** ** *** :****.::    : : *: **:**** ***   :  .*:  **

H_insolens           SEIRAANQAGANPPYAAQIVVYDLPDRDCAAAASNGEWAIANNGANNYKGYINRIREILI 238
C_thermophilum       AEIRAANQRGANPPYAGIFVVYDLPDRDCAAAASNGEWSIANNGANNYKRYIDRIRELLI 238
HJPlus               ADIRTANKNGGN--YAGQFVVYDLPDRDCAALASNGEYSIADGGVAKYKNYIDTIRQIVV 208
H_jecorina           ADIRTANKNGGN--YAGQFVVYDLPDRDCAALASNGEYSIADGGVAKYKNYIDTIRQIVV 231
                     ::*:**:**:  *.*  **. :********** *****::**:,*.  :** **: **::::

H_insolens           SFSDVRTILVIEPDSLANMVTNMNVAKCSGAASTYRELTIYALKQLDLPHVAMYMDAGHA 298
C_thermophilum       QYSDIRTILVIEPDSLANMVTNMNVQKCSNAASTYKELTVYALKQLNLPHVAMYMDAGHA 298
HJPlus               EYSDIRTLLVIEPDSLANLVTNLGTPKCANAQSAYLECINYAVTQLNLPNVAMYLDAGHA 268
H_jecorina           EYSDIRTLLVIEPDSLANLVTNLGTPKCANAQSAYLECINYAVTQLNLPNVAMYLDAGHA 291
                     .:**:**:***********:***:..  **:.* *:*  *   **:.**:**:*****:*****

H_insolens           GWLGWPANIQPAAELFAKIYEDAGKPRAVRGLATNVANYNAWSISSPPPYTSPNPNYDEK 358
C_thermophilum       GWLGWPANIQPAAELFAQIYRDAGRPAAVRGLATNVANYNAWSIASPPSYTSPNPNYDEK 358
HJPlus               GWLGWPANQDPAAQLFANVYKNASSPRALRGLATNVANYNAWSIASPPSYTSPNPNYDEK 328
H_jecorina           GWLGWPANQDPAAQLFANVYKNASSPRALRGLATNVANYNGWNITSPPSYTQGNAVYNEK 351
                     ********  :***:***::*.:*. * *:***********.*.*:***.**. *. *:**

H_insolens           HYIEAFRPLLEARGFP-AQFIVDQGRSGKQPTGQKEWGHWCNAIGTGFGMRPTANTGHQY 417
C_thermophilum       HYIEAFAPLLRNQGFD-AKFIVDTGRNGKQPTGQLEWGHWCNVKGTGFGVRPTANTGHEL 417
HJPlus               HYIEAFAPLLRNQGFD-AKFIVDTGRNGKQPTGQLEWGHWCNVKGTGFGVRPTANTGHEL 387
H_jecorina           LYIHAIGPLLANHGWSNAFFITDQGRSGKQPTGQQWGDWCNVTGTGFGIRPSANTGDSL  411
                     **.*: ***  :*:  * **.* **.*******  :**.***.  *****:**:****..

H_insolens           VDAFVWVKPGGECDGTSDTTAARYDYHCGLEDALKPAPEAGQWFQAYFEQLLRNANPPF- 476
C_thermophilum       VDAFVWVKPGGESDGTSDTSAARYDYHCGLSDALTPAPEAGQWFQAYFEQLLINANPPF- 476
HJPlus               VDAFVWVKPGGESDGTSDSSAPRFDSHCALPDALQPAPQAGAWFQAYFVQLLTNANPSFL 447
H_jecorina           LDSFVWVKPGGECDGTSDSSAPRFDSHCALPDALQPAPQAGAWFQAYFVQLLTNANPSFL 471
                     :*:*********.******.*****::*.*:* **.* *** ***:** ****** *** ****.*

H_insolens           ------
C_thermophilum       ------
HJPlus               HHHHHH 453
H_jecorina           ------
```

STABLE FUNGAL CEL6 ENZYME VARIANTS

CROSS REFERENCE TO RELATED APPLICATIONS

The application claims priority under 35 U.S.C. §119 to U.S. Provisional Application Ser. No. 61/510,914, filed, Jul. 22, 2011, the disclosure of which is incorporated herein by reference.

STATEMENT REGARDING FEDERALLY SPONSORED RESEARCH

This invention was made with government support under Grant No. W911NF-09-D-0001 awarded by the Army Research Office. The government has certain rights in the invention.

TECHNICAL FIELD

The disclosure provides thermostable variants of fungal Cel6 (cellobiohydrolase II) enzymes and their use to hydrolyze cellulose.

BACKGROUND

The performance of cellulase mixtures in biomass conversion processes depends on many enzyme properties including stability, product inhibition, synergy among different cellulase components, productive binding versus nonproductive adsorption and pH dependence, in addition to the cellulose substrate physical state and composition. Given the multivariate nature of cellulose hydrolysis, it is desirable to have diverse cellulases to choose from in order to optimize enzyme formulations for different applications and feedstocks.

SUMMARY

The disclosure provide recombinant or substantially purified polypeptides comprising a sequence that is at least 67.7% identical to a sequence set forth in SEQ ID NO:2, 4, 6, 8, 12, 14, 16, 18, 20, 22, 24, 26, or 28 and having cellulase activity and increased thermostability compared to a polypeptide comprising SEQ ID NO:4, 6, or 8. In one embodiment, the recombinant or substantially purified polypeptide comprises at least 67.7% identity (e.g., 67.7, 70, 80, 85, 90, 95, 98, 99, or 100% identity) to SEQ ID NO:2 and having one or more amino acid substitutions at residues selected from the group consisting of N14, S30, V128, V131, M135, C246, Q277, S293, S317, S406, and S413, and wherein the polypeptide has cellulase activity and comprises increased thermostability compared to a wild-type enzyme of SEQ ID NO: 4, 6, or 8. In another embodiment, the polypeptide comprises one or more substitutions selected from the group consisting of N14S, S30F, S30M, V128A, V131E, M135L, C246A, C246G, C246L, C246S, Q277L, S293R, S317P, S317W, S406P, S413F, and S413W. In yet another embodiment, the polypeptide comprises a sequence as set forth in SEQ ID NO:4 and wherein residues N14, S30, V128, V131, M135, C246, Q277, S293, S317, S406, and S413 of SEQ ID NO:2 correspond to residues N38, S54, V151, V154, M158, C269, Q300, S316, S340, S430, and S437 in SEQ ID NO:4. In a further description, the polypeptide comprises SEQ ID NO:4 and has one or more substitutions at a residue selected from N38, S54, V151, V154, M158, C269, Q300, S316, S340, S430, and S437. In another embodiment, the polypeptide comprises a sequence as set forth in SEQ ID NO:6 and wherein residues N14, S30, V128, V131, M135, C246, Q277, S293, S317, S406, and S413 of SEQ ID NO:2 correspond to residues G37, Q53, V155, V158, Q162, L276, I307, K323, P347, T436, and Y443 in SEQ ID NO:6. In a further description, the polypeptide comprises SEQ ID NO:6 and has one or more substitutions at a residue selected from G37, Q53, V155, V158, Q162, L276, I307, K323, P347, T436, and Y443. In yet another embodiment, the polypeptide comprises a sequence as set forth in SEQ ID NO:8 and wherein residues N14, S30, V128, V131, M135, C246, Q277, S293, S317, S406, and S413 of SEQ ID NO:2 correspond to residues or N38, L54, V155, V158, Q162, L276, I307, R323, S347, T436, and Y443 in SEQ ID NO:8. In a further description, the polypeptide comprises SEQ ID NO:8 and has one or more substitutions at a residue selected from N38, L54, V155, V158, Q162, L276, I307, R323, S347, T436, and Y443. In another embodiment, the polypeptide comprise a sequence that is at least 80%, 85%, 87%, 88%, 89%, 90%, 91%, 92%, 93%, 94%, 95%, 96%, 97%, 98%, 99% or 100% identical to the sequence as set forth in SEQ ID NO:12, 14, 16, 18, 20, 22, 24, 26, or 28. In another of the foregoing embodiments, the polypeptide can further comprise a cellulose binding domain (CBD) operably linked to the polypeptide. In one embodiment, the CBD comprises a sequence as set forth in SEQ ID NO:10.

The disclosure also provides a recombinant polypeptide comprising at least 80% identity to SEQ ID NO:6 and having one or more substitutions at a residue selected from the group consisting of G37, Q53, V155, V158, Q162, L276, I307, K323, P347, T436, and Y443 and wherein the polypeptide has cellulase activity and comprises increased thermostability compared to a wild-type enzyme of SEQ ID NO: 4, 6, or 8. In a further embodiment, the substitutions are selected from the group consisting of G37S, Q53F, Q53M, V155A, V158E, Q162L, L276A, L276G, L276S, I307L, K323R, P347W, T436P, Y443F, and Y443W. In yet another embodiment, the polypeptide comprising SEQ ID NO:6 has up to 50, 25, 10, or 5 conservative amino acid substitutions excluding specific residues G37, Q53, V155, V158, Q162, L276, I307, K323, P347, T436, and/or Y443, wherein at least one or more of these specific residues have substitutions selected form the group consisting of G37S, Q53F, Q53M, V155A, V158E, Q162L, L276A, L276G, L276S, I307L, K323R, P347W, T436P, Y443F, and Y443W.

The disclosure also provides a recombinant polypeptide comprising at least 80% identity to SEQ ID NO:4 and having one or more substitutions at a residue selected from the group consisting of N38, S54, V151, V154, M158, C269, Q300, S316, S340, S430, and S437 and wherein the polypeptide has cellulase activity and comprises increased thermostability compared to a wild-type enzyme of SEQ ID NO: 4, 6, or 8. In one embodiment, the substitutions are selected from the group consisting of N38S, S54F, S54M, V151A, V154E, C269A, C269G, C269L, C269S, Q300L, S316R, S340P, S340W, S430P, S437F, and S437W. In another embodiment, the recombinant polypeptide comprising SEQ ID NO:6 has up to 50, 25, 10, or 5 conservative amino acid substitutions excluding specific residues N38, S54, V151, V154, M158, C269, Q300, S316, S340, S430, and S437, wherein at least one or more of these specific residues have substitutions selected form the group consisting of N38S, S54F, S54M, V151A, V154E, C269A, C269G, C269L, C269S, Q300L, S316R, S340P, S340W, S430P, S347F, and S427W.

The disclosure also provides a recombinant polypeptide comprising at least 80% identity to SEQ ID NO:8 and having one or more substitutions at a residue selected from the group consisting of N38, L54, V155, V158, Q162, L276, I307, R323, S347, T436, and Y443 and wherein the polypeptide has cellulase activity and comprises increased thermostability compared to a wild-type enzyme of SEQ ID NO: 4, 6, or 8. In one embodiment, the recombinant polypeptide the substitutions are selected from the group consisting of N38S, L54F, L54M, V155A, V158E, Q162L, L276A, L276G, L276S, I307L, S347P, S347W, T436P, Y443F, and Y443W. In yet another embodiment, the polypeptide comprising SEQ ID NO:6 has up to 50, 25, 10, or 5 conservative amino acid substitutions excluding specific residues N38, L54, V155, V158, Q162, L276, I307, R323, S347, T436, and Y443; wherein at least one or more of these specific residues have substitutions selected form the group consisting of N38S, L54F, L54M, V155A, V158E, Q162L, L276G, L276A, L276S, I307L, S347P, S347W, T436P, Y443F, and Y443W.

In certain embodiment, a recombinant polypeptide of the disclosure comprises SEQ ID NO:2 having substitutions selected from the group consisting of: (a) one or more substitution at a residue selected from the group consisting of N14, S30, V128, V131, M135, C246, Q277, S293, S317, S406 and any combination thereof; and (b) a substitution at S413 and one or more substitutions at a residue selected from the group consisting of N14, S30, V128, V131, M135, C246, Q277, S293, S317, S406 and any combination thereof. In a further embodiment, a recombinant polypeptide of the disclosure comprises SEQ ID NO:2 having substitutions selected from the group consisting of: (a) one or more substitutions selected from the group consisting of N14S, S30F, S30M, V128A, V131E, M135L, C246A, C246G, C246L, C246S, Q277L, S293R, S317P, S317W, and S406P; (b) S413F and one or more additional substitutions selected from the group consisting of N14S, S30F, S30M, V128A, V131E, M135L, C246A, C246G, C246L, C246S, Q277L, S293R, S317P, S317W, and S406P; (c) S413P and one or more additional substitutions selected from the group consisting of N14S, S30F, S30M, V128A, V131E, M135L, C246A, C246G, C246L, C246S, Q277L, S293R, S317P, S317W, and S406P; and (d) S413W and one or more additional substitutions selected from the group consisting of N14S, S30F, S30M, V128A, V131E, M135L, C246A, C246G, C246L, C246S, Q277L, S293R, S317P, S317W, and S406P.

In certain embodiment, a recombinant polypeptide of the disclosure comprises SEQ ID NO:4 having substitutions at a positions selected from the group consisting of: (a) one or more residue selected from the group consisting of N38, S54, V151, V154, C269, S316, S430 and any combination thereof; (b) M158 and one or more additional residues selected from the group consisting of N38, S54, V151, V154, C269, S316, and S430; (c) Q300 and one or more additional residue selected from the group consisting of N38, S54, V151, V154, C269, S316, and S430; (d) S340 and one or more additional residue selected from the group consisting of N38, S54, V151, V154, C269, S316, and S430; and (e) S437 and one or more additional residue selected from the group consisting of N38, S54, V151, V154, C269, S316, and S430. In a further embodiment, a recombinant polypeptide of the disclosure comprises SEQ ID NO:4 having substitutions selected from the group consisting of: (a) one or more substitution selected from the group consisting of N38S, S54F, S54M, V151A, V154E, C269A, C269G, C269L, C269S, S316R, and S430P; (b) M158L and one or more additional substitutions selected from the group consisting of N38S, S54F, S54M, V151A, V154E, C269A, C269G, C269L, C269S, S316R, and S430P; (c) Q300L and one or more additional substitutions selected from the group consisting of N38S, S54F, S54M, V151A, V154E, C269A, C269G, C269L, C269S, S316R, and S430P; (d) S340P and one or more additional substitutions selected from the group consisting of N38S, S54F, S54M, V151A, V154E, C269A, C269G, C269L, C269S, S316R, and S430P; (e) S340W and one or more additional substitutions selected from the group consisting of N38S, S54F, S54M, V151A, V154E, C269A, C269G, C269L, C269S, S316R, and S430P; (f) S437F and one or more additional substitutions selected from the group consisting of N38S, S54F, S54M, V151A, V154E, C269A, C269G, C269L, C269S, S316R, and S430P; (g) S437P and one or more additional substitutions selected from the group consisting of N38S, S54F, S54M, V151A, V154E, C269A, C269G, C269L, C269S, S316R, and S430P; and (h) S437W and one or more additional substitutions selected from the group consisting of N38S, S54F, S54M, V151A, V154E, C269A, C269G, C269L, C269S, S316R, and S430P.

In certain embodiment, a recombinant polypeptide of the disclosure comprises SEQ ID NO:6 having substitutions at a positions selected from the group consisting of: (a) a residue selected from the group consisting of G37, Q53, V155, V158, Q162, L276, I307, K323, P347, and T436; and (b) Y443 and one or more additional residue selected from the group consisting of G37, Q53, V155, V158, Q162, L276, I307, K323, P347, and T436. In a further embodiment, a recombinant polypeptide of the disclosure comprises SEQ ID NO:6 having substitutions selected from the group consisting of: (a) a substitution selected from the group consisting of G37S, Q53F, Q53M, V155A, V158E, Q162L, L276A, L276G, L276S, I307L, K323R, P347W, and T436P; (b) Y443F and one or more additional substitutions selected from the group consisting of G37S, Q53F, Q53M, V155A, V158E, Q162L, L276A, L276G, L276S, I307L, K323R, P347W, T436P; and (c) Y443P and one or more additional substitutions from the group consisting of G37S, Q53F, Q53M, V155A, V158E, Q162L, L276A, L276G, L276S, I307L, K323R, P347W, T436P; and (d) Y443W and one or more additional substitutions selected from the group consisting of G37S, Q53F, Q53M, V155A, V158E, Q162L, L276A, L276G, L276S, I307L, K323R, P347W, and T436P.

In certain embodiment, a recombinant polypeptide of the disclosure comprises SEQ ID NO:8 having substitutions at a positions selected from the group consisting of: (a) a residue selected from the group consisting of N38, L54, V155, V158, Q162, L276, I307, R323, S347, and T436; and (b) Y443 and one or more additional residue selected from the group consisting N38, L54, V155, V158, Q162, L276, I307, R323, S347, and T436. In a further embodiment, the recombinant polypeptide comprises SEQ ID NO:8 having substitutions selected from the group consisting of: (a) a residue selected from the group consisting of N38S, L54F, L54M, V155A, V158E, Q162L, L276A, L276G, L276S, I307L, S347P, S347W, and T436P; (b) Y443F and one or more additional substitutions selected from the group consisting N38S, L54F, L54M, V155A, V158E, Q162L, L276A, L276G, L276S, I307L, S347P, S347W, and T436P; (c) Y443P and one or more additional substitutions selected from the group consisting N38S, L54F, L54M, V155A, V158E, Q162L, L276A, L276G, L276S, I307L, S347P, S347W, and T436P; and (d) Y443W and one or more additional substitutions selected from the group consisting N38S, L54F, L54M, V155A, V158E, Q162L, L276A, L276G, L276S, I307L, S347P, S347W, and T436P.

In various embodiments of the disclosure substitutions in SEQ ID NO:2 are as described above, but specifically exclude substitutions at S413. In various embodiments of the disclosure substitutions in SEQ ID NO:4 are as described above, but specifically exclude substitutions at one or more positions selected from the group consisting of M158, Q300, S340, S437, and S437. In various embodiments of the disclosure substitutions in SEQ ID NO:6 are as described above, but specifically exclude substitutions at Y443. In various embodiments of the disclosure substitutions in SEQ ID NO:8 are as described above, but specifically exclude substitutions at Y443.

In any of the foregoing embodiments comprising the substitutions above, the resulting "modified" polypeptide comprises a polypeptide having cellulase activity and improved thermostability compared to a wild-type enzyme comprising SEQ ID NO:4, 6, or 8.

The disclosure also provides a polynucleotide encoding a polypeptide of any of the foregoing embodiments.

The disclosure also provides a vector comprising a polynucleotide described above as well as host cells comprising a vector of the disclosure.

The disclosure also provides a host cell that expresses a polypeptide described herein in any of the embodiments described above.

The disclosure also provides enzymatic preparation comprising a polypeptide of the disclosure.

The disclosure also provides a method of treating a biomass comprising cellulose, the method comprising contacting the biomass with a polypeptide described in any of the foregoing embodiments, an enzymatic preparation of the disclosure, or a host cell expressing a polypeptide of the disclosure.

BRIEF DESCRIPTION OF THE FIGURES

FIG. 1 shows alignment of Cel6a amino acid sequences from *H. insolens* (SEQ ID NO:6), *H. jecorina* (HJ) (SEQ ID NO:4), *C. thermophilum* (SEQ ID NO:8), and HJPlus (SEQ ID NO:2). Residues with double underlining are specific residues for mutation.

DETAILED DESCRIPTION

Figure 2:
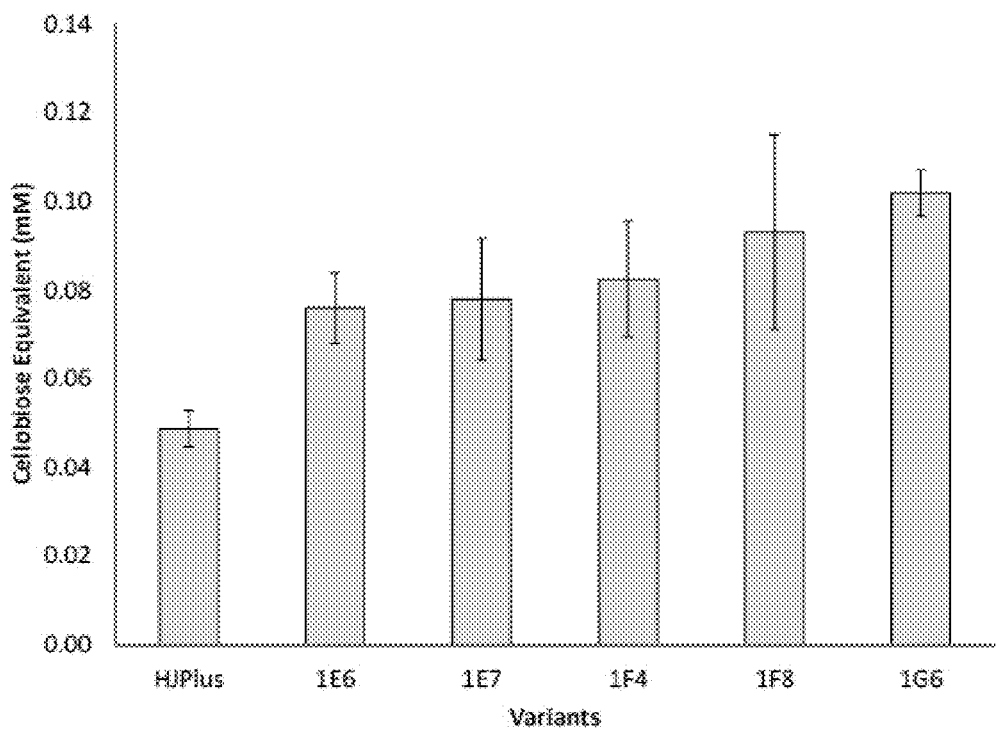
FIG. 2 shows the total activity at 75° C. (measured as cellobiose equivalents released) from 3-day *S. cerevisiae* culture supernatant of cultures expressing HJPlus and the top five variants from the first generation random mutagenesis library.

As used herein and in the appended claims, the singular forms "a," "and," and "the" include plural referents unless the context clearly dictates otherwise. Thus, for example, reference to "a Cel6 enzyme" includes a plurality of such enzymes and reference to "the protein" includes reference to one or more proteins, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Although methods and materials similar or equivalent to those described herein can be used in the practice of the disclosed methods and compositions, the exemplary methods, devices and materials are described herein.

Unless defined otherwise, all technical and scientific terms used herein have the same meaning as commonly understood to one of ordinary skill in the art to which this disclosure belongs. Thus, as used throughout the instant application, the following terms shall have the following meanings.

Cellulose is the main structural component of most plant cell walls, making it the most abundant biopolymer on earth. Cellulose is a polysaccharide composed of glucosyl units linked together by β-1,4 glycosidic bonds. The β-linkage ensures that the subunits rotate 180° every two glucose subunits along the cellulose chain. The rotation makes the cellulose chains straight and highly symmetrical. X-ray diffraction and nuclear magnetic resonance studies have shown that cellulose chains form extensive intramolecular and intermolecular hydrogen bonds between the hydroxyl groups and the oxygen in the pyranose ring, producing crystalline elementary fibrils with strong tensile strength and low accessibility. The extensive hydrogen bonding makes cellulose a very recalcitrant material, with a half-life of over four million years from spontaneous hydrolysis at 25° C. Despite this recalcitrance, nature has provided several enzyme solutions capable of hydrolyzing cellulose into a form that can be utilized by microorganisms as a source of carbon and energy.

Recent studies have documented the superior performance of cellulases from thermophilic fungi relative to their mesophilic counterparts in laboratory scale biomass conversion processes, where enhanced stability leads to retention of activity over longer periods of time at both moderate and elevated temperatures. Fungal cellulases are attractive because they are highly active and can be expressed in fungal hosts such as *Hypocrea jecorina* (anamorph *Trichoderma reesei*) at levels up to 40 g/L in the supernatant. Unfortunately, the set of documented thermostable fungal cellulases is small. In the case of the processive cellobiohydrolase class II (CBH II) enzymes, fewer than 10 natural thermostable gene sequences are annotated in the CAZy database.

Fungal cellulases are important in industrial applications, from cotton softening in the textile industries to biofuel production in biorefineries. Specifically, cellulases are used in biorefineries to break down cellulosic biomass into fermentable sugars, from which biofuels and higher-value chemicals can be derived. For cellulosic biomass to become a feasible feedstock for transportation fuels and chemicals, the cost of production needs to be competitive with the current technology of producing them from fossil fuels. Thermostable cellulases are particularly interesting for biomass degradation for several reasons. Thermostable cellulases tend to be more stable during production, storage and over a range of temperatures and operating conditions. Thermostable enzymes are more resilient towards relatively harsh industrial treatments and conditions. They also can be used to hydrolyze cellulose at higher temperatures, where the enzymes can access the substrate and catalyze their reactions at a higher rate—assuming that the reaction temperature is lower than the denaturing temperature for the enzyme. The risk of contamination by microorganisms is also reduced at elevated temperatures, as is the viscosity of hydrolysis mixtures, which lowers process costs.

The mesophilic fungus *Hypocrea jecorina* (anamorph *Trichoderma reesei*) secretes an array of cellulose enzymes that work synergistically to degrade the cellulose to smaller oligomers and eventually to glucose. This fungus' collection of cellulases includes at least five endoglucanases (EGI-V), two cellobiohydrolases (Cel6a, Cel7a), β-glucosidases, and hemicellulases. In *Hypocrea jecorina*, cellobiohydrolase Cel7a, Cel6a, and EGII comprise 60±5%, 20±6%, and 12±3% of total cellulase protein, respectively. All three cellulases consist of a cellulose-binding domain (CBD) and a catalytic domain connected by a glycosylated peptide linker. Cellobiose is the primary product of cellulose hydrolysis by cellobiohydrolases Cel6a and Cel7a.

Recently, the creation of a collection of thermostable Family 6 fungal cellobiohydrolases (Cel6) using structure-guided SCHEMA recombination was reported. The genes encoding the Cel6a from *Humicola insolens, Hypocrea jecorina*, and *Chaetomium thermophilum* were divided into eight blocks and recombined to create new, chimeric Cel6a enzymes. The block boundaries were identified using computational tools that allowed the number of disrupted side-chain contacts to be minimized, relative to the average number of mutations in the resulting chimeric proteins. Based on activity and stability data obtained from the enzymes encoded by the 48 genes that were sampled (from the 6,561 possible chimeric sequences), linear regression models were built to determine how each sequence block contributes to the thermostability of a chimeric Cel6a enzyme. The four stabilizing blocks were introduced in the cellobiohydrolase of *H. jecorina* to create the "HJPlus" chimera 12222332 (described in US Patent Publication No. 2010/0304464-A1, incorporated herein by reference), which is stable for more than 12 hours at 63° C. and is also secreted at relatively high levels in *S. cerevisiae*. In this disclosure, HJPlus was used as the platform for further protein engineering efforts to improve the enzyme properties relevant to optimizing cellulose hydrolysis, most notably thermostability, substrate binding, and cellulose activity. Further improving the thermostability of HJPlus not only pushes the limit of enzyme stability but also allows the discovery of mutations that might not have appeared at lower temperatures because they are not beneficial at lower temperatures. The disclosure also provides a method that allows high throughput screening on microcrystalline cellulose, Avicel, to identify useful mutations.

The disclosure provides modified Family 6 cellulases (Cel6a) that exhibit enhanced activity, thermostability, substrate binding, and/or expression in *S. cerevisiae*. The disclosure also provides genetic constructs that encode the modified Cel6a enzymes and the methods for mutating, deriving, and producing the modified Cel6a enzymes from yeast and fungal expression strains. The disclosure also provides use of the modified Cel6a enzymes in the hydrolysis of cellulose or cellulosic biomass and the production of biofuels from fermentable sugars and alcohols, as well as other industrial applications of cellulases.

As will be described in more detail below, the disclosure is based, at least in part, on the generation and expression of novel enzymes that catalyze the degradation of cellulose. In one embodiment, novel polypeptides that have been engineered/modified to degrade cellulose are provided. Such polypeptides include Cel6a variants that have been altered to include amino acid substitutions at specified residues as well as properties that include increased thermostability compared to wild-type Cel6a enzymes.

While these variants will be described in more detail below, it is understood that polypeptides of the disclosure contain one or more modified amino acids. The presence of modified amino acids are advantageous in, for example, (a) increasing polypeptide in vivo half-life, activity or thermostability, (b) reducing or increasing polypeptide antigenicity, and (c) increasing polypeptide storage stability. Amino acid(s) are modified, for example, co-translationally or post-translationally during recombinant production (e.g., N-linked glycosylation at N--X--S/T motifs during expression in mammalian cells) or modified by synthetic means. Accordingly, A "mutant", "variant" or "modified" protein, polypeptide, enzyme, polynucleotide, gene, or cell, means a protein, polypeptide, enzyme, polynucleotide, gene, or cell, that has been altered or derived, or is in some way different or changed, from a parent protein, polypeptide, enzyme, polynucleotide, gene, or cell. A mutant or modified protein or enzyme is usually, although not necessarily, expressed from a mutant polynucleotide or gene.

"Conservative amino acid substitution" or, simply, "conservative variations" of a particular sequence refers to the replacement of one amino acid, or series of amino acids, with essentially identical amino acid sequences. One of skill will recognize that individual substitutions, deletions or additions which alter, add or delete a single amino acid or a percentage of amino acids in an encoded sequence result in "conservative variations" where the alterations result in the deletion of an amino acid, addition of an amino acid, or substitution of an amino acid with a chemically similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide sequence of the disclosure include substitutions of a percentage, typically less than 10%, of the amino acids of the polypeptide sequence, with a conservatively selected amino acid of the same conservative substitution group. Accordingly, a conservatively substituted variation of a polypeptide of the invention can contain 100, 75, 50, 25, or 10 substitutions with a conservatively substituted variation of the same conservative substitution group.

It is understood that the addition of sequences which do not alter the encoded activity of a nucleic acid molecule, such as the addition of a non-functional or non-coding sequence, is a conservative variation of the basic nucleic acid. The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. As used interchangeably herein a "Cel6a activity", "biological activity of Cel6a" or "functional activity of Cel6a", refers to an activity exerted by a Cel6a, Cel6a polypeptide, or a polypeptide having Cel6a activity on a Cel6a polypeptide substrate, as determined in vitro, according to standard techniques (as described below). Such Cel6a activity can be characterized as the rate of breakdown of cellulose or other organic polymeric sugar composition.

"Conservative variants" are proteins or enzymes in which a given amino acid residue has been changed without altering overall conformation and function of the protein or enzyme, including, but not limited to, replacement of an amino acid with one having similar properties, including polar or nonpolar character, size, shape and charge. Amino acids other than those indicated as conserved may differ in a protein or enzyme so that the percent protein or amino acid sequence similarity between any two proteins of similar function may vary and can be, for example, at least 30%, at least 50%, at least 70%, at least 80%, at least 90%, at least 95%, at least 98% or at least 99%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity. For example, an commonly used on-line algorithm can be found at http://web.expasy.org/sim/ and the default parameters used (e.g., gap open penalty of 12, gap extension penalty of 4 and the comparison Matrix being BLOSUM62). Using the immediately foregoing algorithm "SIM" (Huang et al., Advances in Applied Mathematics, vol. 12 (1991), pp. 337-357), the percent identity between SEQ ID NO:2 and SEQ ID NO:6 is 67.7%.

Non-conservative modifications of a particular polypeptide are those which substitute any amino acid not characterized as a conservative substitution. For example, any substitution which crosses the bounds of the six groups set forth above. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic side chains include lysine (K), arginine (R), histidine (H); acidic side chains include aspartic acid (D), glutamic acid (E); uncharged polar side chains include glycine (G), asparagine (N), glutamine (Q), serine (S), threonine (T), tyrosine (Y), cysteine (C); nonpolar side chains include alanine (A), valine (V), leucine (L), isoleucine (I), proline (P), phenylalanine (F), methionine (M), tryptophan (W); beta-branched side chains include threonine (T), valine (V), isoleucine (I); aromatic side chains include tyrosine (Y), phenylalanine (F), tryptophan (W), histidine (H).

Accordingly, some amino acid residues at specific positions in a polypeptide are "excluded" from conservative amino acid substitutions. Instead, these restricted or "specific" amino acids are generally chosen from a particular group of amino acids or a specific amino acid to be substituted at that position. These amino acid residues can be substituted at a designated position to obtain a modified or variant polypeptide. While some overlap may occur, the members substituted at these specific positions are not "conservative amino acid substitutions" as defined above. In general, these mutations represent non-conservative substitutions at the indicated position in the designated sequence. For example, as described more fully below the substitution at position 14 of, e.g., SEQ ID NO:2 (see FIG. 1), replaces Asn or Gly with Ser. This substitution is generally not considered a "conservative" substitution. Similar substitutions are made throughout the various sequences at the indicated positions in order to modify the activity of the polypeptide.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme. Exemplary parent polynucleotides and polypeptides include, for example, SEQ ID NO:3, 5, and 7 and SEQ ID NO: 4, 6, and 8, respectively.

A "protein" or "polypeptide", which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. A "native" or "wild-type" protein, enzyme, polynucleotide, gene, or cell, means a protein, enzyme, polynucleotide, gene, or cell that occurs in nature. In some embodiments of the disclosure proteins or protein sequences are presented that are not fully "native". For example, in certain aspect of the disclosure the catalytic domains of the respective enzymes are native, but they further comprise a cellulose binding domain and linker from *H. jecorina*, which results in a protein that is not native to, for example, *H. insolens* and *C. thermophilum*.

A polynucleotide, polypeptide, or other component is "isolated" when it is partially or completely separated from components with which it is normally associated (other proteins, nucleic acids, cells, synthetic reagents, etc.). A nucleic acid or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant. For example, an "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

"Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity. For example, the "identity" or "percent identity" with respect to a particular pair of aligned amino acid sequences can refer to the percent amino acid sequence identity that is obtained by ClustalW analysis (version W 1.8 available from European Bioinformatics Institute, Cambridge, UK), counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins" in "Atlas of Protein Sequence and Structure," Vol. 5, Suppl. 3 (ed. M. 0. Dayhoff), pp. 345-352. Natl. Biomed. Res. Found., Washington, D.C. and Henikoff et al. (1992) Proc. Nat'l. Acad. Sci. USA 89: 10915-10919 (each of which is incorporated by reference). The BLOSUM62 matrix (FIG. 10) is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) Nucl. Acids Res. 25: 3389-3402 (incorporated by reference herein), and made available to the public at the National Center for Biotechnology Information (NCBI) Website (www.ncbi.nlm.nih.gov). Optimal alignments, including multiple alignments, can be prepared using, e.g., PSI-BLAST, available through the NCB1 website and described by Altschul et al. (1997) Nucl. Acids Res. 25:3389-3402 (incorporated by reference herein).

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. For example, in SEQ ID NO:2, position 14 is N, position 15 is W, position 16 is S, etc. When a test sequence is optimally aligned with SEQ ID NO:2, a residue in the test sequence that aligns with the W at position 16 is said to "correspond to position 16" of SEQ ID NO:2. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

By "cellulase activity" means an enzyme that is capable of hydrolyzing cellulose. Cellulase refers to a class of enzymes produced by fungi, bacteria, and protozoans that catalyze the hydrolysis of cellulose. However, there are also cellulases produced by other types of organisms such as plants and animals. The EC number for this group of enzymes is EC 3.2.1.4. There are five general types of cellulases based on the type of reaction catalyzed: endo-cellulase; exo-cellulase, within this category there are two main types of exo-cellulases (or cellobiohydrolases, abbreviate CBH)—one type working processively from the reducing end, and one type working processively from the non-reducing end of cellulose; cellobiase or beta-glucosidase hydrolyses; oxidative cellulases; and cellulose phosphorylases that depolymerize cellulose using phosphates instead of water. Most fungal cellulases have two-domains: a catalytic domain and a cellulose binding domain that are connected by a flexible linker. In specific embodiments of the disclosure the cellulase activity is a Cel6a activity. The sequences described herein include, in some instances, both the cellulose binding domain and the catalytic domain or just the catalytic domain. In such instances where only the catalytic domain sequence is provided it will be recognized that a cellulose binding domain (CBD) such as that provided in SEQ ID NO:10, may be functional linked (either as part of the coding sequence or fused later) to the catalytic domain either directly or through a linker.

As used herein a "modified" or "thermostable" Cel6a variant refers to a polypeptide as described in more detail below that comprises at least 67.7% identity (e.g., 67.7, 70, 80, 90, 95, 98, 99% identity) to SEQ ID NO:2, 4, 6, 8, 12, 14, 16, 18, 20, 22, 24, 26 or 28 and which has at least one specific mutation as set forth below. A specific mutation refers to a one or more substitutions at N14, S30, V128, V131, M135, C246, Q277, S293, S317, S406, and/or S413 in HJPlus (SEQ ID NO:2); N38, S54, V151, V154, M158, C269, Q300, S316, S340, S430, and/or S437 in Cel6a enzyme from *Hypocrea jecorina* (SEQ ID NO:4); G37, Q53, V155, V158, Q162, L276, I307, K323, P347, T436, and/or Y443 in Cel6a enzyme from *Humicola insolens* (SEQ ID NO:6); or N38, L54, V155, V158, Q162, L276, I307, R323, S347, T436, and/or Y443 in Cel6a enzyme from *Chaetomium thermophilum* (SEQ ID NO:8), and wherein the modified or thermostable variant comprises increased thermostability or activity compared to a wild-type protein of SEQ ID NO:4, 6, or 8.

Referring to the sequence comparison of various Cel6a polypeptides in FIG. 1, SEQ ID NO:2 includes the amino acid sequence HJplus. SEQ ID NO:4 provides the amino acid sequence of wild-type Cel6a from *Hypocrea jecorina* (including a signal domain residues 1-24) and shares amino acid sequence identity to HJPlus (SEQ ID NO:2). SEQ ID NO:6 includes the amino acid sequence of Cel6a (including a signal domain residues 1-23) from *Humicola insolens*. This wild-type Cel6a shares % amino acid sequence identity to the Cel6a of *Hypocrea jecorina* (SEQ ID NO:4) as well as the HJplus polypeptide of SEQ ID NO:2. SEQ ID NO:8 includes the amino acid sequence of wild-type Cel6a (including a signal domain residues 1-24) from *Chaetomium thermophilum* and shares amino acid sequence identity to SEQ ID NO:2, 4, and 6.

The polypeptides of FIG. 1 (SEQ ID Nos:2, 4, 6, and 8) are closely related to one another and show a high degree of sequence identity. The sequences can be aligned based on the sequence homology. The alignment provided in FIG. 1 identifies "equivalent positions" in the sequences. An equivalent position denotes a position which, on the basis of the alignment of the sequence of the parent polypeptides in question with the "reference" Cel6a amino acid sequence in question (e.g. SEQ ID NO:2) so as to achieve juxtapositioning of amino acid residues which are common to both, corresponds most closely to a particular position in the reference sequence in question. This process can cause gaps or insertions to appear in the sequences. In the alignment of FIG. 1, equivalent positions are shown lined up vertically with one another. For example, position 14 in SEQ ID NO: 2 is equivalent to position 38, 37, and 38 in SEQ ID NO: 4, 6, and 8, respectively.

In one embodiment, the disclosure provides a modified Cel6a enzyme comprising amino acid substitution(s) at one or more residues selected from N14, S30, V128, V131, M135, C246, Q277, S293, S317, S406, and/or S413 in HJPlus (SEQ ID NO:2), wherein the modified Cel6a comprises increased thermostability and cellulase activity. In one specific embodiment, the disclosure encompasses a variant Cel6a enzyme, wherein said enzyme comprises specific amino acid substitution(s) at one or more of the residues N14S, S30F, S30M, V128A, V131E, M135L, C246A, C246G, C246L, C246S, Q277L, S293R, S317P, S317W, S406P, S413F, and/or S413W in HJPlus (SEQ ID NO:2). Accordingly, in various embodiments, isolated or recombinant polypeptides comprising the amino acid sequence set forth in SEQ ID NO:2 having up to 50, 25, 10, or 5 conservative amino acid substitutions excluding specific residues N14, S30, V128, V131, M135, C246, Q277, S293, S317, S406, and/or S413, wherein at least one or more of these specific residues have substitutions selected form the group consisting of N14S, S30F, S30M, V128A, V131E, M135L, C246A, C246G, C246L, C246S, Q277L, S293R, S317P, S317W, S406P, S413F, and/or S413W. In another embodiment, the disclosure provides polypeptides that have at least 80%, 85%, 90%, 95%, 98%, 99% or 100% sequence identity to SEQ ID NO:12, 14, 16, 18, 20, 22, 24, 26, or 28, wherein the polypeptide comprises cellulase activity and has increased thermostability compared to SEQ ID NO:2, 4, 6, or 8.

In one embodiment, the disclosure provides modified Cel6a enzymes derived from amino acid substitution(s) at one or more residues G37, Q53, V155, V158, Q162, L276, I307, K323, P347, T436, and/or Y443 in Cel6a enzyme from *Humicola insolens* (SEQ ID NO:6), from which HJPlus is derived), wherein the modified Cel6a comprises increased thermostability and cellulase activity. The residue position(s) can further be identified by reference to the residues of SEQ ID NO:2 and FIG. 1. In one specific embodiment, the disclosure encompasses a variant Cel6a enzyme, wherein said enzyme comprises amino acid substitution(s) at one or more of the residues G37S, Q53F, Q53M, V155A, V158E, Q162L, L276A, L276G, L276S, I307L, K323R, P347W, T436P, Y443F, and/or Y443W in Cel6a enzyme from *Humicola insolens* (SEQ ID NO:6), from which HJPlus is derived. Accordingly, in various embodiments, isolated or recombinant polypeptides comprising the amino acid sequence set forth in SEQ ID NO:6 having up to 50, 25, 10, or 5 conservative amino acid substitutions excluding specific residues G37, Q53, V155, V158, Q162, L276, I307, K323, P347, T436, and/or Y443, wherein at least one or more of these specific residues have substitutions selected form the group consisting of G37S, Q53F, Q53M, V155A, V158E, Q162L, L276A, L276G, L276S, I307L, K323R, P347W, T436P, Y443F, and/or Y443W. In any of the foregoing embodiments, the polypeptide of SEQ ID NO:6 can lack the leader sequence and comprises amino acid 24-476 of SEQ ID NO:6 and having the foregoing substitutions.

In one embodiment, the disclosure provides a modified Cel6a enzymes derived from amino acid substitution(s) at one or more residues N38, S54, V151, V154, M158, C269, Q300, S316, S340, S430, and/or S437 in Cel6a enzyme from *Hypocrea jecorina* (SEQ ID NO:4), from which HJPlus is derived), wherein the modified Cel6a comprises increased thermostability and cellulase activity. The residue position(s) can further be identified by reference to the residues of SEQ ID NO:2 and FIG. 1. In one specific embodiment, the invention encompasses a variant Cel6a enzyme, wherein said enzyme comprises amino acid substitution(s) at one or more of the residues N38F, S54F, S54M, V151A, V154E, C269A, C269G, C269L, C269S, Q300L, S316R, S340P, S340W, S430P, S437F, and/or S437W in Cel6a enzyme from *Hypocrea jecorina* (SEQ ID NO:4), from which HJPlus is derived. Accordingly, in various embodiments, isolated or recombinant polypeptides comprising the amino acid sequence set forth in SEQ ID NO:4 having up to 50, 25, 10, or 5 conservative amino acid substitutions excluding specific residues N38, S54, V151, V154, M158, C269, Q300, S316, S340, S430, and/or S437, wherein at least one or more of these specific residues have substitutions selected form the group consisting of N38S, S54F, S54M, V151A, V154E, M158L, C269A, C269G, C269L, C269S, Q300L, S316R, S340P, S340W, S430P, S437F, and/or S437W. In any of the foregoing embodiments, the polypeptide of SEQ ID NO:4 can lack the leader sequence and comprises amino acid 25-471 of SEQ ID NO:4 and having the foregoing substitutions.

In one embodiment, the disclosure provides a modified Cel6a enzymes derived from amino acid substitution(s) at one or more residues N38, L54, V155, V158, Q162, L276, I307, R323, S347, T436, and/or Y443 in Cel6a enzyme from *Chaetomium thermophilum* (SEQ ID NO:8), from which HJPlus is derived), wherein the modified Cel6a comprises increased thermostability and cellulase activity. The residue position(s) can further be identified by reference to the residues of SEQ ID NO:2 and FIG. 1. In one specific embodiment, the disclosure encompasses a variant Cel6a enzyme, wherein said enzyme comprises amino acid substitution(s) at one or more of the residues N38S, L54F, L54M, V155A, V158E, Q162L, L276A, L276G, L276S, I307L, S347P, S347W, T436P, Y443F, and/or Y443W in Cel6a enzyme from *Chaetomium thermophilum* (SEQ ID NO:8), from which HJPlus is derived. Accordingly, in various embodiments, isolated or recombinant polypeptides comprising the amino acid sequence set forth in SEQ ID NO:8 having up to 50, 25, 10, or 5 conservative amino acid substitutions excluding specific residues N38, L54, V155, V158, Q162, L276, I307, R323, S347, T436, and/or Y443, wherein at least one or more of these specific residues have substitutions selected form the group consisting of N38S, L54F, L54M, V155A, V158E, Q162L, L276A, L276G, L276S, I307L, S347P, S347W, T436P, Y443F, and/or Y443W. In any of the foregoing embodiments, the polypeptide of SEQ ID NO:8 can lack the leader sequence and comprises amino acid 25-476 of SEQ ID NO:8 and having the foregoing substitutions.

In one embodiment, the disclosure provides modified Family 6 cellulases derived from amino acid substitution at one or more residues corresponding to N14, S30, V128, V131, M135, C246, Q277, S293, S317, S406, and/or S413 of SEQ ID NO:2. The residue position(s) in related Cel6a's can be identified by reference to FIG. 1. In one specific embodiment, the disclosure encompasses a variant Family 6 cellulase, wherein said enzyme comprises amino acid substitution at one or more of the residues corresponding to N14S, S30F, S30M, V128A, V131E, M135L, C246A, C246G, C246L, C246S, Q277L, S293R, S317P, S317W, S406P, S413F, and/or S413W of SEQ ID NO:2 (see, e.g., FIG. 1). Examples of Family 6 cellulases include, but are limited to, *Humicola insolens* Cel6a, *Hypocrea jecorina* Cel6a, *Chaetomium thermophilum* Cel6a, *Phanerochaete chrysosporium* Cel6a, *Thermobifida fusca* Cel6a and Cel6b, *Cellulomonas fimi* Cel6a and Cel6b, *Talaromyces emersonii* CBHII, *Penicillium decumbens* Cel6a, or variants derived from wild-type Family 6 cellulases mentioned above.

In other embodiments of the disclosure polypeptides comprising at least 67.7% or more (e.g., 80%, 85%, 90%, 95%, 98%, or 99%) identity to SEQ ID NO:2 and having any combination of the following amino acids S14, F30, M30, A128, E131, L135, A246, G246, L246, S246, L277, R293, P317, W317, P406, F413, and/or W413 and having Cel6a activity is provided.

In other embodiments of the disclosure polypeptides comprising at least 80%, 85%, 90%, 95%, 98%, or 99% identity to SEQ ID NO:4 and having any combination of the following amino acids S38, F54, M54, A151, E154, L158, A269, G269, L269, S269, L300, R316, P340, W340, P430, F437, and/or W437 and having Cel6a activity is provided.

In other embodiments of the disclosure polypeptides comprising at least 80%, 85%, 90%, 95%, 98%, or 99% identity to SEQ ID NO:6 and having any combination of the following amino acids S37, F53, M53, A155, E158, L162, A276, G276, S276, L307, R323, P347, W347, P436, F443, and/or W443 and having Cel6a activity is provided.

In other embodiments of the disclosure polypeptides comprising at least 80%, 85%, 90%, 95%, 98%, or 99% identity to SEQ ID NO:8 and having any combination of the following amino acids S38, F54, M54, A155, E158, L162, A276, G276, S276, L307, P347, W347, P436, F443, and/or W443 and having Cel6a activity is provided.

In one embodiment, the disclosure relates to a variant derived from an amino acid substitution at residue C246G in a thermostable cellulase of SEQ ID NO:2, or C269G of SEQ ID NO:4, or L276G of SEQ ID NO:6, or L276G of SEQ ID NO:8. The residue position corresponds to the position found in HJPlus of SEQ ID NO:2.

For the purposes of the disclosure, a polypeptide of the disclosure exhibits improved thermostability with respect to a corresponding parent polypeptide if it has a $T_{50}$ which is at least about 5° C., or at least about 9° C. higher than that of the parent cellulase, or for example a cellobiohydrolase having a $T_{50}$ from about 5° C. to about 30° C. higher, or any amount therebetween, or a $T_{50}$ from about 9° C. to about 30° C. higher, or any amount therebetween, when compared to that of the parent cellobiohydrolase. The $T_{50}$ is the temperature at which the modified or the natural enzyme retains 50% of its residual activity after a pre-incubation for 15 minutes and is determined by the assay detailed in Examples below or as known in the art.

A thermostable Cel6a variant of the disclosure comprises an enzyme that has a thermostabililty higher than the wild-type enzyme of SEQ ID NO:4, 6, or 8 by at least 5° C. In one embodiment, the wild-type enzyme has a $T_{50}$ of 70° C. and a thermostabilized variant has an increase in $T_{50}$ of 5° C. or above. In various embodiments described herein, the modified Cel6a enzymes may exhibit enhanced thermostabilities, characterized by a 20-fold increase in half-life at 75° C. and an increase of 7.9° C. in $T_{50}$ value as compared to HJPlus Cel6a of SEQ ID NO:2, or wild-type enzymes comprising SEQ ID NO:4, 6, or 8.

The modified cellobiohydrolases or cellulases of the disclosure may have $T_{50}$ which is about 5° C. to about 30° C. higher than that of a corresponding parent cellobiohydrolase (e.g., SEQ ID NO:2, 4, 6 or 8), or any range therebetween, about 5° C. to about 20° C. higher, or any range therebetween, about 8° C. to about 15° C. higher, or any range therebetween, or from about 9° C. to about 15° C. higher, or any range therebetween. For example, the modified cellulase may have a $T_{50}$ that is at least about 4, 5, 6, 7, 8, 9, 10, 12, 14, 16, 18, 20, 22, 24, 26, 28, or 30° C. higher than that of the corresponding parent cellobiohydrolase.

The disclosure provides Cel6a variants, mutants and chimeras having increased thermostability compared to a wild-type protein consisting of SEQ ID NO:4, 6 or 8. In one embodiment, the thermostable enzyme is derived from amino acid substitution(s) at one or more residues G37, Q53, V155, V158, Q162, L276, I307, K323, P347, T436, and/or Y443 in Cel6a enzyme from *Humicola insolens* (SEQ ID NO:6). In another embodiment, the disclosure encompasses a variant Cel6a enzyme, wherein said thermostable enzyme comprises amino acid substitution(s) at one or more of the residues G37S, Q53F, Q53M, V155A, V158E, Q162L, L276A, L276G, L276S, I307L, K323R, P347W, T436P, Y443F, and/or Y443W in Cel6a enzyme from *Humicola insolens* (SEQ ID NO:6). In various embodiments, isolated or recombinant polypeptides are provided comprising the amino acid sequence set forth in SEQ ID NO:6 having up to 50, 25, 10, or 5 conservative amino acid substitutions excluding specific residues G37, Q53, V155, V158, Q162, L276, I307, K323, P347, T436, and/or Y443, wherein at least one or more of these specific residues have substitutions selected form the group consisting of G37S, Q53F, Q53M, V155A, V158E, Q162L, L276A, L276G, L276S, I307L, K323R, P347W, T436P, Y443F, and/or Y443W are provided. In any of the foregoing embodiments, the polypeptide of SEQ ID NO:6 can lack the leader sequence and comprises amino acid 24-476 of SEQ ID NO:6 and having the foregoing substitutions. In one embodiment, the disclosure provides a thermostable enzyme derived from amino acid substitution(s) at one or more residues N38, S54, V151, V154, M158, C269, Q300, S316, S340, S430, and/or S437 in a Cel6a enzyme from *Hypocrea jecorina* (SEQ ID NO:4). In one specific embodiment, the disclosure encompasses a thermostable variant enzyme, wherein said enzyme comprises amino acid substitution(s) at one or more of the residues N38S, S54F, S54M, V151A, V154E, M158L, C269A, C269G, C269L, C269S, Q300L, S316R, S340P, S340W, S430P, S437F, and/or S437W in Cel6a enzyme from *Hypocrea jecorina* (SEQ ID NO:4). Accordingly, in various embodiments, isolated or recombinant thermostable enyzmes are provided comprising the amino acid sequence set forth in SEQ ID NO:4 having up to 50, 25, 10, or 5 conservative amino acid substitutions excluding specific residues N38, S54, V151, V154, M158, C269, Q300, S316, S340, S430, and/or S437, wherein at least one or more of these specific residues have substitutions selected form the group consisting of N38S, S54F, S54M, V151A, V154E, M158L, C269A, C269G, C269L, C269S, Q300L, S316R, S340P, S340W, S430P, S437F, and/or S437W. In any of the foregoing embodiments, the polypeptide of SEQ ID NO:4 can lack the leader sequence and comprises amino acid 25-471 of SEQ ID NO:4 and having the foregoing substitutions. In one embodiment, the disclosure provides a thermostable enzyme derived from amino acid substitution(s) at one or more residues N38, L54, V155, V158, Q162, L276, I307, R323, S347, T436, and/or Y443 in Cel6a enzyme from *Chaetomium thermophilum* (SEQ ID NO:8). In one embodiment, the disclosure encompasses a thermostable variant enzyme, wherein said enzyme comprises amino acid substitution(s) at one or more of the residues N38S, L54F, L54M, V155A, V158E, Q162L, L276A, L276G, L276S, I307L, S347P, S347W, T436P, Y443F, and/or Y443W in a Cel6a enzyme from *Chaetomium thermophilum* (SEQ ID NO:8). Accordingly, in various embodiments, isolated or recombinant thermostable polypeptides are provided comprising the amino acid sequence set forth in SEQ ID NO:8 having up to 50, 25, 10, or 5 conservative amino acid substitutions excluding specific residues N38, L54, V155, V158, Q162, L276, I307, R323, S347, T436, and/or Y443, wherein at least one or more of these specific residues have substitutions selected form the group consisting of N38S, L54F, L54M, V155A, V158E, Q162L, L276A, L276G, L276S, I307L, S347P, S347W, T436P, Y443F, and/or Y443W. In any of the foregoing embodiments, the polypeptide of SEQ ID NO:8 can lack the leader sequence and comprises amino acid 25-476 of SEQ ID NO:8 and having the foregoing substitutions.

Additional Cel6a family members can be identified by sequence alignment using any of the sequences of SEQ ID NO:2, 4, 6, or 8. These family members can then be modified at corresponding amino acid positions as set forth above. The modified polypeptide may then be assayed for activity as described below at various temperatures and conditions to identify those modifications that introduce a favorable activity.

The variants identified herein can also be used to generate chimeric cellobiohydrolases. For example, SCHEMA has been used previously to create families of hundreds of active β-lactamase and cytochrome P450 enzyme chimeras. SCHEMA uses protein structure data to define boundaries of contiguous amino acid "blocks" which minimize <E>, the library average number of amino acid sidechain contacts that are broken when the blocks are swapped among different parents. It has been shown that the probability that a β-lactamase chimera was folded and active was inversely related to the value of E for that sequence. The RASPP (Recombination as Shortest Path Problem) algorithm was used to identify the block boundaries that minimized <E> relative to the library average number of mutations, <m>. More than 20% of the ~500 unique chimeras characterized from a β-lactamase collection comprised of 8 blocks from 3 parents ($3^8$=6,561 possible sequences) were catalytically active. A similar approach produced a 3-parent, 8-block cytochrome P450 chimera family containing more than 2,300 novel, catalytically active enzymes. Chimeras from these two collections were characterized by high numbers of mutations, 66 and 72 amino acids on average from the closest parent, respectively. SCHEMA/RASPP thus enabled design of chimera families having significant sequence diversity and an appreciable fraction of functional members.

It has also been shown that the thermostabilities of SCHEMA chimeras can be predicted based on sequence-stability data from a small sample of the sequences. Linear regression modeling of thermal inactivation data for 184 cytochrome P450 chimeras showed that SCHEMA blocks made additive contributions to thermostability. More than 300 chimeras were predicted to be thermostable by this model, and all 44 that were tested were more stable than the most stable parent. It was estimated that as few as 35 thermostability measurements could be used to predict the most thermostable chimeras. Furthermore, the thermostable P450 chimeras displayed unique activity and specificity profiles, demonstrating that chimeragenesis can lead to additional useful enzyme properties. Here SCHEMA recombination of CBH II enzymes can generate chimeric cellulases that are active on phosphoric acid swollen cellulose (PASC) at high temperatures, over extended periods of time, and broad ranges of pH.

Descriptions of SCHEMA directed recombination and synthesis of chimeric polypeptides are described in the examples herein, as well as in Otey et al., (2006), PLoS Biol. 4(5):e112; Meyer et al., (2003) Protein Sci., 12:1686-1693; U.S. patent application Ser. No. 12/024,515, filed Feb. 1, 2008; and U.S. patent application Ser. No. 12/027,885, filed Feb. 7, 2008; such references incorporated herein by reference in their entirety.

In other embodiments, the thermostable enzymes described above can be operably linked to a cellulose binding domain (CBD) such as the CBD-linker polypeptide set forth in SEQ ID NO:10. "Fused," "operably linked," and "operably associated" are used interchangeably herein to broadly refer to a chemical or physical coupling of two otherwise distinct domains or peptide segments, wherein each domain or peptide segment when operably linked can provide a functional polypeptide having a desired activity. Domains or peptide segments can be connected through peptide linkers such that they are functional or can be fused through other intermediates or chemical bonds. For example, two domains can be part of the same coding sequence, wherein the polynucleotides are in frame such that the polynucleotide when transcribed encodes a single mRNA that when translated comprises both domains as a single polypeptide. Alternatively, both domains can be separately expressed as individual polypeptides and fused to one another using chemical methods. Typically, the coding domains will be linked "in-frame" either directly of separated by a peptide linker and encoded by a single polynucleotide. Various coding sequences for peptide linkers and peptide are known in the art.

In some embodiments, a polypeptide of the disclosure comprise a substantially pure polypeptide. A "substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure polypeptide composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species.

The disclosure also provides polynucleotide and nucleic acids encoding the polypeptides described herein. "Polynucleotide" or "nucleic acid sequence" refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the disclosure can be ribonucleotides, deoxyribonucleotides, or modified forms of either nucleotide. A polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term polynucleotide encompasses genomic DNA or RNA (depending upon the organism, i.e., RNA genome of viruses), as well as mRNA encoded by the genomic DNA, and cDNA.

The polynucleotides may be operatively linked to one or more heterologous regulatory or control sequences that control gene expression to create a recombinant polynucleotide capable of expressing the polypeptide. Expression constructs containing a heterologous polynucleotide encoding the Cel6a variant can be introduced into appropriate host cells to express the polypeptide.

Given the knowledge of specific sequences of the Cel6a enzymes (see, e.g., SEQ ID NOs:1, 3, 5, and 7), the polynucleotide sequences will be apparent form the amino acid sequence of the disclosure to one of skill in the art. The knowledge of the codons corresponding to various amino acids coupled with the knowledge of the amino acid sequence of the polypeptides allows those skilled in the art to make different polynucleotides encoding the polypeptides of the disclosure. Thus, the disclosure contemplates each and every possible variation of the polynucleotides that could be made by selecting combinations based on possible codon choices, and all such variations are to be considered specifically disclosed for any of the polypeptides described herein.

In some embodiments, the polynucleotides encode the polypeptides described herein but have about 80% or more sequence identity, about 85% or more sequence identity, about 90% or more sequence identity, about 91% or more sequence identity, about 92% or more sequence identity, about 93% or more sequence identity, about 94% or more sequence identity, about 95% or more sequence identity, about 96% or more sequence identity, about 97% or more sequence identity, about 98% or more sequence identity, or about 99% or more sequence identity at the nucleotide level to a reference polynucleotide encoding the Cel6a polypeptides of SEQ ID NO:2, 4, 6, 8, 12, 14, 16, 18, 20, 22, 24, 26, or 28 and encode a polypeptide having cellulase activity and thermostability that is greater than a wild-type Cel6a of SEQ ID NO:4, 6, or 8.

In one embodiment, an isolated polynucleotide of the disclosure comprises at least 80% identity (e.g., 80, 85, 90, 95, 98, 99% identity) to SEQ ID NO:1, 3, 5, 7, 11, 13, 15, 17, 19, 21, 23, 25, or 27 and which encodes a polypeptide of SEQ ID NO:2, 4, 6, 8, 12, 14, 16, 18, 20, 22, 24, 26, or 28 and wherein the polypeptide comprises cellulase activity and has improved thermostability compared to a polypeptide comprising SEQ ID NO:4, 6, or 8. In another embodiment, the disclosure provides a polynucleotide comprising a sequence selected from the group consisting of SEQ ID NO: 11, 13, 15, 17, 19, 21, 23, 25, and 27. In yet another embodiment, the disclosure provides a polynucleotide comprising a sequence that encodes a polypeptide of SEQ ID NO:6 and having one or more substitutions selected from the group consisting of G37S, Q53F, Q53M, V155A, V158E, Q162L, L276A, L276G, L276S, I307L, K323R, P347W, T436P, Y443F, and Y443W. In yet another embodiment, the disclosure provides a polynucleotide comprising a sequence that encodes a polypeptide of SEQ ID NO:4 and having one or more substitutions selected from the group consisting of N38S, S54F, S54M, V151A, V154E, M158L, C269A, C269G, C269S, Q300L, S316R, S340P, S340W, S430P, S437F, and S437W. In yet another embodiment, the disclosure provides a polynucleotide comprising a sequence that encodes a polypeptide of SEQ ID NO:8 and having one or more substitutions selected from the group consisting of N38S, L54F, L54M, V155A, V158E, Q162L, L276A, L276G, L276S, I307L, S347P, S347W, T436P, Y443F, and Y443W.

In some embodiments, the isolated polynucleotides encoding the polypeptides may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2007.

In some embodiments, the polynucleotides are operatively linked to control sequences for the expression of the polynucleotides and/or polypeptides. In some embodiments, the control sequence may be an appropriate promoter sequence, which can be obtained from genes encoding extracellular or intracellular polypeptides, either homologous or heterologous to the host cell. For bacterial host cells, suitable promoters for directing transcription of the nucleic acid constructs of the present disclosure, include the promoters obtained from the *E. coli* lac operon, *Bacillus subtilis* xylA and xylB genes, *Bacillus megatarium* xylose utilization genes (e.g., Rygus et al., (1991) Appl. Microbiol. Biotechnol. 35:594-599; Meinhardt et al., (1989) Appl. Microbiol. Biotechnol. 30:343-350), prokaryotic beta-lactamase gene (Villa-Kamaroff et al., (1978) Proc. Natl Acad. Sci. USA 75: 3727-3731), as well as the tac promoter (DeBoer et al., (1983) Proc. Natl Acad. Sci. USA 80: 21-25). Various suitable promoters are described in "Useful proteins from recombinant bacteria" in Scientific American, 1980, 242:74-94; and in Sambrook et al., supra.

In some embodiments, the control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used.

In some embodiments, the control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used.

In some embodiments, the control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region. Effective signal peptide coding regions for bacterial host cells can be the signal peptide coding regions obtained from the genes for *Bacillus* NClB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, (1993) Microbiol Rev 57: 109-137.

The disclosure is further directed to a recombinant expression vector comprising a polynucleotide encoding the engineered Cel6a polypeptides, and one or more expression regulating regions such as a promoter and a terminator, a replication origin, etc., depending on the type of hosts into which they are to be introduced. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon, may be used.

In some embodiments, the expression vector of the disclosure contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol or tetracycline resistance. Other useful markers will be apparent to the skilled artisan.

In another embodiment, the disclosure provides a host cell comprising a polynucleotide encoding a Cel6a polypeptide, the polynucleotide being operatively linked to one or more control sequences for expression of the polypeptide in the host cell. Host cells for use in expressing the polypeptides encoded by the expression vectors of the disclosure are well known in the art and include, but are not limited to, bacterial cells, such as *E. coli* and *Bacillus megaterium*; eukaryotic cells, such as yeast cells, CHO cells and the like, insect cells such as *Drosophila* S2 and *Spodoptera* Sf9 cells; animal cells such as CHO, COS, BHK, 293, and Bowes melanoma cells; and plant cells. Other suitable host cells will be apparent to the skilled artisan. Appropriate culture mediums and growth conditions for the above-described host cells are well known in the art.

The Cel6a polypeptides of the disclosure can be made by using methods well known in the art. Polynucleotides can be synthesized by recombinant techniques, such as that provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2007. Polynucleotides encoding the enzymes, or the primers for amplification can also be prepared by standard solid-phase methods, according to known synthetic methods, for example using phosphoramidite method described by Beaucage et al., (1981) Tet Lett 22:1859-69, or the method described by Matthes et al., (1984) EMBO J. 3:801-05, e.g., as it is typically practiced in automated synthetic methods. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., Operon Technologies Inc., Alameda, Calif., and many others.

Engineered enzymes expressed in a host cell can be recovered from the cells and or the culture medium using any one or more of the well known techniques for protein purification, including, among others, lysozyme treatment, sonication, filtration, desalting, ultra-centrifugation, chromatography, and affinity separation (e.g., substrate bound antibodies). Suitable solutions for lysing and the high efficiency extraction of proteins from bacteria, such as $E.$ $coli$, are commercially available under the trade name CelLytic BTM from Sigma-Aldrich of St. Louis Mo.

Chromatographic techniques for isolation of the polypeptides include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

As discussed above, the polypeptide can be used in a variety of applications, such as, among others, biofuel generation, cellulose breakdown and the like.

The disclosure also provides a recombinant yeast expressing a Cel6a polypeptide variant as described above. The recombinant organisms of the disclosure are useful for bioethanol production. The engineered strains can be evaluated for cellulose hydrolysis and ethanol production under different conditions such as resting and growth conditions in SDC medium. Both small and large-scale (shaker flask/one liter bioreactor) studies can be performed. In resting cell experiments, cells are grown aerobically using glucose as the carbon source. Cells are then washed and used in cellulose anaerobic hydrolysis. Enzyme activity, hydrolysis products, glucose, and ethanol will be monitored using methods described herein. In studies carried out in a fermentor, a mild agitation can be used to promote mixing of solid cellulose material with cells. Once optimized industrial yeast fermentation process may be used. Different cellulose concentrations can also be used. The rate of glucose generation will be estimated from the experiments and compared to those without the modified Cel6a polypeptides. In studies under growing conditions, the cells will be provided cellulose as the sole carbon source, and other nutrients necessary for growth. Anaerobic conditions are maintained. Cell biomass, enzyme activities, glucose and ethanol are measured.

The disclosure provides yeast strains for direct fermentation of cellulose to ethanol, eliminating the need for use of purified cellulases. The methods and compositions of the disclosure provide abundant, low-cost, agriculture residue to be used as raw material for ethanol production. The increased production of ethanol not only reduces pollution to the environment but also the need for imported petroleum as transportation fuel. Collectively, the benefits from the invention include at least efficient, economical, and environmentally friendly conversion of biomass.

The disclosure also provides purified enzymes (i.e., Cel6a thermostable variants) that can be used for industrial applications. Under such conditions, the enzymes are purified from a yeast or other microorganism engineered to express the thermostable enzyme and the enzymes are then added to a reactor comprising cellulose to be degraded. Other cellulase enzymes (e.g., Cel7a) can be added to the reactor.

The following examples are meant to further explain, but not limited the foregoing disclosure or the appended claims.

EXAMPLES

Strains, plasmids, and oligonucleotides. Strains, plasmid, oligonucleotide, nucleotide and amino acid sequences described herein listed in Tables 1, 2, 3, and 4 below.

TABLE 1

Genotypes of strains disclosed herein

| Species | Strain | Genotype |
|---|---|---|
| E. coli | XL1-blue | recA1 endA1 gyrA96 thi-1 hsdR17 supE44 relA1 lac [F' proAB lacIqZΔM15 Tn10 (Tetr)] |
| S. cerevisiae | YDR483W BY4742 | Mata his3D1 leu2D0 lys2D0 ura3D0 Dkre2, ATCC No. 4014317 |

TABLE 2

Plasmids disclosed herein

| Name | Source or reference |
|---|---|
| pBack | YEp352/PGK91-1-αss |
| pHJPlus | HJPlus gene cloned into the pBack plasmid; it is described in U.S. patent application Ser. No. 12/723,597 |
| p1G6 | 1G6 gene cloned into the pBack plasmid |
| p2B3 | 2B3 gene cloned into the pBack plasmid |
| p3C6P | 3C6P gene cloned into the pBack plasmid |

TABLE 3

Oligonucleotide sequences (shown from 5' to 3') disclosed herein.

| Name | Sequence | Seq ID |
|---|---|---|
| alpha_HomeRe_Lt | CGGGTTATTGTTTATAAATACTACTATTGCCAG | 29 |
| His_HomRe_Rt | GACATGGGAGATCGAATTCAACTCC | 30 |
| S30F_top | GCACATGCGTCTACTTCAACGACTATTACTCC | 31 |

TABLE 3-continued

Oligonucleotide sequences (shown from 5' to 3') disclosed herein.

| Name | Sequence | Seq ID |
|---|---|---|
| S30F_bottom | GGAGTAATAGTCGTTGAAGTAGACGCATGTGC | 32 |
| WT30_top | GCACATGCGTCTACTCCAACGACTATTACTCC | 33 |
| WT30_bottom | GGAGTAATAGTCGTTGGAGTAGACGCATGTGC | 34 |
| V128A_top | GCAGCTAGTGCTGCGGCTGAGGTGCCAAGTTTTATGTGGCTGGATAC | 35 |
| V128A_bottom | GTATCCAGCCACATAAAACTTGGCACCTCAGCCGCAGCACTAGCTGC | 36 |
| V131E_top | GCAGCTAGTGCTGTGGCTGAGGAGCCAAGTTTTATGTGGCTGGATAC | 37 |
| V131E_bottom | GTATCCAGCCACATAAAACTTGGCTCCTCAGCCACAGCACTAGCTGC | 38 |
| M135L_top | GCAGCTAGTGCTGTGGCTGAGGTGCCAAGTTTTTTGTGGCTGGATAC | 39 |
| M135L_bottom | GTATCCAGCCACAAAAAACTTGGCACCTCAGCCACAGCACTAGCTGC | 40 |
| V128A/V131E_top | GCAGCTAGTGCTGCGGCTGAGGAGCCAAGTTTTATGTGGCTGGATAC | 41 |
| V128A/V131E_bottom | GTATCCAGCCACATAAAACTTGGCTCCTCAGCCGCAGCACTAGCTGC | 42 |
| V128A/M135L_top | GCAGCTAGTGCTGCGGCTGAGGTGCCAAGTTTTTTGTGGCTGGATAC | 43 |
| V128A/M135L_bottom | GTATCCAGCCACAAAAAACTTGGCACCTCAGCCGCAGCACTAGCTGC | 44 |
| V131E/M135L_top | GCAGCTAGTGCTGIGGCTGAGGAGCCAAGTTTTTTGTGGCTGGATAC | 45 |
| V131E/M135L_bottom | GTATCCAGCCACAAAAAACTTGGCTCCTCAGCCACAGCACTAGCTGC | 46 |
| 128/131/135_top | GCAGCTAGTGCTGCGGCTGAGGAGCCAAGTTTTTTGTGGCTGGATAC | 47 |
| 128/131/135_bottom | GTATCCAGCCACAAAAAACTTGGCTCCTCAGCCGCAGCACTAGCTGC | 48 |
| WT128/131/135_top | GCAGCTAGTGCTGTGGCTGAGGTGCCAAGTTTTATGTGGCTGGATAC | 49 |
| WT128/131/135_bottom | GTATCCAGCCACATAAAACTTGGCACCTCAGCCACAGCACTAGCTGC | 50 |
| S293R_top | CAAAAATGCCTCAAGACCTAGAGCGCTG | 51 |
| S293R_bottom | CAGCGCTCTAGGTCTTGAGGCATTTTTG | 52 |
| WT293_top | CAAAAATGCCTCAAGTCCTAGAGCGCTG | 53 |
| WT293_bottom | CAGCGCTCTAGGACTTGAGGCATTTTTG | 54 |
| S406P_top | GATGGAACGAGTGATCCTTCTGCTCCAAG | 55 |
| S406P_bottom | CTTGGAGCAGAAGGATCACTCGTTCCATC | 56 |
| WT406_top | GATGGAACGAGTGATTCTTCTGCTCCAAG | 57 |
| WT406_bottom | CTTGGAGCAGAAGAATCACTCGTTCCATC | 58 |
| N14NNK Lt | GGCCAATGTGGTGGCCAGNNKTGGTCGGGTCCGAC | 59 |
| N14 Rt | CTGGCCACCACATTGGCC | 60 |
| S30NNK Lt | CCGGAAGCACATGCGTCTACNNKAACGACTATTACTCCCAGTG | 61 |
| S30 Rt | GTAGACGCATGTGCTTCCGG | 62 |
| V128-NNK Lt | CGTGCCGCAGCTAGTGCTNNKGCTGAGGTGCCAAG | 63 |
| V128 Rt | AGCACTAGCTGCGGCACG | 64 |
| V131NNK Lt | GCAGCTAGTGCTGTGGCTGAGNNKCCAAGTTTTATGTGGCTG | 65 |
| V131 Rt | CTCAGCCACAGCACTAGCTGC | 66 |
| M135NNK Lt | GTGGCTGAGGTGCCAAGTTTTNNKTGGCTGGATACTTTGG | 67 |
| M135 Rt | AAAACTTGGCACCTCAGCCAC | 68 |

TABLE 3-continued

Oligonucleotide sequences (shown from 5' to 3') disclosed herein.

| Name | Sequence | Seq ID |
|---|---|---|
| Q277NNK Lt | GTTGGGTTGGCCAGCAAATNNKGATCCCGCTGCGCAG | 69 |
| Q277 Rt | ATTTGCTGGCCAACCCAAC | 70 |
| S293NNK Lt | GCAAATGTTTACAAAAATGCCTCANNKCCTAGAGCGCTGAGG | 71 |
| S293 Rt | TGAGGCATTTTTGTAAACATTTGC | 72 |
| S317NNK Lt | CTTGGTCAATAGCGAGTCCTCCANNKTACACAAGCCCTAACCC | 73 |
| S317 Rt | GGAGGACTCGCTATTGACCAAG | 74 |
| S406NNK Lt | GGAGAGTCAGATGGAACGAGTGATNNKTCTGCTCCAAGGTTCG | 75 |
| S406 Rt | ATCACTCGTTCCATCTGACTCTCC | 76 |
| S413NNK Lt | GATTCTTCTGCTCCAAGGTTCGATNNKCATTGCGCATTACCAG | 77 |
| S413 Rt | ATCGAACCTTGGAGCAGAAGAATC | 78 |
| W99Y Lt | CTTTGAAGGTGTTCAGCTGTATGCTAATAACTATTATAGATCTGAG | 79 |
| W99Y Rt | CTCAGATCTATAATAGTTATTAGCATACAGCTGAACACCTTCAAAG | 80 |
| N102P Lt | CAGCTGTGGGCTAATCCATATTATAGATCTGAGGTACATAC | 81 |
| N102P Rt | GTATGTACCTCAGATCTATAATATGGATTAGCCCACAGCTG | 82 |
| R122A Lt | GACCCCGCGTTGGCTGCCGCAGCTAGTG | 83 |
| R122A Rt | CACTAGCTGCGGCAGCCAACGCGGGGTC | 84 |
| A124K Lt | GCGTTGCGTGCCAAAGCTAGTGCTGCGG | 85 |
| A124K Rt | CCGCAGCACTAGCTTTGGCACGCAACGC | 86 |
| M146L Lt | GACAAAACCCCCTTATTGGAACAAACGTTGGC | 87 |
| M146L Rt | GCCAACGTTTGTTCCAATAAGGGGGTTTTGTC | 88 |
| I153A Lt | CAAACGTTGGCTGATGCTCGTACTGCGAATAAAAAC | 89 |
| I153A Rt | GTTTTTATTCGCAGTACGAGCATCAGCCAACGTTTG | 90 |
| Y186L Lt | GAGCAACGGGGAGTTGAGCATTGCGGATG | 91 |
| Y186L Rt | CATCCGCAATGCTCAACTCCCCGTTGCTC | 92 |
| C246G Lt | CAGAGTGCTTATCTTGAGGGTATCAATTATGCAGTCAC | 93 |
| C246G Rt | GTGACTGCATAATTGATACCCTCAAGATAAGCACTCTG | 94 |
| V251L Lt | GTGCATCAATTATGCATTGACCCAGTTGAATTTG | 95 |
| V251L Rt | CAAATTCAACTGGGTCAATGCATAATTGATGCAC | 96 |
| S292G Lt | GTTTACAAAAATGCCGGTAGTCCTAGAGCGCTG | 97 |
| S292G Rt | CAGCGCTCTAGGACTACCGGCATTTTTGTAAAC | 98 |
| L297V Lt | CTCAAGTCCTAGAGCGGTTAGGGGTCTTGCAAC | 99 |
| L297V Rt | GTTGCAAGACCCCTAACCGCTCTAGGACTTGAG | 100 |
| P321W Lt | CCACCGTACACAAGCTGGAACCCAAACTACGATG | 101 |
| P321W Rt | CATCGTAGTTTGGGTTCCAGCTTGTGTACGGTGG | 102 |
| F334L Lt | GCATTACATAGAAGCATTGGCTCCTTTGCTTCG | 103 |
| F334L Rt | CGAAGCAAAGGAGCCAATGCTTCTATGTAATGC | 104 |
| P358G Lt | GAAACGGCAAGCAGGGTACAGGGCAGCTAGAATG | 105 |

TABLE 3-continued

Oligonucleotide sequences (shown from 5' to 3') disclosed herein.

| Name | Sequence | Seq ID |
|---|---|---|
| G358G Rt | CATTCTAGCTGCCCTGTACCCTGCTTGCCGTTTC | 106 |
| G360R Lt | CAAGCAGCCGACAAGACAGCTAGAATGGGG | 107 |
| G360R Rt | CCCCATTCTAGCTGTCTTGTCGGCTGCTTG | 108 |
| Q361R Lt | CAGCCGACAGGGAGACTAGAATGGGGGC | 109 |
| Q361R Rt | GCCCCCATTCTAGTCTCCCTGTCGGCTG | 110 |
| T373A Lt | GCAATGTCAAGGGTGCTGGTTTCGGTGTTAGAC | 111 |
| T373A Rt | GTCTAACACCGAAACCAGCACCCTTGACATTGC | 112 |

Media, buffers, and reagents. SD-Ura media: commercially available from MP Biomedicals, contains 20 g/L D-glucose, 1.7 g/L yeast nitrogen base, 5 g/L ammonium sulfate, and 0.8 g/L casamino acids without uracil. YPD media: 10 g/L Bacto yeast extract, 20 g/L Bacto peptone, and 20 g/L D-glucose. Tris-DTT buffer: 390 g/L 1,4-dithiothreitol and 121.1 g/L of Tris base, pH 8.0. Buffer E: 1.2 g/L Tris base, 92.4 g/L sucrose, and 0.2 g/L magnesium chloride, pH 7.4. Buffer A: 20 mM Tris, 100 mM sodium chloride, and 10 mM imidazole, pH 8.0. Buffer B: 20 mM Tris, 100 mM sodium chloride, and 300 mM imidazole, pH 8.0. Somogyi reagent 1: 180 g/L $Na_2SO_4$, 15 g/L Rochelle salt, 30 g/L $Na_2CO_3$, and 20 g/L $NaHCO_3$. Somogyi reagent 2: 180 g/L $Na_2SO_4$ and 12.8 g of anhydrous $CuSO_4$. Nelson reagent: 50 g/L $(NH_4)_2MoO_4$, 1.5 N $H_2SO_4$, and 6 g/L $NaH_2AsO_4$; incubate at 37° C. for 16-24 hours for the formation of the chromogenic compound.

High-efficiency S. cerevisiae transformation. The transformation protocol published by Chao et al. (Nat Protoc, 1(2): 755-768, 2006) was adapted and scaled down to generate libraries with $10^4$ colonies. A colony was used to start a 5 mL YPD culture and grown overnight at 30° C. and 250 rpm. In the morning, the overnight culture was used to inoculate 10 mL of YPD media per transformation to an $OD_{600}$ of 0.1. The YPD culture was grown at 30° C. and 250 rpm until an $OD_{600}$ of 1.5. Once the cells reached the desired absorbance, 100 μL of Tris-DTT buffer per 10 mL of YPD culture was added and incubated at 30° C. and 250 rpm for 15 minutes. The cells were pelleted at 2,500 g for 3 minutes at 4° C., washed with 10 mL of ice-cold buffer E per 10 mL of culture, and again washed with 1 mL of ice-cold buffer E. The cell pellet was resuspended in 50 μL of ice-cold buffer E per transformation. For each transformation, 50 μL competent cells were mixed with 1 μg of DNA in less than 5 μL volume and transferred to an ice-cold 0.2-cm electroporation cuvette. The cells were electroporated at 0.54 kV and 25 μF without a pulse controller and immediately rescued by adding 1 mL of warm (30° C.) YPD media. The cells were incubated at 30° C. and 250 rpm for 1 hour before plating on SD-Ura agar plates and grown at 30° C. for three days.

Heterologous expression in S. cerevisiae in 96-well plates. To express random mutagenesis libraries in S. cerevisiae, the high-efficiency competent cells were used. The competent cells were transformed with 0.5 μg of the linearized vector and 0.5 μg of the error-prone cel6a PCR insert via electroporation and plated on SD-Ura agar plates. The linearized vector and the PCR insert shared regions of homology upstream and downstream of the cel6a gene and were expected to be joined together by homology recombination in S. cerevisiae. Colonies containing mutant Cel6a were randomly selected and inoculated in 50 μL/well of SD-Ura media in 96-well plates. The culture was grown overnight at 30° C., 250 rpm with 80% humidity in orbital shakers. Once the culture in SD-Ura media reached saturation, it was expanded with 350 μL/well of YPD media and grown at 30° C., 250 rpm with 80% humidity for an additional of 48 hours. Both the SD-Ura media and the YPD media in 96-well plates were supplemented with 25 μg/mL of kanamycin to prevent bacterial contamination. The culture was harvested by centrifugation at 5,000×g, 4° C. for 10 minutes, and the supernatant was used for activity assays without further treatment.

High-throughput Cel6a activity assay on avicel. Cel6a enzymes in the culture supernatants were purified by binding to the substrate and washing with 50 mM sodium acetate, pH 5.0, to remove the media. Substrate plates were prepared by pipetting 60 μL of well-agitated 50 mg/mL Avicel solution into 96-well PCR plates. 100 μL of 3-day culture supernatant were added to the substrate plates and incubated at 4° C. for 1.5 hours. Avicel and the bound enzymes were pelleted via centrifugation at 1,000×g, 4° C. and washed three times with 180 μL of 50 mM sodium acetate, pH 5.0. After the wash step, Avicel and the bound enzymes were resuspended in 75 μL of 50 mM sodium acetate, pH 5.0 and incubated at 75° C. for two hours. After the 2-hour incubation, the mixture was cooled immediately to 4° C. and centrifuged at 1,000 g for 10 minutes at 4° C. 50 μL of the supernatant was transferred for determination of the reducing end concentrations using the Nelson-Somogyi microtiter assay described below. 0.1 mM to 2 mM of cellobiose were used as standards.

Detection of reducing sugars. For reducing sugar in the range of 0.15 mM to 2 mM, the Nelson-Somogyi assay was used. Typically, 50 μL of sugar solution was mixed with 40 μL of Somogyi reagent 1 and 10 μL of Somogyi reagent 2 and boiled at 95° C. for 15 minutes. The reaction was subsequently cooled to 4° C. and mixed with 50 μL of Nelson reagent. The reagents were mixed thoroughly to ensure the evolution of $CO_2$ was completed and the maximum color development was achieved. After centrifuging the reagents briefly to remove the $CO_2$ in the solution, the absorbance of the sugar solution at 520 nm was obtained using a Spectra-Max microplate reader with or without cellobiose solution as standard.

Plasmid DNA recovery from S. cerevisiae. The plasmid DNA was recovered from S. cerevisiae using the Zymoprep™ II Yeast Plasmid Miniprep kit (Zymo Research). An aliquot of 200 μL of yeast cells from the library screen were pelleted at 2500 g for 2 minutes. The cell pellet was resuspended in 200 μL of Solution 1 and 5 μL of Zymolase™ provided by the kit and incubated at 37° C. for 1 hour. 200 μL of Solution 2 and 400 μL of Solution 3 provided by the kit were added sequentially and thoroughly mixed. The mixture was centrifuged at 14,000 rpm for 10 minutes in a table-top microcentrifuge. The following purification steps using the Zymo columns were according to the manufacturer's instructions. The plasmid DNA was eluted with 6 μL of Buffer EB provided by the kit. The plasmid DNA was amplified using *E. coli* XL1-blue cells and minipreped using QIAprep Spin Miniprep Kit (Qiagen). The sequence of the plasmid DNA was determined using external sequencing facilities.

Low-efficiency *S. cerevisiae* Ttansformation. *S. cerevisiae* cells were made competent using the Frozen-EZ Yeast Transformation II™ Kit (Zymo Research) for plasmid DNA transformation. A colony was used to start a 5 mL YPD culture and grown overnight at 30° C. and 250 rpm. In the morning, the overnight culture was used to inoculate a new YPD culture to an $OD_{600}$ of 0.1. The YPD culture was grown until the $OD_{600}$ of 1. The cells were pelleted, washed once with EZ 1 solution provided by the kit, and resuspended in EZ 2 solution provided by the kit. The cells were either transformed immediately or stored at −80° C. for future use. 50 μL of the competent cells were diluted with 500 μL of EZ 3 solution provided by the kit. 0.5 μg of plasmid DNA (in less than 5 μL volume) was mixed with 75-500 μL of diluted cells and incubated at 30° C. for 45 minutes, vortexed every 15 minutes. 50-100 μL of transformed cells were spread per SD-Ura agar plate and incubated at 30° C. for three days.

Heterologous expression in *S. cerevisiae* for enzyme purification. Fresh colonies on SD-Ura plates expressing the desired enzymes were inoculated into 5-10 mL SD-Ura medium and grown overnight at 30° C., 250 rpm. The overnight culture was diluted 1:10 with YPD medium in 300-mL Tunair flasks (Shelton Scientific) and grown at 30° C., 250 rpm for 48 hours. Cultures were centrifuged and sterile-filtered using 0.2 μm polyethersulfone membranes, and PMSF (phenylmethylsulfonylfluoride) and sodium azide were supplemented to a final concentration of 100 μM and 0.02%, respectively. Cel6a enzymes in the culture supernatants were purified using HP Ni-NTA Columns (GE Healthcare) in an AKTApurifier™ FPLC system (GE Healthcare), and eluant fractions having elevated absorbance at 280 nm from the baseline were pooled. The enzyme solutions were washed three times using 50 mM sodium acetate, pH 5.0 to remove the imidazole from the elution buffer and concentrated to 500 μL using 20 mL spin columns with 10-kDa PES membranes (Sartorius Stedim Biotech). PMSF and sodium azide were again supplemented to a final concentration of 100 μM and 0.02%, respectively. Purified protein concentrations were determined using the absorbance at 280 nm and the extinction coefficient of the respective protein.

Half-life measurement. The half-life is defined as the time at which an enzyme loses 50% of its activity upon incubation at a specified temperature and other conditions (pH, buffer, etc.). More thermostable enzymes exhibit longer half-lives upon incubation. 40 μL of 50 ng/μL Cel6a enzyme in 50 mM sodium acetate buffer, pH 5.0 were aliquoted into eppendorf tubes and incubated at the specified temperature for a range of times in the tabletop thermal mixer. At each time point, an aliquot/tube of the enzyme was removed and cooled to 4° C. on ice. The range of incubation time was selected such that the half-life would fall approximately in the middle. After the heat inactivation period and cooling, 60 μL of well-agitated 50 mg/mL Avicel solution was added to the enzymes. The solution was subsequently incubated at 50° C. for 2 hours, to obtain a measure the enzyme's residual activity. After the hydrolysis reaction, the solution was cooled to 4° C. and 50 μL of the supernatant was removed for reducing sugar determination along with cellobiose standards using the Nelson-Somogyi assay as described above. The reducing sugar concentrations over the range of heat inactivation periods were determined using the cellobiose standards, and the natural log of the residual activity at each time point was plotted as a function of time using Excel (Microsoft). The data points were fitted using a 1-parameter linear equation with the y-intercept set to zero, and the half-life of the enzyme was determined using the slope of the fitted equation.

$T_{50}$ value measurement. $T_{50}$ is defined as the temperature at which an enzyme loses 50% of its activity during a 15-min heat inactivation period. 40 μL of 50 ng/μL Cel6a enzymes in 50 mM sodium acetate buffer, pH 5.0 were aliquoted into the wells of a 96-well plate and incubated at an elevated temperature gradient in a PCR machine for 15-minutes. The temperature gradient was selected such that the $T_{50}$ value would fall in the middle. After the heat inactivation period, the enzymes were cooled to 4° C. and 60 μL of well-agitated 50 mg/mL Avicel solution were added. The plate was subsequently incubated at 50° C. for 2 hours to measure the residual activity. After the hydrolysis reaction, the solution was cooled to 4° C. and 50 μL of the supernatant was removed for reducing sugar determination along with cellobiose standards using Nelson-Somogyi assay as described above. The reducing sugar concentrations across the temperature gradient were determined using the cellobiose standards and plotted against temperature using SigmaPlot (Systat Sofware Inc). The data points were fitted using 4-parameter sigmoidal curves, and the $T_{50}$ value was determined as the temperature where 50% activity was lost.

Example 1

Thermostabilizing Mutations Discovered by Random Mutagenesis and Screening

The following example illustrates a method for discovering mutations that improve the total activity of Cel6 enzymes at elevated temperatures and also describes the biochemical properties of such improved enzymes.

Random mutagenesis. Plasmid pHJPlus carrying the HJPlus$^{his6}$ gene served as the template for error-prone PCR using forward primer alpha_HomeRe_Lt and reverse primer His_HomRe_Rt. The gene was flanked by the NheI site and the KpnI site in the plasmid pHJPlus. The primers were designed to have regions of homology 85 base-pairs upstream of the NheI site and 65 base-pair downstream of the KpnI site to allow homologous recombination to occur in yeast. The error rates of the libraries were adjusted using different concentrations of manganese chloride in the PCR reaction. Once the error-prone PCR libraries were expressed in yeast, five colonies were randomly selected for sequencing to determine the error-rates. Once the library with the desired mutation rate was identified, roughly 3000 colonies were randomly selected for total secreted cellobiohydrolase activity evaluation at an elevated temperature in the high-throughput assay. The top 1% of the colonies having higher total activities at 75° C. than HJPlus were selected for regrowth and re-evaluation with the activity assay. The total activities from culture supernatants of the top five variants from the rescreen are shown in FIG. 2. The plasmid DNA of the top five variants was recovered, and the region of the Cel6a genes was sequenced. Clone 1G6 was identified as the best-performing variant, with a mutation that encodes for amino acid substitution S317P. Other amino acid substitutions discovered among the top five variants are S30F, V128A, V131E, S293R, and S413F.

Figure 3:
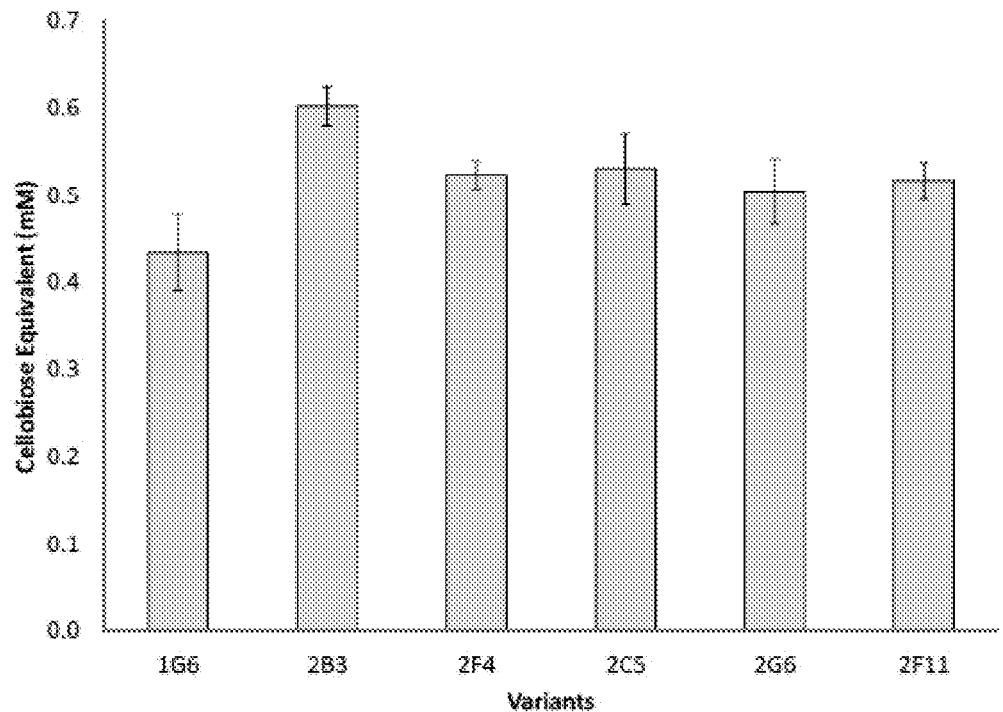
FIG. 3 shows the total activity at 75° C. (measured as cellobiose equivalents released) from 3-day *S. cerevisiae* culture supernatant of cultures expressing 1G6 and the top five variants from the second generation random mutagenesis library.

Plasmid p1G6 carrying the 1G6$^{his6}$ gene served as the template for error-prone PCR for the second generation of mutants. The error-prone PCR libraries were made and characterized as described for the first generation of mutants. Again, roughly 3000 colonies were randomly selected for the total activity evaluation at an elevated temperature in the high-throughput assay. The top 1% of the colonies with higher total activities at 75° C. than 1G6 were selected for regrowth and re-evaluation with the activity assay. The total activities from culture supernatant of the top five variants from the rescreen are shown in FIG. 3. Plasmid DNA from the top five variants was recovered, and the region of Cel6a gene was sequenced. The mutations of the top five clones are listed in Table 4. Clone 2B3 was identified as the best performing variant. It has a mutation that encodes the amino acid substitution. Other mutations discovered among the top five variants are N14S, M135L, S406P, S413P, and S413F.

TABLE 4

List of amino acid substitutions the top five most active variants from generations one and two.

| Generation | Variant | AA substitution | Generation | Variant | AA substitution |
|---|---|---|---|---|---|
| 1 | 1E6 | S30F, V128A | 2 | 2B3 | Q277L |
| 1 | 1E7 | S293R | 2 | 2C5 | N14S, S413P |
| 1 | 1F4 | S413F | 2 | 2F4 | M135L |
| 1 | 1F8 | V131E | 2 | 2F11 | S413F |
| 1 | 1G6 | S317P | 2 | 2G6 | S406P | screening the resulting variants for higher stability. It also describes the biochemical properties of such improved cellobiohydrolase enzymes.

Plasmid p2B3 carrying the 2B3$^{his6}$ gene served as the template for the recombination of the mutations found in the first two generations of random mutagenesis. The amino acid substitutions included in the recombination library can be found in Table 5. Five PCR fragments were generated using the primers listed in Table 6. The fragments were isolated on 1% TAE agarose gels and purified using the QIAquick Gel Extraction Kit (Qiagen). Fragments 1 and 2 were joined together via overlap extension PCR, while fragment 4 and 5 were joined together also via overlap extension PCR. The recombinant library PCR insert was subsequently made using fragment 1+2, 3, and 4+5 using overlap extension PCR.

TABLE 5

List of amino acid mutations included in the recombination library

| Position | Amino Acid in 2B3 | Mutation | Amino acid substitution included in the library |
|---|---|---|---|
| 30 | Ser | Phe | Ser, Phe |
| 128 | Val | Ala | Val, Ala |
| 131 | Val | Glu | Val, Glu |
| 135 | Met | Leu | Met, Leu |
| 293 | Ser | Arg | Ser, Arg |
| 406 | Ser | Pro | Ser, Pro |
| 413 | Ser | — | Ser |

TABLE 6

List of primers used to generate the recombination library

| Fragment | Primers used to clone the amino acid in 2B3 | | Primers used to clone the library mutation | |
|---|---|---|---|---|
| 1 | alpha_HomeRe_Lt | WT30_bottom | alpha_HomeRe_Lt | S30F_bottom |
| 2 | WT30_top | WT128/131/135_bottom | S30F_top | V128A_bottom, V131E_bottom, M135L_bottom, V128A/V131E_bottom, V128A/M135L_bottom, V131E/M135L_bottom, 128/131/135_bottom |
| 3 | WT128/131/135_top | WT293_bottom | V128A_top, V131E_top, M135L_top, V128A/V131E_top, V128A/M135L_top, V131E/M135L_top, 128/131/135_top | S293R_bottom |
| 4 | WT293_top | WT406_bottom | S293R_top | S406P_bottom |
| 5 | WT406_top | His_HomRe_Rt | S406P_top | His_HomRe_Rt |

Example 2

Enhanced Stability by Recombination of Stabilizing Mutations

Figure 4:
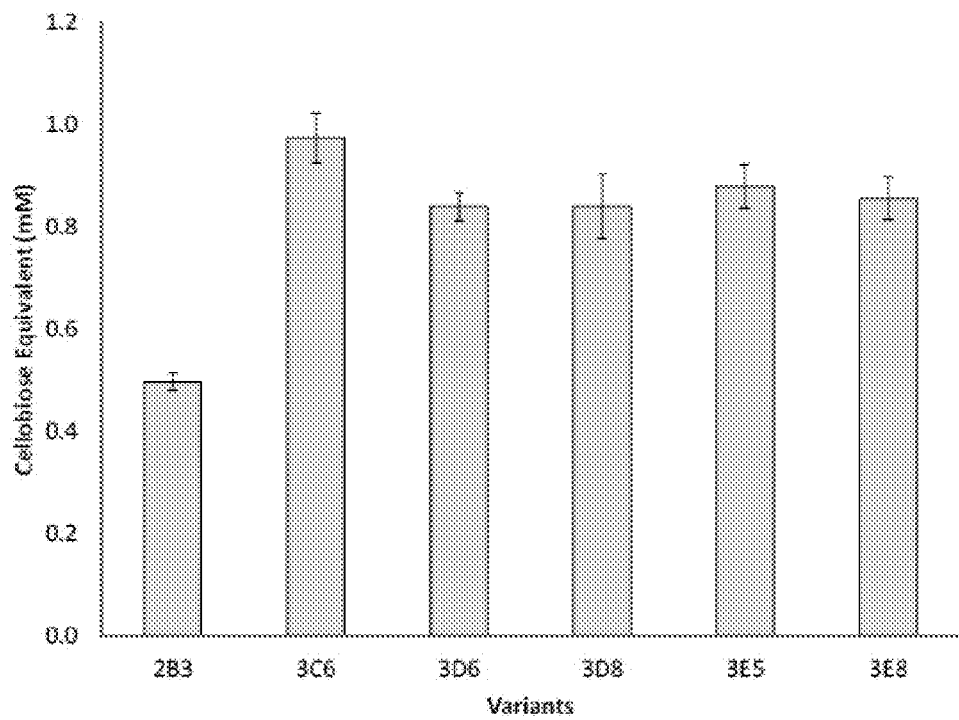
FIG. 4 shows the total activity at 75° C. (measured as cellobiose equivalents released) from 3-day *S. cerevisiae* culture supernatant of cultures expressing 2B3 and the top five variants from the recombination library.
Figure 5:
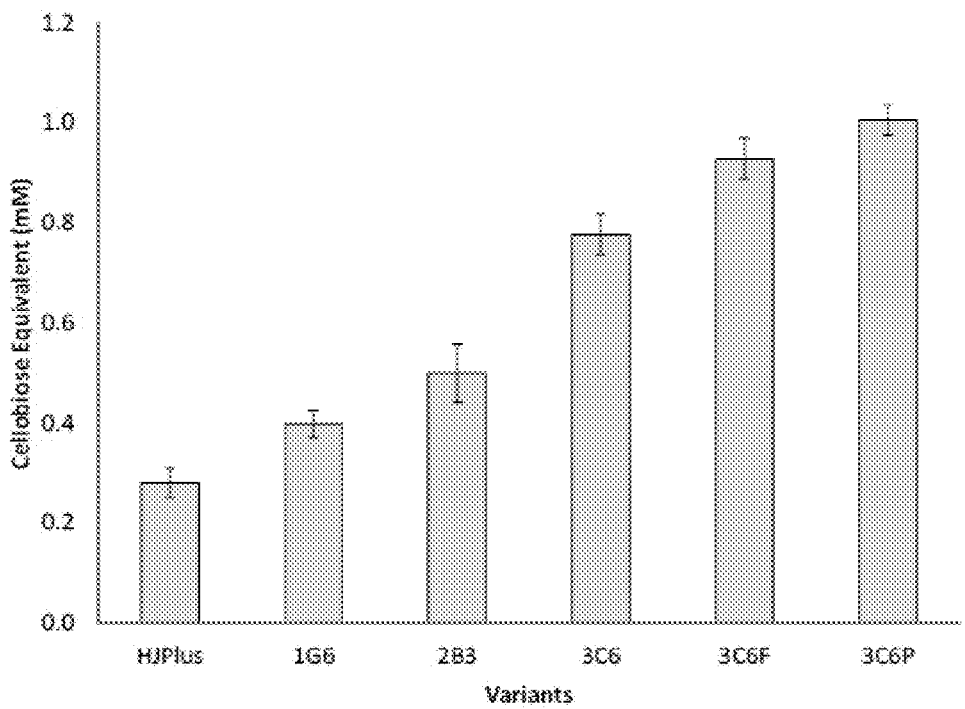
FIG. 5 shows the total activity at 75° C. (measured as cellobiose equivalents released) from 3-day *S. cerevisiae* culture supernatant of cultures expressing HJPlus and the top variant from every generation of random mutagenesis and recombination.

The following example illustrates a method for improving the total activity at elevated temperatures of a cellobiohydrolase by recombining potentially beneficial mutations and The recombinant library was expressed in yeast, and roughly 600 colonies were randomly selected for total activity evaluation at an elevated temperature in the high-throughput assay. The top 6% of the colonies with higher total activities at 75° C. than 2B3 were selected for regrowth and re-evaluation with the activity assay. The total activities of 3-day culture supernatants of the top five variants from the rescreen are shown in FIG. 4. Plasmid DNA was recovered from the top five variants, and the region of Cel6a gene was sequenced. The mutations in the top five variants are listed in Table 7. Variant 3C6 was identified as the best performing variant from the high-throughput screen. Mutation S413F and S413P identified in the previous libraries as beneficial were combined in variant 3C6. The total activities of the variants, as well as that of HJPlus and the best variants from each generation, are shown in FIG. 5. Variant 3C6P was identified to be superior to 3C6F. The best variant 3C6P from the recombinant library contains the mutation S30F, V128A, M135L, Q277L, S317P, S406P, and S413P in the background of HJPlus Cel6a (see, e.g., US Patent Publication No. 2010/0304464-A1, which is incorporated herein by reference).

TABLE 7

The mutations of the top five variants from the recombination library with respect to 2B3

| Variants | Mutation(s) with respect to 2B3 |
|---|---|
| 3C6 | S30F, V128A, M135L, S406P |
| 3D6 | M135L, S406P |
| 3D8 | S30F, V131E |
| 3E5 | V131E, M135L, S293R, S406P |
| 3E8 | S30F, M135L, S406P |

Example 3

Identifying Stabilizing Mutations by Site-saturation Mutagenesis at Key Positions The following example illustrates a method for improving the total activity at elevated temperatures of a cellobiohydrolase and also describes the biochemical properties of such improved cellobiohydrolase enzymes.

Figure 6:
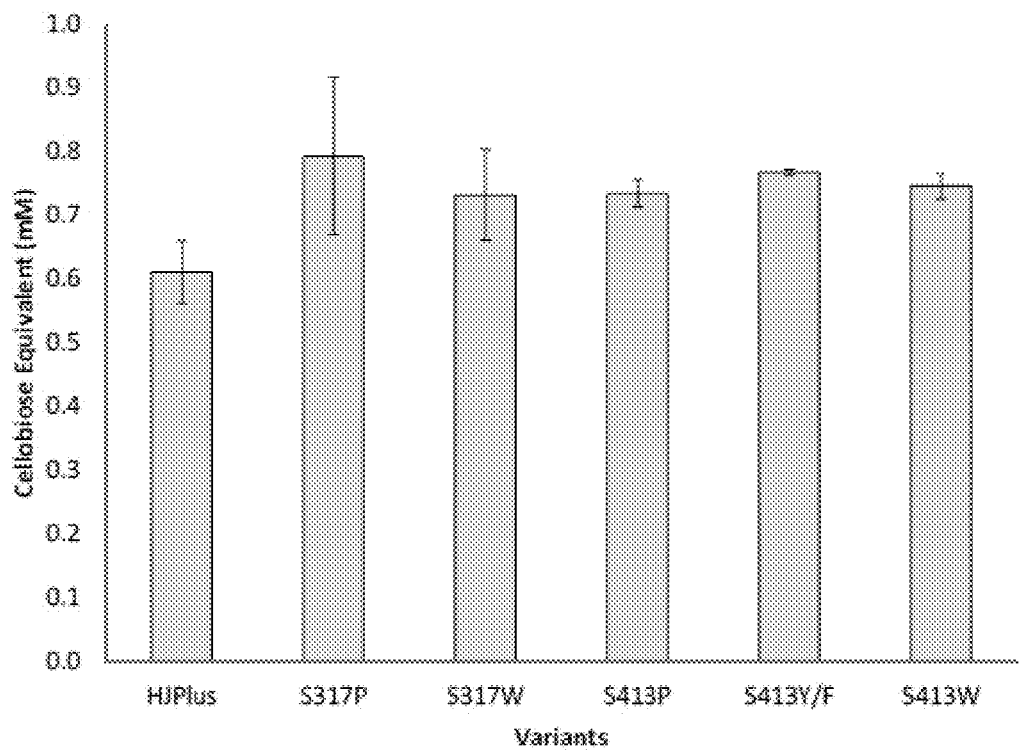
FIG. 6 shows the total activity at 75° C. (measured as cellobiose equivalents released) from 3-day *S. cerevisiae* culture supernatant of cultures expressing the top five variants from the NNK libraries.

The random mutagenesis libraries described above identified 10 amino acid positions as important for improving the total activity of the cellobiohydrolase at elevated temperatures. The amino acid positions are N14, S30, V128, V131, M135, Q277, S293, S317, S406, and S413 based on the sequence of HJPlus. Plasmid pHJPlus carrying the HJPlus$^{his6}$ gene served as the template for the NNK libraries at the beneficial positions described above. The primers used to construct the NNK libraries can be found in Table 8. The NNK libraries were expressed in yeast, and roughly 90 colonies per NNK library were randomly selected for total activity evaluation at an elevated temperature in the high-throughput assay. Colonies showing an increase of 10% or higher in total activity at 75° C. than HJPlus were selected for regrowth and re-evaluation with the activity assay. The plasmid DNA of the top variants at each amino acid position from the rescreen were recovered, and the region of Cel6a gene was sequenced. The beneficial mutations identified from the random mutagenesis libraries were also found as the top variants in the NNK libraries. In other words, the top variants in the NNK libraries identified the same mutations as beneficial as the random mutagenesis libraries. The total activity from 3-day culture supernatant of the top five variants is shown in FIG. 6, with the variants identified by the mutations they contain. Among the top five variants, two new beneficial substitutions were discovered: S317W (SEQ ID NO:11 and 12, polynucleotide and polypeptide, respectively) and S413W (SEQ ID NO:13 and 14, polynucleotide and polypeptide, respectively).

TABLE 8

The primers used to construct the NNK libraries at the ten beneficial positions identified in the random mutagenesis libraries

| Position | Left primer | Right primer |
|---|---|---|
| N14 | N14NNK Lt | N14 Rt |
| S30 | S30NNK Lt | S30 Rt |
| V128 | V128NNK Lt | V128 Rt |
| V131 | V131NNK Lt | V131 Rt |
| M135 | M135NNK Lt | M135 Rt |
| Q277 | Q277NNK Lt | Q277 Rt |
| S293 | S293NNK Lt | S293 Rt |
| S317 | S317NNK Lt | S317 Rt |
| S406 | S406NNK Lt | S406 Rt |
| S413 | S413NNK Lt | S413 Rt |

Example 4

Biochemical Analysis of the Top Variants

The following example describes the biochemical properties of the improved cellobiohydrolase enzymes discovered above.

Figure 7:
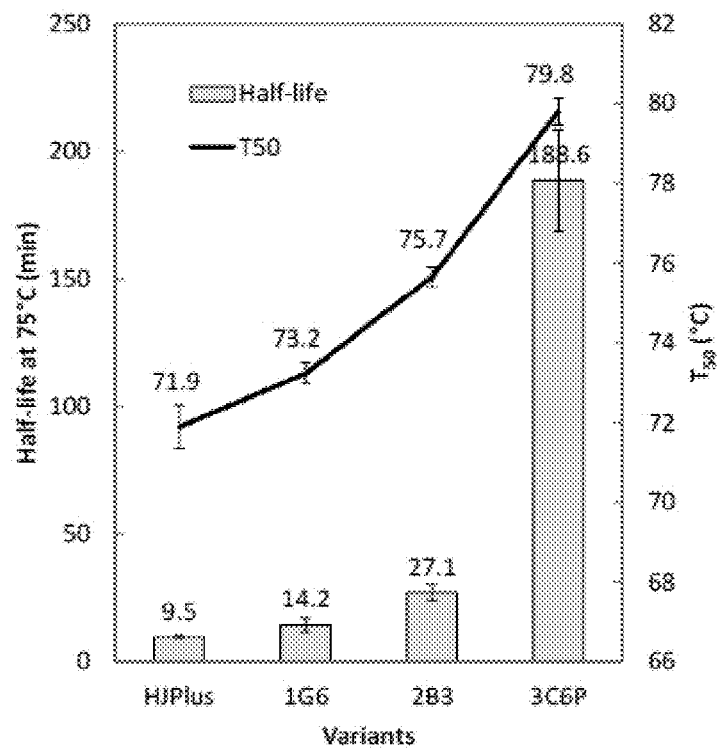
FIG. 7 shows the half-life and $T_{50}$ values for HJPlus and the best variants from each generation of random mutagenesis and recombination.

HJPlus, the top variants from the NNK libraries (S317W and S413W), and the best variant from each generation of the mutagenesis libraries (1F4, 1G6, 2B3, 3C6, and 3C6P), as well as other top variants from the mutagenesis libraries (2F4, and 2G6) were expressed in yeast and purified using the AKTApurifier™ FPLC system as described in the methods section. The half-lives of the purified enzymes were determined at 75° C. in 50 mM sodium acetate buffer, pH 5.0, and the thermal deactivation in 50 mM sodium acetate buffer, pH 5.0 over time was observed to follow a first-order rate equation. As shown in FIG. 7, after three rounds of directed evolution, the half-life of the best variant, 3C6P, at 75° C. increased approximately twenty-fold compared to HJPlus, from 9.5 minutes to 190 minutes.

The $T_{50}$ values of the purified enzymes in 50 mM sodium acetate buffer, pH 5.0 were also determined. The $T_{50}$ values of HJPlus, the top two variants from the NNK libraries (S317W and S413W), and the top variants from the mutagenesis libraries (1F4, 1G6, 2B3, 2F4, 2G6, 3C6, and 3C6P) were measured and summarized in Table 9. The top mutations contributed up to 2.4° C. in the $T_{50}$ values. The $T_{50}$ value of 3C6P increased by 7.9° C., from 71.9° C. to 79.8° C., from HJPlus. The improvements in total activities observed during the high throughput assay at 75° C. can be attributed to a significant increase in the thermostability of the variants.

TABLE 9

The $T_{50}$ values for HJPlus and the top variants from the NNK libraries, the random mutagenesis libraries, and the recombination library

| Variants | T50 (° C.) | Mutation(s) with respect to HJPlus |
|---|---|---|
| HJPlus | 71.9 ± 0.6 | — |
| S317W | 73.6 ± 0.5 | S317W |
| S413W | 74.3 ± 0.3 | S413W |
| 1F4 | 73.0 ± 0.3 | S413F |
| 1G6 | 73.2 ± 0.3 | S317P |
| 2B3 | 75.7 ± 0.3 | Q277L, S317P |
| 2F4 | 75.0 ± 0.2 | M135L, S317P |
| 2G6 | 75.3 ± 0.1 | S317P, S406P |
| 3C6 | 76.9 ± 0.2 | S30F, V128A, M135L, Q277L, S317P, 406P |
| 3C6P | 79.8 ± 0.3 | S30F, V128A, M135L, Q277L, S317P, 406P, S413P |

Example 5

Investigating the pH Dependency of the Top Variants

The following example illustrates a method of identifying residue site(s) for improvements and investigating the pH dependency of the variants at elevated temperatures.

Figure 8:
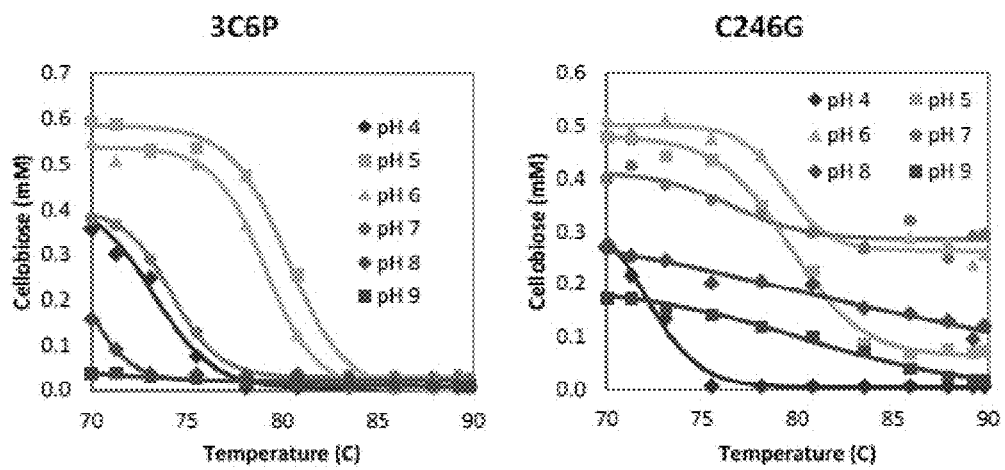
FIG. 8 shows the residual activity of 3C6P and C246G at pH 4 (50 mM sodium citrate), pH 5 (50 mM sodium acetate), and pH 6 through 9 (50 mM sodium phosphate) after 15-minute thermal inactivation; the data were modeled with sigmoidal functions.

At high temperatures, certain amino residues such as cysteine or asparagine are prone to chemical modification or destruction that can lead to irreversible thermal inactivation of the enzyme. To examine the effect of cysteine on the thermal inactivation of Family 6 cellulase, the mutation C246G was introduced into the top variant 3C6P, expressed it in yeast, and purified the Cel6 variant using the AKTApurifier™ FPLC system as described in the methods section. The residual activities of the purified C246G Cel6a enzyme after 15-minute inactivation at 70° C. through 90° C. was examined in 50 mM sodium acetate buffer, pH 5.0, and compared to that of 3C6P. Interestingly, C246G retained a baseline activity after 15-minute incubation at 90° C., where 3C6P was completely inactivated in the same reaction condition. Further examination showed that the effect was pH-dependent. The baseline activity at 90° C. was the most pronounced at pH 6 and pH 7, followed by pH 5 and pH 8, while 3C6P completely deactivated in the same conditions. At pH 7, the C246G variant retained 73% of the activity after 15-minute inactivation at 90° C. (0.29 mM) compared to the residual activity at 70° C. (0.40 mM). At pH 6 where C246G is the most active, the variant retained 51% of the activity after 15-minute inactivation at 90° C. (0.26 mM) compared to the residual activity at 70° C. (0.50 mM). The residual activities of 3C6P and C246G between pH 4 and 9 after 15-minute inactivation at 70° C. through 90° C. are shown in FIG. 8.

Figure 9:
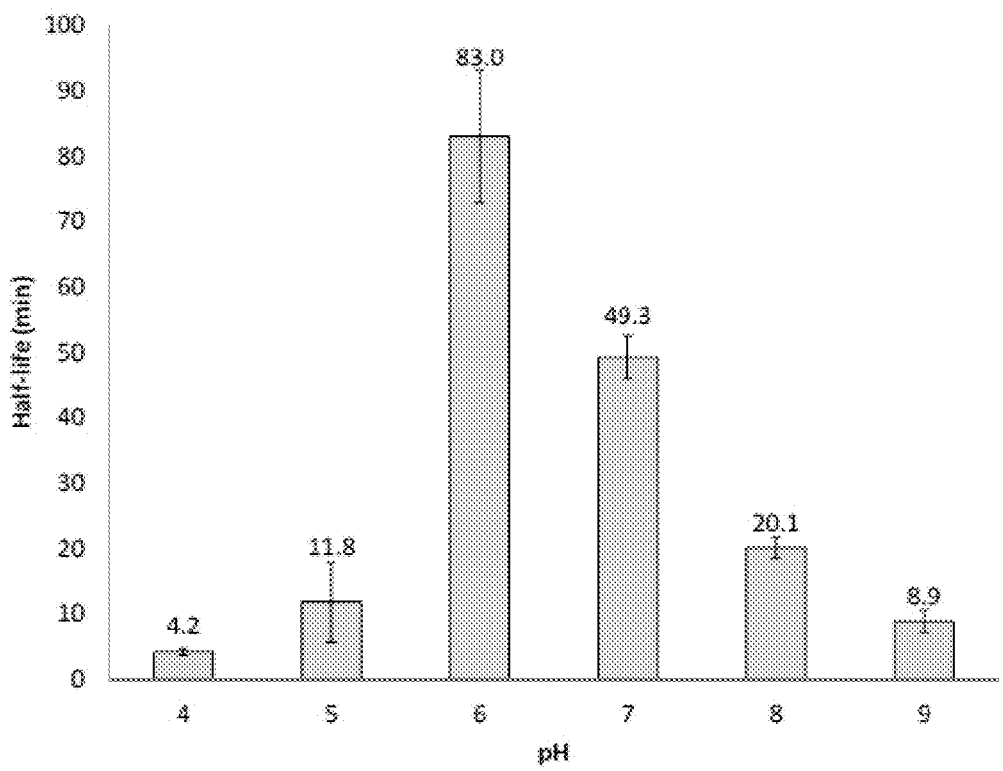
FIG. 9 shows the half-lives of C246G at 90° C. at various pH values (pH 4 (50 mM sodium citrate), pH 5 (50 mM sodium acetate), and pH 6 through 9 (50 mM sodium phosphate)).

The half-life of C246G was determined as well, and the thermal deactivation was observed to follow a first-order rate equation. The half-life of C246G is the longest at pH 6, followed by pH 7, 8, 5, 9, and 4, demonstrating thermostability as well as stability at alkaline conditions. The half-life of C246G was up to 83 minutes at pH 6, while the half-life of 3C6P at 90° C. is less than 5 minutes at various pH. The half-lives of C246G at 90° C. at various pH are summarized in FIG. 9.

Figure 10:
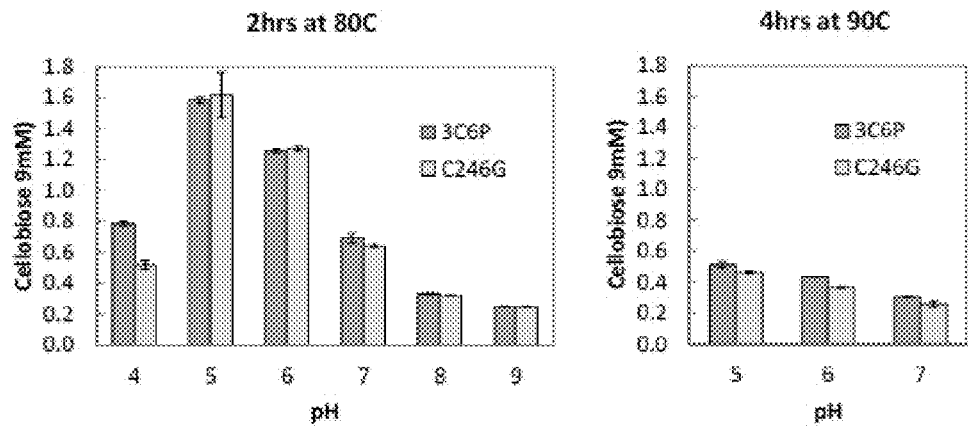
FIG. 10 shows 2-hour activity of 3C6P and C246G at 80° C. and 4-hour activity at 90° C. (measured as cellobiose equivalents released) at various pH conditions (pH 4 (50 mM sodium citrate), pH 5 (50 mM sodium acetate), and pH 6 through 9 (50 mM sodium phosphate)).

In addition to measuring the residual activity of C246G after thermal inactivation in the form of $T_{50}$ values and half-lives at 90° C., the total activities of C246G at various temperatures were measured as well. Specifically, the total activities of 3C6P and C246G after 2 hours of incubation at 80° C. and after 4 hours of incubation at 90° C. were measured and compared across different pHs. As shown in FIG. 10, 3C6P and C246G released the same concentration of cellobiose equivalent across different pHs and at both 80° C. and 90° C. The only exception is the activity of C246G at pH 4 where C246G exhibited slightly lower activity than 3C6P. Combining our observation on the stability of the C246G variant, this shows that the mutation C246G can greatly enhances the stability of a thermostable Family 6 cellulase, without compromising on the activity of the enzyme.

Figure 11:
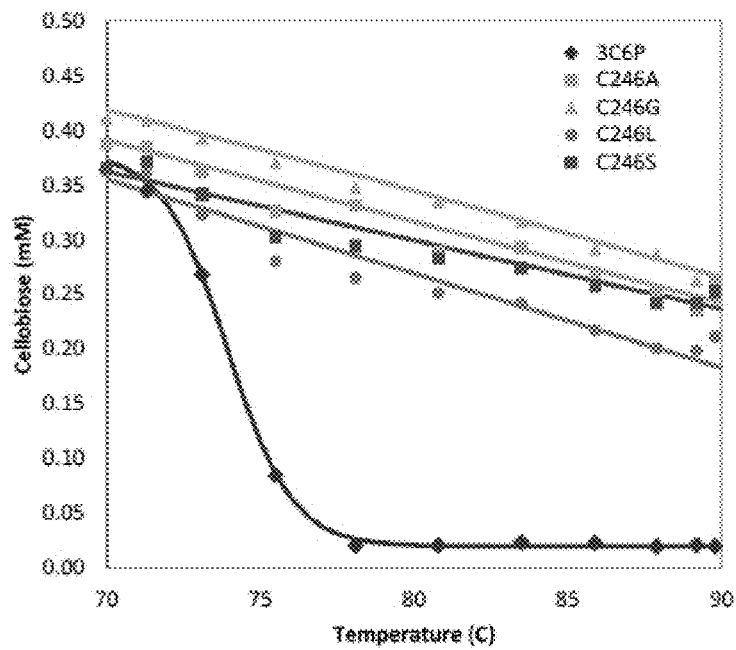
FIG. 11 shows the effects of different mutations at residue C246 on the residual activity of the engineered Cel6s. Purified enzymes were inactivated at 50 mM sodium phosphate, pH 7.0 for 15 minutes before assayed for activities with 30 mg/mL of Avicel. The activity was measured as the amount of cellobiose released after 2-hour incubation at 50° C.

To investigate the mechanism behind the stabilizing effect of the C246G mutation, other amino acid substitution at residue 246 were tested. Three other variants having mutations at residue C246 in the background of 3C6P were constructed and purified: C246S, C246A, and C246L. The activities of the new variants were determined after inactivating them across a temperature gradient between 70° C. and 90° C. for 15 minutes at pH 7.0. As shown in FIG. 11, at pH 7.0 all four variants with mutations at residue C246 exhibited a similar residual activity profile as that of C246G; all four variants retained roughly 35% to 69% activity after heat inactivation.

Example 6

Effect of the pH-dependent Mutation in the Background of *H. jecorina* and *H. insolens* Cel6a The following example described the biochemical properties of the pH-dependent mutation in the background of *H. jecorina* Cel6a and of *H. insolens*.

Figure 12:
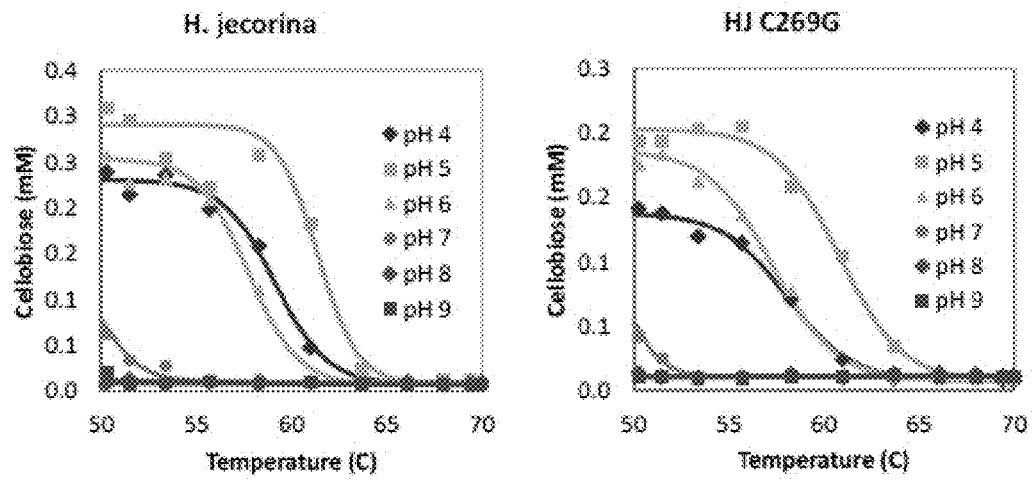
FIG. 12 shows the residual activity of *H. jecorina* Cel6a and HJ C269G at pH 4 (50 mM sodium citrate), pH 5 (50 mM sodium acetate), and pH 6 through 9 (50 mM sodium phosphate) after 15-minute thermal inactivation; the data were modeled with sigmoidal functions.
Figure 13:
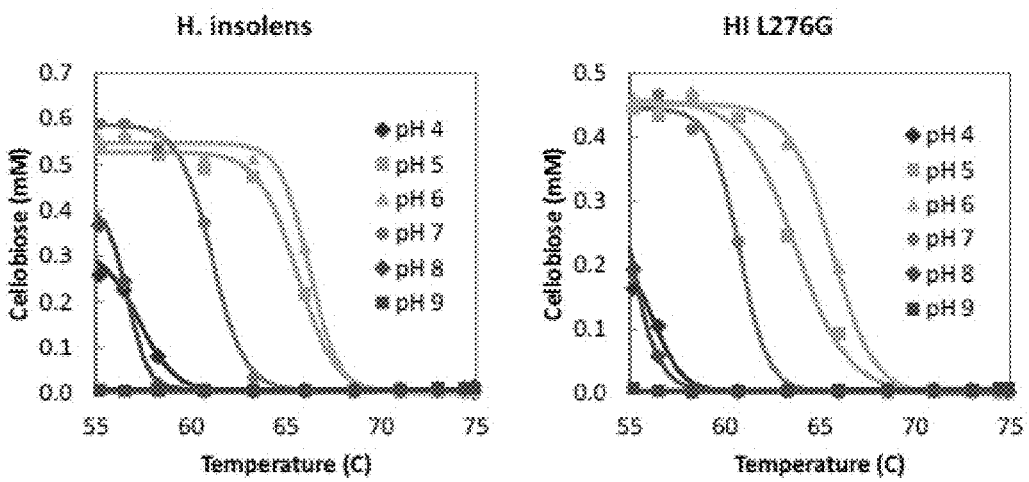
FIG. 13 shows the residual activity of *H. insolens* Cel6a and HI L276G at pH 4 (50 mM sodium citrate), pH 5 (50 mM sodium acetate), and pH 6 through 9 (50 mM sodium phosphate) after 15-minute thermal inactivation; the data were modeled with sigmoidal functions.

Mutation glycine at position 246 (the numbering based on HJPlus) is introduced into the Cel6a enzyme from *H. jecorina*, which has a cysteine at position 269, and into the Cel6a enzyme from *H. insolens*, which has a leucine at position 276. The variants HJ C269G and HI L276G were expressed in yeast and purified using the AKTApurifier™ FPLC system as described in the methods section. The residual activities of the purified HJ C269G and HI L276G after 15-minute inactivation was measured at pH 4 to 9 to examine whether the same retention of baseline activity is observed in other Family 6 cellulases. As shown in FIGS. 12 and 13, the mutation glycine at position 269 and 276 does not stabilize the Cel6a from *H. jecorina* and *H. insolens* as it did in HJPlus, as measured by the residual activities after 15-minute thermal inactivation. This is in stark contrast to the C246G variant (in the background of 3C6P), where the variant retained a high fraction of its residual activity, even as the temperature of thermal inactivation increased to 90° C. As demonstrated here, this is believed to be due to the fact that both HJ C269G and HI L276G contained another free cysteine that is preventing the enzymes from being thermostabilized by the new mutation as it did in C246G.

Example 7

Effect of the Beneficial Mutations in the Background of *H. jecorina* Cel6a

The following example describes the biochemical properties of the beneficial mutations in the background of *H. jecorina* Cel6a.

Figure 14:
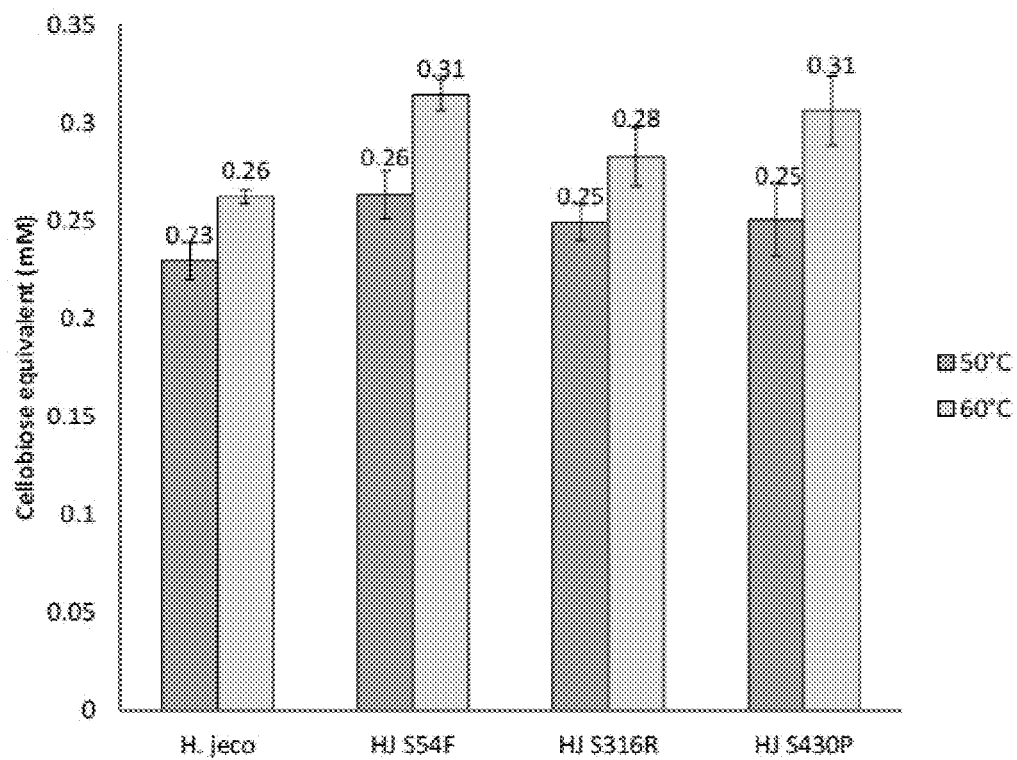
FIG. 14 shows 2-hour activity of *H. jecorina* (HJ) Cel6a, HJ with S54F mutation, HJ with S316R mutation, and HJ with S430P mutation at 50° C. and 60° C. (measured as cellobiose equivalents released) at 50 mM sodium acetate buffer, pH 5.0.

Mutations S54F, S316R, and S430P were introduced into the Cel6a enzyme from *H. jecorina* and expressed in yeast. 4-day yeast culture supernatants were purified using the AKTApurifier™ FPLC system as described in the methods section. The $T_{50}$ values of the purified enzymes in 50 mM sodium acetate buffer, pH 5.0 were determined and summarized in Table 10. The mutations contributed up to 1.7° C. in the $T_{50}$ values, from 60° C. to 61.7° C. This shows that the mutations not only stabilize the HJPlus Cel6a enzyme but also the Cel6a enzyme from its closest parent, *H. jecorina*. The total activities of the enzymes after 2 hours of incubation at 50° C. and 60° C. were measured in 50 mM NaOAc buffer, pH 5.0. As shown in FIG. 14, the improvements in the $T_{50}$ value translated to increases in total activity of the enzyme after 2 hours. The mutants demonstrated an increase up to 13% in total activity at 50° C., from 0.23 mM of cellobiose equivalents to 0.26 mM, and an increase up to 19% in total activity at 60° C., from 0.26 mM to 0.31 mM. As demonstrated here, it is believed that the beneficial mutations discovered in the background of HJPlus are applicable to other cellulases that share high sequence and/or structural homology with HJPlus, including *H. jecoria, H. insolens, C. thermophilum*, from which HJPlus is derived, as well as other Family 6 cellulases not listed here. Sequence homology is defined as high when it is 50% or more compared to the sequence of HJPlus. In addition, structural homology is defined as the ones that share the same structural topologies as HJPlus.

TABLE 10

The T$_{50}$ values for *H. jecorina* (HJ) Cel6a and the beneficial mutations in the background of *H. jecorina* Cel6a

| Variants | T50 (° C.) | Mutation with respect to *H. jecorina* |
|---|---|---|
| *H. jecorina* | 60.0 ± 0.3 | — |
| HJ S54F | 60.4 ± 0.3 | S54F |

TABLE 10-continued

The T$_{50}$ values for *H. jecorina* (HJ) Cel6a and the beneficial mutations in the background of *H. jecorina* Cel6a

| Variants | T50 (° C.) | Mutation with respect to *H. jecorina* |
|---|---|---|
| HJ S316R | 60.1 ± 0.3 | S316R |
| HJ S430P | 61.7 ± 0.1 | S430P |

The foregoing examples are provided to further explain but not limit the disclosure.

What is claimed is:

1. An isolated polypeptide comprising at least 80% sequence identity to SEQ ID NO:2 and having one or more amino acid substitutions at residues selected from the group consisting of N14, S30, V128, V131, M135, C246, Q277, S293, S317, S406, and S413, and wherein the polypeptide has cellulase activity and comprises increased thermostability compared to a wild-type enzyme of SEQ ID NO: 4, 6, or 8.

2. The isolated polypeptide of claim 1, further comprising a cellulose binding domain (CBD) operably linked to the polypeptide.

3. The isolated polypeptide of claim 2, wherein the CBD comprises a sequence of SEQ ID NO:10.

4. The isolated polypeptide of claim 1, wherein the polypeptide comprises one or more substitutions selected from the group consisting of N14S, S30F, S30M, V128A, V131E, M135L, C246A, C246G, C246L, C246S, Q277L, S293R, S317P, S317W, S406P, S413F, and S413W.

5. The isolated polypeptide of claim 1, wherein the polypeptide comprise a sequence that is at least 80% identical to the sequence of SEQ ID NO:12, 14, 16, 18, 20, 22, 24, 26, or 28.

6. The isolated polypeptide of claim 1 comprising the sequence of SEQ ID NO:2 and having substitutions selected from the group consisting of:

(a) one or more substitution at a residue selected from the group consisting of N14, S30, V128, V131, M135, C246, Q277, S293, S317, S406 and any combination thereof; and (b) a substitution at S413 and one or more substitutions at a residue selected from the group consisting of N14, S30, V128, V131, M135, C246, Q277, S293, S317, S406 and any combination thereof.

7. The isolated polypeptide of claim 6, comprising SEQ ID NO:2 and having substitutions selected from the group consisting of:

(a) one or more substitutions selected from the group consisting of N14S, S30F, S30M, V128A, V131E, M135L, C246A, C246G, C246L, C246S, Q277L, S293R, S317P, S317W, and S406P;

(b) S413F and one or more additional substitutions selected from the group consisting of N14S, S30F, S30M, V128A, V131E, M135L, C246A, C246G, C246L, C246S, Q277L, S293R, S317P, S317W, and S406P;

(c) S413P and one or more additional substitutions selected from the group consisting of N14S, S30F, S30M, V128A, V131E, M135L, C246A, C246G, C246L, C246S, Q277L, S293R, S317P, S317W, and S406P; and (d) S413W and one or more additional substitutions selected from the group consisting of N14S, S30F, S30M, V128A, V131E, M135L, C246A, C246G, C246L, C246S, Q277L, S293R, S317P, S317W, and S406P.

8. An isolated polypeptide having a sequence that is 95% identical to a sequence selected from the group consisting of SEQ ID NO:12, 14, 16, 18, 20, 22, 24, 26, and 28, wherein the polypeptide has cellulase activity and is more thermostable than wild-type enzymes having sequence of SEQ ID NO:4, 6, or 8.

9. An enzymatic preparation comprising a polypeptide of claim 1.

10. An enzymatic preparation comprising a polypeptide of claim 1 produced by a recombinant host cell.

11. A method of treating a biomass comprising cellulose, the method comprising contacting the biomass with an enzymatic preparation of claim 9.

\* \* \* \* \*

SEQUENCE LISTING

```
<160> NUMBER OF SEQ ID NOS: 112

<210> SEQ ID NO 1
<211> LENGTH: 1362
<212> TYPE: DNA
<213> ORGANISM: Artificial Sequence
<220> FEATURE:
<223> OTHER INFORMATION: HJPlus Cel6a variant
<220> FEATURE:
<221> NAME/KEY: CDS
<222> LOCATION: (1)..(1362)

<400> SEQUENCE: 1 gct agc tgc tca agc gtc tgg ggc caa tgt ggt ggc cag aat tgg tcg     48
Ala Ser Cys Ser Ser Val Trp Gly Gln Cys Gly Gly Gln Asn Trp Ser
1               5                   10                  15 ggt ccg act tgc tgt gct tcc gga agc aca tgc gtc tac tcc aac gac     96
Gly Pro Thr Cys Cys Ala Ser Gly Ser Thr Cys Val Tyr Ser Asn Asp
            20                  25                  30 tat tac tcc cag tgt ctt ccc ggc gct gca agc tca agc tcg tcc acg    144
Tyr Tyr Ser Gln Cys Leu Pro Gly Ala Ala Ser Ser Ser Ser Ser Thr
        35                  40                  45 cgc gcc gcg tcg acg act tct cga gta tcc ccc aca aca tcc cgg tcg    192
Arg Ala Ala Ser Thr Thr Ser Arg Val Ser Pro Thr Thr Ser Arg Ser
    50                  55                  60 agc tcc gcg acg cct cca cct ggt tct act act acc aga gta cct cca    240
Ser Ser Ala Thr Pro Pro Pro Gly Ser Thr Thr Thr Arg Val Pro Pro
65                  70                  75                  80 gtc gga tcg gga acc gct acg tat tca ggt aac ccc ttt gaa ggt gtt    288
Val Gly Ser Gly Thr Ala Thr Tyr Ser Gly Asn Pro Phe Glu Gly Val
                85                  90                  95 cag ctg tgg gct aat aac tat tat aga tct gag gta cat aca ctg gcc    336
Gln Leu Trp Ala Asn Asn Tyr Tyr Arg Ser Glu Val His Thr Leu Ala
            100                 105                 110 att ccg caa att aca gac ccc gcg ttg cgt gcc gca gct agt gct gtg    384
Ile Pro Gln Ile Thr Asp Pro Ala Leu Arg Ala Ala Ala Ser Ala Val
        115                 120                 125 gct gag gtg cca agt ttt atg tgg ctg gat act ttg gac aaa acc ccc    432
Ala Glu Val Pro Ser Phe Met Trp Leu Asp Thr Leu Asp Lys Thr Pro
    130                 135                 140 tta atg gaa caa acg ttg gct gat ata cgt act gcg aat aaa aac ggc    480
Leu Met Glu Gln Thr Leu Ala Asp Ile Arg Thr Ala Asn Lys Asn Gly
145                 150                 155                 160 ggc aat tat gct gga caa ttt gtg gtt tat gac ctg ccg gat aga gat    528
Gly Asn Tyr Ala Gly Gln Phe Val Val Tyr Asp Leu Pro Asp Arg Asp
                165                 170                 175 tgt gct gca cta gcg agc aac ggg gag tac agc att gcg gat ggc ggt    576
Cys Ala Ala Leu Ala Ser Asn Gly Glu Tyr Ser Ile Ala Asp Gly Gly
            180                 185                 190
```

```
                                                                     -continued gtc gca aag tac aaa aac tat ata gat act atc agg caa ata gtt gtc       624
Val Ala Lys Tyr Lys Asn Tyr Ile Asp Thr Ile Arg Gln Ile Val Val
        195                 200                 205 gaa tac agt gat att cgt acg ctg ctt gta atc gaa ccc gat tcc tta       672
Glu Tyr Ser Asp Ile Arg Thr Leu Leu Val Ile Glu Pro Asp Ser Leu
    210                 215                 220 gcg aac ttg gta aca aat cta ggt act ccg aag tgt gcg aac gcg cag       720
Ala Asn Leu Val Thr Asn Leu Gly Thr Pro Lys Cys Ala Asn Ala Gln
225                 230                 235                 240 agt gct tat ctt gag tgc atc aat tat gca gtc acc cag ttg aat ttg       768
Ser Ala Tyr Leu Glu Cys Ile Asn Tyr Ala Val Thr Gln Leu Asn Leu
            245                 250                 255 cca aac gtt gca atg tat ctt gat gct ggt cat gcc ggg tgg ttg ggt       816
Pro Asn Val Ala Met Tyr Leu Asp Ala Gly His Ala Gly Trp Leu Gly
        260                 265                 270 tgg cca gca aat cag gat ccc gct gcg cag ctg ttt gca aat gtt tac       864
Trp Pro Ala Asn Gln Asp Pro Ala Ala Gln Leu Phe Ala Asn Val Tyr
    275                 280                 285 aaa aat gcc tca agt cct aga gcg ctg agg ggt ctt gca aca aat gtt       912
Lys Asn Ala Ser Ser Pro Arg Ala Leu Arg Gly Leu Ala Thr Asn Val
290                 295                 300 gct aat tac aac gct tgg tca ata gcg agt cct cca tcg tac aca agc       960
Ala Asn Tyr Asn Ala Trp Ser Ile Ala Ser Pro Pro Ser Tyr Thr Ser
305                 310                 315                 320 cct aac cca aac tac gat gag aag cat tac ata gaa gca ttt gct cct      1008
Pro Asn Pro Asn Tyr Asp Glu Lys His Tyr Ile Glu Ala Phe Ala Pro
            325                 330                 335 ttg ctt cgt aac caa ggt ttt gat gca aag ttt atc gtc gat acc gga      1056
Leu Leu Arg Asn Gln Gly Phe Asp Ala Lys Phe Ile Val Asp Thr Gly
        340                 345                 350 aga aac ggc aag cag ccg aca ggg cag cta gaa tgg ggg cac tgg tgc      1104
Arg Asn Gly Lys Gln Pro Thr Gly Gln Leu Glu Trp Gly His Trp Cys
    355                 360                 365 aat gtc aag ggt acg ggt ttc ggt gtt aga ccc acg gct aac act ggg      1152
Asn Val Lys Gly Thr Gly Phe Gly Val Arg Pro Thr Ala Asn Thr Gly
370                 375                 380 cat gag ttg gtt gat gca ttc gtt tgg gta aaa ccc gga gga gag tca      1200
His Glu Leu Val Asp Ala Phe Val Trp Val Lys Pro Gly Gly Glu Ser
385                 390                 395                 400 gat gga acg agt gat tct tct gct cca agg ttc gat tct cat tgc gca      1248
Asp Gly Thr Ser Asp Ser Ser Ala Pro Arg Phe Asp Ser His Cys Ala
            405                 410                 415 tta cca gat gct ttg cag cca gca cct caa gca gga gct tgg ttc caa      1296
Leu Pro Asp Ala Leu Gln Pro Ala Pro Gln Ala Gly Ala Trp Phe Gln
        420                 425                 430 gct tat ttt gta caa tta ctg act aac gcc aat cct agt ttt cta cat      1344
Ala Tyr Phe Val Gln Leu Leu Thr Asn Ala Asn Pro Ser Phe Leu His
    435                 440                 445 cac cat cac cac cat tag                                              1362
His His His His His
        450

<210> SEQ ID NO 2
<211> LENGTH: 453
<212> TYPE: PRT
<213> ORGANISM: Artificial Sequence
<220> FEATURE:
<223> OTHER INFORMATION: Synthetic Construct

<400> SEQUENCE: 2

Ala Ser Cys Ser Ser Val Trp Gly Gln Cys Gly Gly Gln Asn Trp Ser
```

-continued

```
1               5                    10                   15
Gly Pro Thr Cys Cys Ala Ser Gly Ser Thr Cys Val Tyr Ser Asn Asp
             20                  25                  30

Tyr Tyr Ser Gln Cys Leu Pro Gly Ala Ala Ser Ser Ser Ser Ser Thr
             35                  40                  45

Arg Ala Ala Ser Thr Thr Ser Arg Val Ser Pro Thr Thr Ser Arg Ser
50                       55                  60

Ser Ser Ala Thr Pro Pro Pro Gly Ser Thr Thr Thr Arg Val Pro Pro
65                   70                  75                  80

Val Gly Ser Gly Thr Ala Thr Tyr Ser Gly Asn Pro Phe Glu Gly Val
                 85                  90                  95

Gln Leu Trp Ala Asn Asn Tyr Tyr Arg Ser Glu Val His Thr Leu Ala
                 100                 105                 110

Ile Pro Gln Ile Thr Asp Pro Ala Leu Arg Ala Ala Ser Ala Val
                 115                 120                 125

Ala Glu Val Pro Ser Phe Met Trp Leu Asp Thr Leu Asp Lys Thr Pro
             130                 135                 140

Leu Met Glu Gln Thr Leu Ala Asp Ile Arg Thr Ala Asn Lys Asn Gly
145                  150                 155                 160

Gly Asn Tyr Ala Gly Gln Phe Val Val Tyr Asp Leu Pro Asp Arg Asp
                 165                 170                 175

Cys Ala Ala Leu Ala Ser Asn Gly Glu Tyr Ser Ile Ala Asp Gly Gly
             180                 185                 190

Val Ala Lys Tyr Lys Asn Tyr Ile Asp Thr Ile Arg Gln Ile Val Val
             195                 200                 205

Glu Tyr Ser Asp Ile Arg Thr Leu Leu Val Ile Glu Pro Asp Ser Leu
210                  215                 220

Ala Asn Leu Val Thr Asn Leu Gly Thr Pro Lys Cys Ala Asn Ala Gln
225                  230                 235                 240

Ser Ala Tyr Leu Glu Cys Ile Asn Tyr Ala Val Thr Gln Leu Asn Leu
                 245                 250                 255

Pro Asn Val Ala Met Tyr Leu Asp Ala Gly His Ala Gly Trp Leu Gly
             260                 265                 270

Trp Pro Ala Asn Gln Asp Pro Ala Ala Gln Leu Phe Ala Asn Val Tyr
             275                 280                 285

Lys Asn Ala Ser Ser Pro Arg Ala Leu Arg Gly Leu Ala Thr Asn Val
             290                 295                 300

Ala Asn Tyr Asn Ala Trp Ser Ile Ala Ser Pro Pro Ser Tyr Thr Ser
305                  310                 315                 320

Pro Asn Pro Asn Tyr Asp Glu Lys His Tyr Ile Glu Ala Phe Ala Pro
                 325                 330                 335

Leu Leu Arg Asn Gln Gly Phe Asp Ala Lys Phe Ile Val Asp Thr Gly
             340                 345                 350

Arg Asn Gly Lys Gln Pro Thr Gly Gln Leu Glu Trp Gly His Trp Cys
             355                 360                 365

Asn Val Lys Gly Thr Gly Phe Gly Val Arg Pro Thr Ala Asn Thr Gly
             370                 375                 380

His Glu Leu Val Asp Ala Phe Val Trp Val Lys Pro Gly Gly Glu Ser
385                  390                 395                 400

Asp Gly Thr Ser Asp Ser Ser Ala Pro Arg Phe Asp Ser His Cys Ala
                 405                 410                 415

Leu Pro Asp Ala Leu Gln Pro Ala Pro Gln Ala Gly Ala Trp Phe Gln
             420                 425                 430
```

Ala Tyr Phe Val Gln Leu Leu Thr Asn Ala Asn Pro Ser Phe Leu His
        435                 440                 445

His His His His His
    450

<210> SEQ ID NO 3
<211> LENGTH: 1416
<212> TYPE: DNA
<213> ORGANISM: Hypocrea jecorina
<220> FEATURE:
<221> NAME/KEY: CDS
<222> LOCATION: (1)..(1416)

<400> SEQUENCE: 3

```
atg att gtc ggc att ctc acc acg ctg gct acg ctg gcc aca ctc gca      48
Met Ile Val Gly Ile Leu Thr Thr Leu Ala Thr Leu Ala Thr Leu Ala
1               5                   10                  15 gct agt gtg cct cta gag gag cgg caa gct tgc tca agc gtc tgg ggc      96
Ala Ser Val Pro Leu Glu Glu Arg Gln Ala Cys Ser Ser Val Trp Gly
                20                  25                  30 caa tgt ggt ggc cag aat tgg tcg ggt ccg act tgc tgt gct tcc gga     144
Gln Cys Gly Gly Gln Asn Trp Ser Gly Pro Thr Cys Cys Ala Ser Gly
            35                  40                  45 agc aca tgc gtc tac tcc aac gac tat tac tcc cag tgt ctt ccc ggc     192
Ser Thr Cys Val Tyr Ser Asn Asp Tyr Tyr Ser Gln Cys Leu Pro Gly
        50                  55                  60 gct gca agc tca agc tcg tcc acg cgc gcc gcg tcg acg act tct cga     240
Ala Ala Ser Ser Ser Ser Ser Thr Arg Ala Ala Ser Thr Thr Ser Arg
65                  70                  75                  80 gta tcc ccc aca aca tcc cgg tcg agc tcc gcg acg cct cca cct ggt     288
Val Ser Pro Thr Thr Ser Arg Ser Ser Ser Ala Thr Pro Pro Pro Gly
                85                  90                  95 tct act act acc aga gta cct cca gtc gga tcg gga acc gct acg tat     336
Ser Thr Thr Thr Arg Val Pro Pro Val Gly Ser Gly Thr Ala Thr Tyr
            100                 105                 110 tca ggc aac cct ttt gtt ggg gtc act cct tgg gcc aat gca tat tac     384
Ser Gly Asn Pro Phe Val Gly Val Thr Pro Trp Ala Asn Ala Tyr Tyr
        115                 120                 125 gcc tct gaa gtt agc agc ctc gct att cct agc ttg act gga gcc atg     432
Ala Ser Glu Val Ser Ser Leu Ala Ile Pro Ser Leu Thr Gly Ala Met
    130                 135                 140 gcc act gct gca gca gct gtc gca aag gtt ccc tct ttt atg tgg cta     480
Ala Thr Ala Ala Ala Ala Val Ala Lys Val Pro Ser Phe Met Trp Leu
145                 150                 155                 160 gat act ctt gac aag acc cct ctc atg gag caa acc ttg gcc gac atc     528
Asp Thr Leu Asp Lys Thr Pro Leu Met Glu Gln Thr Leu Ala Asp Ile
                165                 170                 175 cgc acc gcc aac aag aat ggt ggt aac tat gcc gga cag ttt gtg gtg     576
Arg Thr Ala Asn Lys Asn Gly Gly Asn Tyr Ala Gly Gln Phe Val Val
            180                 185                 190 tat gac ttg ccg gat cgc gat tgc gct gcc ctt gcc tcg aat ggc gaa     624
Tyr Asp Leu Pro Asp Arg Asp Cys Ala Ala Leu Ala Ser Asn Gly Glu
        195                 200                 205 tac tct att gcc gat ggt ggc gtc gcc aaa tat aag aac tat atc gac     672
Tyr Ser Ile Ala Asp Gly Gly Val Ala Lys Tyr Lys Asn Tyr Ile Asp
    210                 215                 220 acc att cgt caa att gtc gtg gaa tat tcc gat atc cgg acc ctc ctg     720
Thr Ile Arg Gln Ile Val Val Glu Tyr Ser Asp Ile Arg Thr Leu Leu
225                 230                 235                 240 gtt att gag cct gac tct ctt gcc aac ctg gtg acc aac ctc ggt act     768
```

```
                Val Ile Glu Pro Asp Ser Leu Ala Asn Leu Val Thr Asn Leu Gly Thr
                                245                 250                 255 cca aag tgt gcc aat gct cag tca gcc tac ctt gag tgc atc aac tac            816
Pro Lys Cys Ala Asn Ala Gln Ser Ala Tyr Leu Glu Cys Ile Asn Tyr
            260                 265                 270 gcc gtc aca cag ctg aac ctt cca aat gtt gcg atg tat ttg gac gct            864
Ala Val Thr Gln Leu Asn Leu Pro Asn Val Ala Met Tyr Leu Asp Ala
        275                 280                 285 ggc cat gca gga tgg ctt ggc tgg ccg gca aac caa gac ccg gcc gct            912
Gly His Ala Gly Trp Leu Gly Trp Pro Ala Asn Gln Asp Pro Ala Ala
    290                 295                 300 cag cta ttt gca aat gtt tac aag aat gca tcg tct ccg aga gct ctt            960
Gln Leu Phe Ala Asn Val Tyr Lys Asn Ala Ser Ser Pro Arg Ala Leu
305                 310                 315                 320 cgc gga ttg gca acc aat gtc gcc aac tac aac ggg tgg aac att acc           1008
Arg Gly Leu Ala Thr Asn Val Ala Asn Tyr Asn Gly Trp Asn Ile Thr
                325                 330                 335 agc ccc cca tcg tac acg caa ggc aac gct gtc tac aac gag aag ctg           1056
Ser Pro Pro Ser Tyr Thr Gln Gly Asn Ala Val Tyr Asn Glu Lys Leu
            340                 345                 350 tac atc cac gct att gga cct ctt ctt gcc aat cac ggc tgg tcc aac           1104
Tyr Ile His Ala Ile Gly Pro Leu Leu Ala Asn His Gly Trp Ser Asn
        355                 360                 365 gcc ttc ttc atc act gat caa ggt cga tcg gga aag cag cct acc gga           1152
Ala Phe Phe Ile Thr Asp Gln Gly Arg Ser Gly Lys Gln Pro Thr Gly
    370                 375                 380 cag caa cag tgg gga gac tgg tgc aat gtg acc ggc acc gga ttt ggt           1200
Gln Gln Gln Trp Gly Asp Trp Cys Asn Val Thr Gly Thr Gly Phe Gly
385                 390                 395                 400 att cgc cca tcc gca aac act ggg gac tcg ttg ctg gat tcg ttt gtc           1248
Ile Arg Pro Ser Ala Asn Thr Gly Asp Ser Leu Leu Asp Ser Phe Val
                405                 410                 415 tgg gtc aag cca ggc ggc gag tgt gac ggc acc agc gac agc agt gcg           1296
Trp Val Lys Pro Gly Gly Glu Cys Asp Gly Thr Ser Asp Ser Ser Ala
            420                 425                 430 cca cga ttt gac tcc cac tgt gcg ctc cca gat gcc ttg caa ccg gcg           1344
Pro Arg Phe Asp Ser His Cys Ala Leu Pro Asp Ala Leu Gln Pro Ala
        435                 440                 445 cct caa gct ggt gct tgg ttc caa gcc tac ttt gtg cag ctt ctc aca           1392
Pro Gln Ala Gly Ala Trp Phe Gln Ala Tyr Phe Val Gln Leu Leu Thr
    450                 455                 460 aac gca aac cca tcg ttc ctg taa                                           1416
Asn Ala Asn Pro Ser Phe Leu
465                 470

<210> SEQ ID NO 4
<211> LENGTH: 471
<212> TYPE: PRT
<213> ORGANISM: Hypocrea jecorina

<400> SEQUENCE: 4

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60
```

-continued

```
Ala Ala Ser Ser Ser Ser Thr Arg Ala Ala Ser Thr Thr Ser Arg
 65                  70                  75                  80

Val Ser Pro Thr Thr Ser Arg Ser Ser Ala Thr Pro Pro Gly
             85                  90                  95

Ser Thr Thr Thr Arg Val Pro Val Gly Ser Gly Thr Ala Thr Tyr
                100                 105                 110

Ser Gly Asn Pro Phe Val Gly Val Thr Pro Trp Ala Asn Ala Tyr Tyr
            115                 120                 125

Ala Ser Glu Val Ser Ser Leu Ala Ile Pro Ser Leu Thr Gly Ala Met
        130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
                180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Thr Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470
```

```
<210> SEQ ID NO 5
<211> LENGTH: 1431
<212> TYPE: DNA
<213> ORGANISM: Humicola insolens
<220> FEATURE:
<221> NAME/KEY: CDS
<222> LOCATION: (1)..(1431)

<400> SEQUENCE: 5 atg gcc aag ttc ttc ctt act gct gcc ttt gcg gct gcc gct ctc gcc      48
Met Ala Lys Phe Phe Leu Thr Ala Ala Phe Ala Ala Ala Ala Leu Ala
1               5                   10                  15 gct ccc gtt gtt gag gag cgc cag aac tgt gcc ccg act tgg ggc cag      96
Ala Pro Val Val Glu Glu Arg Gln Asn Cys Ala Pro Thr Trp Gly Gln
            20                  25                  30 tgc ggt ggc atc ggc ttc aat ggc ccg act tgc tgc cag tct ggt agc     144
Cys Gly Gly Ile Gly Phe Asn Gly Pro Thr Cys Cys Gln Ser Gly Ser
        35                  40                  45 acc tgc gtg aag cag aac gac tgg tac tcc cag tgc ttg ccc ggt agc     192
Thr Cys Val Lys Gln Asn Asp Trp Tyr Ser Gln Cys Leu Pro Gly Ser
    50                  55                  60 cag gtc acc acg acc tcg act acg tcg act tcg agc tcg tcg acc acc     240
Gln Val Thr Thr Thr Ser Thr Thr Ser Thr Ser Ser Ser Ser Thr Thr
65                  70                  75                  80 tcc cgg gcc acc tcg acc acc agg acc ggt ggt gtg acc tcg atc acc     288
Ser Arg Ala Thr Ser Thr Thr Arg Thr Gly Gly Val Thr Ser Ile Thr
                85                  90                  95 act gct ccc acc cgc acc gtc acc atc cct ggc ggt gcc acc acc acg     336
Thr Ala Pro Thr Arg Thr Val Thr Ile Pro Gly Gly Ala Thr Thr Thr
            100                 105                 110 gcc agc tac aac ggc aac ccc ttc gag ggt gtc cag ctc tgg gcc aac     384
Ala Ser Tyr Asn Gly Asn Pro Phe Glu Gly Val Gln Leu Trp Ala Asn
        115                 120                 125 aac tac tac cgc tct gag gtc cac acc ctc gcc att cct cag atc acc     432
Asn Tyr Tyr Arg Ser Glu Val His Thr Leu Ala Ile Pro Gln Ile Thr
    130                 135                 140 gac cct gcc ttg agg gct gcg gcc tcg gcc gtc gct gag gtc ccg agc     480
Asp Pro Ala Leu Arg Ala Ala Ala Ser Ala Val Ala Glu Val Pro Ser
145                 150                 155                 160 ttc cag tgg ctc gac cgc aac gtc acg gtc gac acc ctg ctc gtc gag     528
Phe Gln Trp Leu Asp Arg Asn Val Thr Val Asp Thr Leu Leu Val Glu
                165                 170                 175 acc ctc tct gag atc cgc gcc gcg aac cag gcg ggc gcg aac ccc ccg     576
Thr Leu Ser Glu Ile Arg Ala Ala Asn Gln Ala Gly Ala Asn Pro Pro
            180                 185                 190 tat gcc gcc cag atc gtc gtt tac gac ctt cct gac cgc gac tgc gct     624
Tyr Ala Ala Gln Ile Val Val Tyr Asp Leu Pro Asp Arg Asp Cys Ala
        195                 200                 205 gcc gcg gct tcg aac ggc gag tgg gcg atc gcc aac aac ggc gcc aac     672
Ala Ala Ala Ser Asn Gly Glu Trp Ala Ile Ala Asn Asn Gly Ala Asn
    210                 215                 220 aac tac aag gga tac atc aac cgg atc cgc gag att ctc att tcg ttc     720
Asn Tyr Lys Gly Tyr Ile Asn Arg Ile Arg Glu Ile Leu Ile Ser Phe
225                 230                 235                 240 tcg gat gtc cgc acg att ctg gtt atc gag ccc gac tcg ctg gcc aac     768
Ser Asp Val Arg Thr Ile Leu Val Ile Glu Pro Asp Ser Leu Ala Asn
                245                 250                 255 atg gtc acc aac atg aac gtc gcc aag tgc agc ggt gcc gcc tcg acc     816
Met Val Thr Asn Met Asn Val Ala Lys Cys Ser Gly Ala Ala Ser Thr
            260                 265                 270 tac cgc gag ttg acc atc tat gcc ctc aag cag ctc gac ctc ccg cac     864
```

```
Tyr Arg Glu Leu Thr Ile Tyr Ala Leu Lys Gln Leu Asp Leu Pro His
            275                 280                 285 gtc gcc atg tac atg gac gcc ggc cac gct ggc tgg ctt ggc tgg ccc        912
Val Ala Met Tyr Met Asp Ala Gly His Ala Gly Trp Leu Gly Trp Pro
        290                 295                 300 gcc aac atc cag ccc gct gct gag ctc ttc gcc aag atc tac gag gat        960
Ala Asn Ile Gln Pro Ala Ala Glu Leu Phe Ala Lys Ile Tyr Glu Asp
305                 310                 315                 320 gcc ggc aag ccc cgc gcc gtc cgc ggt ctc gcc acc aac gtc gcc aac       1008
Ala Gly Lys Pro Arg Ala Val Arg Gly Leu Ala Thr Asn Val Ala Asn
                325                 330                 335 tac aac gcc tgg agc atc tcg agc ccg ccg ccg tac acc agc ccc aac       1056
Tyr Asn Ala Trp Ser Ile Ser Ser Pro Pro Pro Tyr Thr Ser Pro Asn
            340                 345                 350 ccc aac tac gac gag aag cac tac atc gag gcc ttc cgc cct ctc ctc       1104
Pro Asn Tyr Asp Glu Lys His Tyr Ile Glu Ala Phe Arg Pro Leu Leu
        355                 360                 365 gag gcc cgc ggc ttc ccc gcc cag ttc atc gtc gac cag ggc cgc agc       1152
Glu Ala Arg Gly Phe Pro Ala Gln Phe Ile Val Asp Gln Gly Arg Ser
    370                 375                 380 ggc aag cag ccc acc ggc cag aag gaa tgg ggc cac tgg tgc aat gcc       1200
Gly Lys Gln Pro Thr Gly Gln Lys Glu Trp Gly His Trp Cys Asn Ala
385                 390                 395                 400 att ggc acc ggc ttc ggt atg cgc ccg act gcc aac acc ggc cac cag       1248
Ile Gly Thr Gly Phe Gly Met Arg Pro Thr Ala Asn Thr Gly His Gln
                405                 410                 415 tac gtc gac gcc ttc gtc tgg gtc aag ccc ggc ggt gag tgc gac ggc       1296
Tyr Val Asp Ala Phe Val Trp Val Lys Pro Gly Gly Glu Cys Asp Gly
            420                 425                 430 acc agc gac acg acc gct gcc cgc tac gac tac cac tgc ggt ctc gag       1344
Thr Ser Asp Thr Thr Ala Ala Arg Tyr Asp Tyr His Cys Gly Leu Glu
        435                 440                 445 gac gcc ctc aag ccc gcc cct gag gcc ggc cag tgg ttc caa gcc tac       1392
Asp Ala Leu Lys Pro Ala Pro Glu Ala Gly Gln Trp Phe Gln Ala Tyr
    450                 455                 460 ttt gag caa tta ctt cgt aat gcc aat ccg ccg ttc tga                    1431
Phe Glu Gln Leu Leu Arg Asn Ala Asn Pro Pro Phe
465                 470                 475

<210> SEQ ID NO 6
<211> LENGTH: 476
<212> TYPE: PRT
<213> ORGANISM: Humicola insolens

<400> SEQUENCE: 6

Met Ala Lys Phe Phe Leu Thr Ala Ala Phe Ala Ala Ala Ala Leu Ala
1               5                   10                  15

Ala Pro Val Val Glu Glu Arg Gln Asn Cys Ala Pro Thr Trp Gly Gln
                20                  25                  30

Cys Gly Gly Ile Gly Phe Asn Gly Pro Thr Cys Cys Gln Ser Gly Ser
            35                  40                  45

Thr Cys Val Lys Gln Asn Asp Trp Tyr Ser Gln Cys Leu Pro Gly Ser
        50                  55                  60

Gln Val Thr Thr Ser Thr Ser Thr Ser Ser Ser Ser Thr Thr
65                  70                  75                  80

Ser Arg Ala Thr Ser Thr Thr Arg Thr Gly Gly Val Thr Ser Ile Thr
                85                  90                  95

Thr Ala Pro Thr Arg Thr Val Thr Ile Pro Gly Gly Ala Thr Thr Thr
            100                 105                 110
```

```
Ala Ser Tyr Asn Gly Asn Pro Phe Glu Gly Val Gln Leu Trp Ala Asn
        115                 120                 125

Asn Tyr Tyr Arg Ser Glu Val His Thr Leu Ala Ile Pro Gln Ile Thr
    130                 135                 140

Asp Pro Ala Leu Arg Ala Ala Ser Ala Val Ala Glu Val Pro Ser
145                 150                 155                 160

Phe Gln Trp Leu Asp Arg Asn Val Thr Val Asp Thr Leu Leu Val Glu
                165                 170                 175

Thr Leu Ser Glu Ile Arg Ala Ala Asn Gln Ala Gly Ala Asn Pro Pro
            180                 185                 190

Tyr Ala Ala Gln Ile Val Val Tyr Asp Leu Pro Asp Arg Asp Cys Ala
                195                 200                 205

Ala Ala Ala Ser Asn Gly Glu Trp Ala Ile Ala Asn Asn Gly Ala Asn
210                 215                 220

Asn Tyr Lys Gly Tyr Ile Asn Arg Ile Arg Glu Ile Leu Ile Ser Phe
225                 230                 235                 240

Ser Asp Val Arg Thr Ile Leu Val Ile Glu Pro Asp Ser Leu Ala Asn
                245                 250                 255

Met Val Thr Asn Met Asn Val Ala Lys Cys Ser Gly Ala Ala Ser Thr
            260                 265                 270

Tyr Arg Glu Leu Thr Ile Tyr Ala Leu Lys Gln Leu Asp Leu Pro His
        275                 280                 285

Val Ala Met Tyr Met Asp Ala Gly His Ala Gly Trp Leu Gly Trp Pro
    290                 295                 300

Ala Asn Ile Gln Pro Ala Ala Glu Leu Phe Ala Lys Ile Tyr Glu Asp
305                 310                 315                 320

Ala Gly Lys Pro Arg Ala Val Arg Gly Leu Ala Thr Asn Val Ala Asn
                325                 330                 335

Tyr Asn Ala Trp Ser Ile Ser Ser Pro Pro Tyr Thr Ser Pro Asn
            340                 345                 350

Pro Asn Tyr Asp Glu Lys His Tyr Ile Glu Ala Phe Arg Pro Leu Leu
        355                 360                 365

Glu Ala Arg Gly Phe Pro Ala Gln Phe Ile Val Asp Gln Gly Arg Ser
    370                 375                 380

Gly Lys Gln Pro Thr Gly Gln Lys Glu Trp Gly His Trp Cys Asn Ala
385                 390                 395                 400

Ile Gly Thr Gly Phe Gly Met Arg Pro Thr Ala Asn Thr Gly His Gln
                405                 410                 415

Tyr Val Asp Ala Phe Val Trp Val Lys Pro Gly Gly Glu Cys Asp Gly
            420                 425                 430

Thr Ser Asp Thr Thr Ala Ala Arg Tyr Asp Tyr His Cys Gly Leu Glu
        435                 440                 445

Asp Ala Leu Lys Pro Ala Pro Glu Ala Gly Gln Trp Phe Gln Ala Tyr
    450                 455                 460

Phe Glu Gln Leu Leu Arg Asn Ala Asn Pro Pro Phe
465                 470                 475

<210> SEQ ID NO 7
<211> LENGTH: 1431
<212> TYPE: DNA
<213> ORGANISM: Chaetomium thermophilum
<220> FEATURE:
<221> NAME/KEY: CDS
<222> LOCATION: (1)..(1431)
```

```
<400> SEQUENCE: 7 atg gct aag cag ctg ctg ctc act gcc gct ctt gcg gcc act tcg ctg      48
Met Ala Lys Gln Leu Leu Leu Thr Ala Ala Leu Ala Ala Thr Ser Leu
1               5                   10                  15 gct gcc cct ctc ctt gag gag cgc cag agc tgc tcc tcc gtc tgg ggt      96
Ala Ala Pro Leu Leu Glu Glu Arg Gln Ser Cys Ser Ser Val Trp Gly
            20                  25                  30 caa tgc ggt ggc atc aat tac aac ggc ccg acc tgc tgc cag tcc ggc     144
Gln Cys Gly Gly Ile Asn Tyr Asn Gly Pro Thr Cys Cys Gln Ser Gly
        35                  40                  45 agt gtt tgc act tac ctg aat gac tgg tac agc cag tgc att ccc ggt     192
Ser Val Cys Thr Tyr Leu Asn Asp Trp Tyr Ser Gln Cys Ile Pro Gly
    50                  55                  60 cag gct cag ccc ggc acg act agc acc acg gct cgg acc acc agc acc     240
Gln Ala Gln Pro Gly Thr Thr Ser Thr Thr Ala Arg Thr Thr Ser Thr
65                  70                  75                  80 agc acc acc agc act tcg tcg gtc cgc ccg acc acc tcg aat acc cct     288
Ser Thr Thr Ser Thr Ser Ser Val Arg Pro Thr Thr Ser Asn Thr Pro
                85                  90                  95 gtg acg act gct ccc ccg acg acc acc atc ccg ggc ggc gcc tcg agc     336
Val Thr Thr Ala Pro Pro Thr Thr Thr Ile Pro Gly Gly Ala Ser Ser
            100                 105                 110 acg gcc agc tac aac ggc aac ccg ttc tcg ggt gtc caa ctt tgg gcc     384
Thr Ala Ser Tyr Asn Gly Asn Pro Phe Ser Gly Val Gln Leu Trp Ala
        115                 120                 125 aac acc tac tac tcg tcc gag gtg cac act ttg gcc atc ccc agc ttg     432
Asn Thr Tyr Tyr Ser Ser Glu Val His Thr Leu Ala Ile Pro Ser Leu
    130                 135                 140 tct cct gag ctg gct gcc aag gcc gcc aag gtc gct gag gtt ccc agc     480
Ser Pro Glu Leu Ala Ala Lys Ala Ala Lys Val Ala Glu Val Pro Ser
145                 150                 155                 160 ttc cag tgg ctc gac cgc aat gtg act gtt gac act ctc ttc tcc ggc     528
Phe Gln Trp Leu Asp Arg Asn Val Thr Val Asp Thr Leu Phe Ser Gly
                165                 170                 175 act ctt gcc gaa atc cgc gcc gcc aac cag cgc ggt gcc aac ccg cct     576
Thr Leu Ala Glu Ile Arg Ala Ala Asn Gln Arg Gly Ala Asn Pro Pro
            180                 185                 190 tat gcc ggc att ttc gtg gtt tat gac tta cca gac cgt gat tgc gcg     624
Tyr Ala Gly Ile Phe Val Val Tyr Asp Leu Pro Asp Arg Asp Cys Ala
        195                 200                 205 gct gct gct tcg aac ggc gag tgg tct atc gcc aac aat ggt gcc aac     672
Ala Ala Ala Ser Asn Gly Glu Trp Ser Ile Ala Asn Asn Gly Ala Asn
    210                 215                 220 aac tac aag cgc tac atc gac cgg atc cgt gag ctc ctt atc cag tac     720
Asn Tyr Lys Arg Tyr Ile Asp Arg Ile Arg Glu Leu Leu Ile Gln Tyr
225                 230                 235                 240 tcc gat atc cgc act att ctg gtc att gaa cct gat tcc ctg gcc aac     768
Ser Asp Ile Arg Thr Ile Leu Val Ile Glu Pro Asp Ser Leu Ala Asn
                245                 250                 255 atg gtc acc aac atg aac gtc cag aag tgc tcg aac gct gcc tcc act     816
Met Val Thr Asn Met Asn Val Gln Lys Cys Ser Asn Ala Ala Ser Thr
            260                 265                 270 tac aag gag ctt act gtc tat gcc ctc aaa cag ctc aat ctt cct cac     864
Tyr Lys Glu Leu Thr Val Tyr Ala Leu Lys Gln Leu Asn Leu Pro His
        275                 280                 285 gtt gcc atg tac atg gat gct ggc cac gct ggc tgg ctt ggc tgg ccc     912
Val Ala Met Tyr Met Asp Ala Gly His Ala Gly Trp Leu Gly Trp Pro
    290                 295                 300 gcc aac atc cag cct gct gct gag ctc ttt gct caa atc tac cgc gac     960
```

```
Ala Asn Ile Gln Pro Ala Ala Glu Leu Phe Ala Gln Ile Tyr Arg Asp
305                 310                 315                 320 gct ggc agg ccc gct gct gtc cgc ggt ctt gcg acc aac gtt gcc aac      1008
Ala Gly Arg Pro Ala Ala Val Arg Gly Leu Ala Thr Asn Val Ala Asn
                325                 330                 335 tac aat gct tgg tcg atc gcc agc cct ccg tcc tac acc tct cct aac      1056
Tyr Asn Ala Trp Ser Ile Ala Ser Pro Pro Ser Tyr Thr Ser Pro Asn
            340                 345                 350 ccg aac tac gac gag aag cac tat att gag gcc ttt gct cct ctt ctc      1104
Pro Asn Tyr Asp Glu Lys His Tyr Ile Glu Ala Phe Ala Pro Leu Leu
        355                 360                 365 cgc aac cag ggc ttc gac gca aag ttc atc gtc gac acc ggc cgt aac      1152
Arg Asn Gln Gly Phe Asp Ala Lys Phe Ile Val Asp Thr Gly Arg Asn
    370                 375                 380 ggc aag cag ccc act ggc cag ctt gaa tgg ggt cac tgg tgc aat gtc      1200
Gly Lys Gln Pro Thr Gly Gln Leu Glu Trp Gly His Trp Cys Asn Val
385                 390                 395                 400 aag gga act ggc ttc ggt gtg cgc cct act gct aac act ggg cat gaa      1248
Lys Gly Thr Gly Phe Gly Val Arg Pro Thr Ala Asn Thr Gly His Glu
                405                 410                 415 ctt gtt gat gct ttc gtg tgg gtc aag ccc ggt ggc gag tcc gac ggc      1296
Leu Val Asp Ala Phe Val Trp Val Lys Pro Gly Gly Glu Ser Asp Gly
            420                 425                 430 acc agc gac acc agc gct gct cgt tat gac tat cac tgc ggc ctt tcc      1344
Thr Ser Asp Thr Ser Ala Ala Arg Tyr Asp Tyr His Cys Gly Leu Ser
        435                 440                 445 gac gca ctg act ccg gcg cct gag gct ggc caa tgg ttc cag gct tat      1392
Asp Ala Leu Thr Pro Ala Pro Glu Ala Gly Gln Trp Phe Gln Ala Tyr
    450                 455                 460 ttc gaa cag ctg ctc atc aat gcc aac cct ccg ttc tga                  1431
Phe Glu Gln Leu Leu Ile Asn Ala Asn Pro Pro Phe
465                 470                 475
```

<210> SEQ ID NO 8
<211> LENGTH: 476
<212> TYPE: PRT
<213> ORGANISM: Chaetomium thermophilum

<400> SEQUENCE: 8

```
Met Ala Lys Gln Leu Leu Thr Ala Ala Leu Ala Ala Thr Ser Leu
1               5                   10                  15

Ala Ala Pro Leu Leu Glu Glu Arg Gln Ser Cys Ser Ser Val Trp Gly
                20                  25                  30

Gln Cys Gly Gly Ile Asn Tyr Asn Gly Pro Thr Cys Cys Gln Ser Gly
            35                  40                  45

Ser Val Cys Thr Tyr Leu Asn Asp Trp Tyr Ser Gln Cys Ile Pro Gly
        50                  55                  60

Gln Ala Gln Pro Gly Thr Thr Ser Thr Thr Ala Arg Thr Thr Ser Thr
65                  70                  75                  80

Ser Thr Thr Ser Thr Ser Ser Val Arg Pro Thr Thr Ser Asn Thr Pro
                85                  90                  95

Val Thr Thr Ala Pro Pro Thr Thr Thr Ile Pro Gly Gly Ala Ser Ser
            100                 105                 110

Thr Ala Ser Tyr Asn Gly Asn Pro Phe Ser Gly Val Gln Leu Trp Ala
        115                 120                 125

Asn Thr Tyr Tyr Ser Ser Glu Val His Thr Leu Ala Ile Pro Ser Leu
    130                 135                 140

Ser Pro Glu Leu Ala Ala Lys Ala Ala Lys Val Ala Glu Val Pro Ser
145                 150                 155                 160
```

```
Phe Gln Trp Leu Asp Arg Asn Val Thr Val Asp Thr Leu Phe Ser Gly
                165                 170                 175
Thr Leu Ala Glu Ile Arg Ala Ala Asn Gln Arg Gly Ala Asn Pro Pro
            180                 185                 190
Tyr Ala Gly Ile Phe Val Val Tyr Asp Leu Pro Asp Arg Asp Cys Ala
        195                 200                 205
Ala Ala Ala Ser Asn Gly Glu Trp Ser Ile Ala Asn Asn Gly Ala Asn
    210                 215                 220
Asn Tyr Lys Arg Tyr Ile Asp Arg Ile Arg Glu Leu Leu Ile Gln Tyr
225                 230                 235                 240
Ser Asp Ile Arg Thr Ile Leu Val Ile Glu Pro Asp Ser Leu Ala Asn
                245                 250                 255
Met Val Thr Asn Met Asn Val Gln Lys Cys Ser Asn Ala Ala Ser Thr
            260                 265                 270
Tyr Lys Glu Leu Thr Val Tyr Ala Leu Lys Gln Leu Asn Leu Pro His
        275                 280                 285
Val Ala Met Tyr Met Asp Ala Gly His Ala Gly Trp Leu Gly Trp Pro
    290                 295                 300
Ala Asn Ile Gln Pro Ala Ala Glu Leu Phe Ala Gln Ile Tyr Arg Asp
305                 310                 315                 320
Ala Gly Arg Pro Ala Ala Val Arg Gly Leu Ala Thr Asn Val Ala Asn
                325                 330                 335
Tyr Asn Ala Trp Ser Ile Ala Ser Pro Pro Ser Tyr Thr Ser Pro Asn
            340                 345                 350
Pro Asn Tyr Asp Glu Lys His Tyr Ile Glu Ala Phe Ala Pro Leu Leu
        355                 360                 365
Arg Asn Gln Gly Phe Asp Ala Lys Phe Ile Val Asp Thr Gly Arg Asn
    370                 375                 380
Gly Lys Gln Pro Thr Gly Gln Leu Glu Trp Gly His Trp Cys Asn Val
385                 390                 395                 400
Lys Gly Thr Gly Phe Gly Val Arg Pro Thr Ala Asn Thr Gly His Glu
                405                 410                 415
Leu Val Asp Ala Phe Val Trp Val Lys Pro Gly Gly Glu Ser Asp Gly
            420                 425                 430
Thr Ser Asp Thr Ser Ala Ala Arg Tyr Asp Tyr His Cys Gly Leu Ser
        435                 440                 445
Asp Ala Leu Thr Pro Ala Pro Glu Ala Gly Gln Trp Phe Gln Ala Tyr
    450                 455                 460
Phe Glu Gln Leu Leu Ile Asn Ala Asn Pro Pro Phe
465                 470                 475

<210> SEQ ID NO 9
<211> LENGTH: 267
<212> TYPE: DNA
<213> ORGANISM: Artificial Sequence
<220> FEATURE:
<223> OTHER INFORMATION: CBD-Linker
<220> FEATURE:
<221> NAME/KEY: CDS
<222> LOCATION: (1)..(267)

<400> SEQUENCE: 9 gct agc tgc tca agc gtc tgg ggc caa tgt ggt ggc cag aat tgg tcg       48
Ala Ser Cys Ser Ser Val Trp Gly Gln Cys Gly Gly Gln Asn Trp Ser
1               5                   10                  15 ggt ccg act tgc tgt gct tcc gga agc aca tgc gtc tac tcc aac gac       96
```

```
Gly Pro Thr Cys Cys Ala Ser Gly Ser Thr Cys Val Tyr Ser Asn Asp
            20                  25                  30 tat tac tcc cag tgt ctt ccc ggc gct gca agc tca agc tcg tcc acg       144
Tyr Tyr Ser Gln Cys Leu Pro Gly Ala Ala Ser Ser Ser Ser Ser Thr
        35                  40                  45 cgc gcc gcg tcg acg act tct cga gta tcc ccc aca aca tcc cgg tcg       192
Arg Ala Ala Ser Thr Thr Ser Arg Val Ser Pro Thr Thr Ser Arg Ser
    50                  55                  60 agc tcc gcg acg cct cca cct ggt tct act act acc aga gta cct cca       240
Ser Ser Ala Thr Pro Pro Pro Gly Ser Thr Thr Thr Arg Val Pro Pro
65                  70                  75                  80 gtc gga tcg gga acc gct acg tat tca                                   267
Val Gly Ser Gly Thr Ala Thr Tyr Ser
                85
```

<210> SEQ ID NO 10
<211> LENGTH: 89
<212> TYPE: PRT
<213> ORGANISM: Artificial Sequence
<220> FEATURE:
<223> OTHER INFORMATION: Synthetic Construct

<400> SEQUENCE: 10

```
Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser
                85
```

<210> SEQ ID NO 11
<211> LENGTH: 1362
<212> TYPE: DNA
<213> ORGANISM: Artificial Sequence
<220> FEATURE:
<223> OTHER INFORMATION: Cel6A engineered variant S317W
<220> FEATURE:
<221> NAME/KEY: CDS
<222> LOCATION: (1)..(1362)

<400> SEQUENCE: 11

```
gct agc tgc tca agc gtc tgg ggc caa tgt ggt ggc cag aat tgg tcg        48
Ala Ser Cys Ser Ser Val Trp Gly Gln Cys Gly Gly Gln Asn Trp Ser
1               5                   10                  15 ggt ccg act tgc tgt gct tcc gga agc aca tgc gtc tac tcc aac gac        96
Gly Pro Thr Cys Cys Ala Ser Gly Ser Thr Cys Val Tyr Ser Asn Asp
            20                  25                  30 tat tac tcc cag tgt ctt ccc ggc gct gca agc tca agc tcg tcc acg       144
Tyr Tyr Ser Gln Cys Leu Pro Gly Ala Ala Ser Ser Ser Ser Ser Thr
        35                  40                  45 cgc gcc gcg tcg acg act tct cga gta tcc ccc aca aca tcc cgg tcg       192
Arg Ala Ala Ser Thr Thr Ser Arg Val Ser Pro Thr Thr Ser Arg Ser
    50                  55                  60 agc tcc gcg acg cct cca cct ggt tct act act acc aga gta cct cca       240
Ser Ser Ala Thr Pro Pro Pro Gly Ser Thr Thr Thr Arg Val Pro Pro
65                  70                  75                  80
```

| | | |
|---|---|---|
| gtc gga tcg gga acc gct acg tat tca ggt aac ccc ttt gaa ggt gtt<br>Val Gly Ser Gly Thr Ala Thr Tyr Ser Gly Asn Pro Phe Glu Gly Val<br>                        85                      90                  95 | 288 |
| cag ctg tgg gct aat aac tat tat aga tct gag gta cat aca ctg gcc<br>Gln Leu Trp Ala Asn Asn Tyr Tyr Arg Ser Glu Val His Thr Leu Ala<br>100                       105                    110 | 336 |
| att ccg caa att aca gac ccc gcg ttg cgt gcc gca gct agt gct gtg<br>Ile Pro Gln Ile Thr Asp Pro Ala Leu Arg Ala Ala Ala Ser Ala Val<br>         115                    120                    125 | 384 |
| gct gag gtg cca agt ttt atg tgg ctg gat act ttg gac aaa acc ccc<br>Ala Glu Val Pro Ser Phe Met Trp Leu Asp Thr Leu Asp Lys Thr Pro<br>130                       135                    140 | 432 |
| tta atg gaa caa acg ttg gct gat ata cgt act gcg aat aaa aac ggc<br>Leu Met Glu Gln Thr Leu Ala Asp Ile Arg Thr Ala Asn Lys Asn Gly<br>145                       150                    155                    160 | 480 |
| ggc aat tat gct gga caa ttt gtg gtt tat gac ctg ccg gat aga gat<br>Gly Asn Tyr Ala Gly Gln Phe Val Val Tyr Asp Leu Pro Asp Arg Asp<br>               165                    170                    175 | 528 |
| tgt gct gca cta gcg agc aac ggg gag tac agc att gcg gat ggc ggt<br>Cys Ala Ala Leu Ala Ser Asn Gly Glu Tyr Ser Ile Ala Asp Gly Gly<br>                  180                    185                    190 | 576 |
| gtc gca aag tac aaa aac tat ata gat act atc agg caa ata gtt gtc<br>Val Ala Lys Tyr Lys Asn Tyr Ile Asp Thr Ile Arg Gln Ile Val Val<br>         195                    200                    205 | 624 |
| gaa tac agt gat att cgt acg ctg ctt gta atc gaa ccc gat tcc tta<br>Glu Tyr Ser Asp Ile Arg Thr Leu Leu Val Ile Glu Pro Asp Ser Leu<br>210                       215                    220 | 672 |
| gcg aac ttg gtg aca aat cta ggt act ccg aag tgt gcg aac gcg cag<br>Ala Asn Leu Val Thr Asn Leu Gly Thr Pro Lys Cys Ala Asn Ala Gln<br>225                       230                    235                    240 | 720 |
| agt gct tat ctt gag tgc atc aat tat gca gtc acc cag ttg aat ttg<br>Ser Ala Tyr Leu Glu Cys Ile Asn Tyr Ala Val Thr Gln Leu Asn Leu<br>                  245                    250                    255 | 768 |
| cca aac gtt gca atg tat ctt gat gct ggt cat gcc ggg tgg ttg ggt<br>Pro Asn Val Ala Met Tyr Leu Asp Ala Gly His Ala Gly Trp Leu Gly<br>                  260                    265                    270 | 816 |
| tgg cca gca aat cag gat ccc gct gcg cag ctg ttt gca aat gtt tac<br>Trp Pro Ala Asn Gln Asp Pro Ala Ala Gln Leu Phe Ala Asn Val Tyr<br>         275                    280                    285 | 864 |
| aaa aat gcc tca agt cct aga gcg ctg agg ggt ctt gca aca aat gtt<br>Lys Asn Ala Ser Ser Pro Arg Ala Leu Arg Gly Leu Ala Thr Asn Val<br>290                       295                    300 | 912 |
| gct aat tac aac gct tgg tca ata gcg agt cct cca tgg tac aca agc<br>Ala Asn Tyr Asn Ala Trp Ser Ile Ala Ser Pro Pro Trp Tyr Thr Ser<br>305                       310                    315                    320 | 960 |
| cct aac cca aac tac gat gag aag cat tac ata gaa gca ttt gct cct<br>Pro Asn Pro Asn Tyr Asp Glu Lys His Tyr Ile Glu Ala Phe Ala Pro<br>               325                    330                    335 | 1008 |
| ttg ctt cgt aac caa ggt ttt gat gca aag ttt atc gtc gat acc gga<br>Leu Leu Arg Asn Gln Gly Phe Asp Ala Lys Phe Ile Val Asp Thr Gly<br>                  340                    345                    350 | 1056 |
| aga aac ggc aag cag ccg aca ggg cag cta gaa tgg ggg cac tgg tgc<br>Arg Asn Gly Lys Gln Pro Thr Gly Gln Leu Glu Trp Gly His Trp Cys<br>         355                    360                    365 | 1104 |
| aat gtc aag ggt acg ggt ttc ggt gtt aga ccc acg gct aac act ggg<br>Asn Val Lys Gly Thr Gly Phe Gly Val Arg Pro Thr Ala Asn Thr Gly<br>370                       375                    380 | 1152 |
| cat gag ttg gtt gat gca ttc gtt tgg gta aaa ccc gga gga gag tca<br>His Glu Leu Val Asp Ala Phe Val Trp Val Lys Pro Gly Gly Glu Ser | 1200 |

```
                385                 390                 395                 400
gat gga acg agt gat tct tct gct cca agg ttc gat tct cat tgc gca      1248
Asp Gly Thr Ser Asp Ser Ser Ala Pro Arg Phe Asp Ser His Cys Ala
                405                 410                 415 tta cca gat gct ttg cag cca gca cct caa gca gga gct tgg ttc caa      1296
Leu Pro Asp Ala Leu Gln Pro Ala Pro Gln Ala Gly Ala Trp Phe Gln
                420                 425                 430 gct tat ttt gta caa tta ctg act aac gcc aat cct agt ttt cta cat      1344
Ala Tyr Phe Val Gln Leu Leu Thr Asn Ala Asn Pro Ser Phe Leu His
                435                 440                 445 cac cat cac cac cat tag                                              1362
His His His His His
                450

<210> SEQ ID NO 12
<211> LENGTH: 453
<212> TYPE: PRT
<213> ORGANISM: Artificial Sequence
<220> FEATURE:
<223> OTHER INFORMATION: Synthetic Construct

<400> SEQUENCE: 12

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro Val
65                  70                  75                  80

Val Gly Ser Gly Thr Ala Thr Tyr Ser Gly Asn Pro Phe Glu Gly Val
                85                  90                  95

Gln Leu Trp Ala Asn Asn Tyr Tyr Arg Ser Glu Val His Thr Leu Ala
            100                 105                 110

Ile Pro Gln Ile Thr Asp Pro Ala Leu Arg Ala Ala Ser Ala Val
    115                 120                 125

Ala Glu Val Pro Ser Phe Met Trp Leu Asp Thr Leu Asp Lys Thr Pro
130                 135                 140

Leu Met Glu Gln Thr Leu Ala Asp Ile Arg Thr Ala Asn Lys Asn Gly
145                 150                 155                 160

Gly Asn Tyr Ala Gly Gln Phe Val Val Tyr Asp Leu Pro Asp Arg Asp
                165                 170                 175

Cys Ala Ala Leu Ala Ser Asn Gly Glu Tyr Ser Ile Ala Asp Gly Gly
            180                 185                 190

Val Ala Lys Tyr Lys Asn Tyr Ile Asp Thr Ile Arg Gln Ile Val Val
    195                 200                 205

Glu Tyr Ser Asp Ile Arg Thr Leu Leu Val Ile Glu Pro Asp Ser Leu
210                 215                 220

Ala Asn Leu Val Thr Asn Leu Gly Thr Pro Lys Cys Ala Asn Ala Gln
225                 230                 235                 240

Ser Ala Tyr Leu Glu Cys Ile Asn Tyr Ala Val Thr Gln Leu Asn Leu
                245                 250                 255

Pro Asn Val Ala Met Tyr Leu Asp Ala Gly His Ala Gly Trp Leu Gly
            260                 265                 270
```

```
Trp Pro Ala Asn Gln Asp Pro Ala Gln Leu Phe Ala Asn Val Tyr
                275                 280                 285
Lys Asn Ala Ser Ser Pro Arg Ala Leu Arg Gly Leu Ala Thr Asn Val
    290                 295                 300
Ala Asn Tyr Asn Ala Trp Ser Ile Ala Ser Pro Pro Trp Tyr Thr Ser
305                 310                 315                 320
Pro Asn Pro Asn Tyr Asp Glu Lys His Tyr Ile Glu Ala Phe Ala Pro
                325                 330                 335
Leu Leu Arg Asn Gln Gly Phe Asp Ala Lys Phe Ile Val Asp Thr Gly
                340                 345                 350
Arg Asn Gly Lys Gln Pro Thr Gly Gln Leu Glu Trp Gly His Trp Cys
                355                 360                 365
Asn Val Lys Gly Thr Gly Phe Gly Val Arg Pro Thr Ala Asn Thr Gly
    370                 375                 380
His Glu Leu Val Asp Ala Phe Val Trp Val Lys Pro Gly Gly Glu Ser
385                 390                 395                 400
Asp Gly Thr Ser Asp Ser Ser Ala Pro Arg Phe Asp Ser His Cys Ala
                405                 410                 415
Leu Pro Asp Ala Leu Gln Pro Ala Gln Ala Gly Ala Trp Phe Gln
                420                 425                 430
Ala Tyr Phe Val Gln Leu Leu Thr Asn Ala Asn Pro Ser Phe Leu His
            435                 440                 445
His His His His
    450

<210> SEQ ID NO 13
<211> LENGTH: 1362
<212> TYPE: DNA
<213> ORGANISM: Artificial Sequence
<220> FEATURE:
<223> OTHER INFORMATION: Cel6a engineered variant S413W
<220> FEATURE:
<221> NAME/KEY: CDS
<222> LOCATION: (1)..(1362)

<400> SEQUENCE: 13 gct agc tgc tca agc gtc tgg ggc caa tgt ggt ggc cag aat tgg tcg      48
Ala Ser Cys Ser Ser Val Trp Gly Gln Cys Gly Gly Gln Asn Trp Ser
1               5                   10                  15 ggt ccg act tgc tgt gct tcc gga agc aca tgc gtc tac tcc aac gac      96
Gly Pro Thr Cys Cys Ala Ser Gly Ser Thr Cys Val Tyr Ser Asn Asp
                20                  25                  30 tat tac tcc cag tgt ctt ccc ggc gct gca agc tca agc tcg tcc acg     144
Tyr Tyr Ser Gln Cys Leu Pro Gly Ala Ala Ser Ser Ser Ser Ser Thr
            35                  40                  45 cgc gcc gcg tcg acg act tct cga gta tcc ccc aca aca tcc cgg tcg     192
Arg Ala Ala Ser Thr Thr Ser Arg Val Ser Pro Thr Thr Ser Arg Ser
        50                  55                  60 agc tcc gcg acg cct cca cct ggt tct act act acc aga gta cct cca     240
Ser Ser Ala Thr Pro Pro Pro Gly Ser Thr Thr Thr Arg Val Pro Pro
65                  70                  75                  80 gtc gga tcg gga acc gct acg tat tca ggt aac ccc ttt gaa ggt gtt     288
Val Gly Ser Gly Thr Ala Thr Tyr Ser Gly Asn Pro Phe Glu Gly Val
                85                  90                  95 cag ctg tgg gct aat aac tat tat aga tct gag gta cat aca ctg gcc     336
Gln Leu Trp Ala Asn Asn Tyr Tyr Arg Ser Glu Val His Thr Leu Ala
            100                 105                 110 att ccg caa att aca gac ccc gcg ttg cgt gcc gca gct agt gct gtg     384
Ile Pro Gln Ile Thr Asp Pro Ala Leu Arg Ala Ala Ala Ser Ala Val
```

```
                    115                 120                 125
gct gag gtg cca agt ttt atg tgg ctg gat act ttg gac aaa acc ccc     432
Ala Glu Val Pro Ser Phe Met Trp Leu Asp Thr Leu Asp Lys Thr Pro
    130                 135                 140 tta atg gaa caa acg ttg gct gat ata cgt act gcg aat aaa aac ggc     480
Leu Met Glu Gln Thr Leu Ala Asp Ile Arg Thr Ala Asn Lys Asn Gly
145                 150                 155                 160 ggc aat tat gct gga caa ttt gtg gtt tat gac ctg ccg gat aga gat     528
Gly Asn Tyr Ala Gly Gln Phe Val Val Tyr Asp Leu Pro Asp Arg Asp
                165                 170                 175 tgt gct gca cta gcg agc aac ggg gag tac agc att gcg gat ggc ggt     576
Cys Ala Ala Leu Ala Ser Asn Gly Glu Tyr Ser Ile Ala Asp Gly Gly
            180                 185                 190 gtc gca aag tac aaa aac tat ata gat act atc agg caa ata gtt gtc     624
Val Ala Lys Tyr Lys Asn Tyr Ile Asp Thr Ile Arg Gln Ile Val Val
        195                 200                 205 gaa tac agt gat att cgt acg ctg ctt gta atc gaa ccc gat tcc tta     672
Glu Tyr Ser Asp Ile Arg Thr Leu Leu Val Ile Glu Pro Asp Ser Leu
    210                 215                 220 gcg aac ttg gtg aca aat cta ggt act ccg aag tgt gcg aac gcg cag     720
Ala Asn Leu Val Thr Asn Leu Gly Thr Pro Lys Cys Ala Asn Ala Gln
225                 230                 235                 240 agt gct tat ctt gag tgc atc aat tat gca gtc acc cag ttg aat ttg     768
Ser Ala Tyr Leu Glu Cys Ile Asn Tyr Ala Val Thr Gln Leu Asn Leu
                245                 250                 255 cca aac gtt gca atg tat ctt gat gct ggt cat gcc ggg tgg ttg ggt     816
Pro Asn Val Ala Met Tyr Leu Asp Ala Gly His Ala Gly Trp Leu Gly
            260                 265                 270 tgg cca gca aat cag gat ccc gct gcg cag ctg ttt gca aat gtt tac     864
Trp Pro Ala Asn Gln Asp Pro Ala Ala Gln Leu Phe Ala Asn Val Tyr
        275                 280                 285 aaa aat gcc tca agt cct aga gcg ctg agg ggt ctt gca aca aat gtt     912
Lys Asn Ala Ser Ser Pro Arg Ala Leu Arg Gly Leu Ala Thr Asn Val
    290                 295                 300 gct aat tac aac gct tgg tca ata gcg agt cct cca tcg tac aca agc     960
Ala Asn Tyr Asn Ala Trp Ser Ile Ala Ser Pro Pro Ser Tyr Thr Ser
305                 310                 315                 320 cct aac cca aac tac gat gag aag cat tac ata gaa gca ttt gct cct    1008
Pro Asn Pro Asn Tyr Asp Glu Lys His Tyr Ile Glu Ala Phe Ala Pro
                325                 330                 335 ttg ctt cgt aac caa ggt ttt gat gca aag ttt atc gtc gat acc gga    1056
Leu Leu Arg Asn Gln Gly Phe Asp Ala Lys Phe Ile Val Asp Thr Gly
            340                 345                 350 aga aac ggc aag cag ccg aca ggg cag cta gaa tgg ggg cac tgg tgc    1104
Arg Asn Gly Lys Gln Pro Thr Gly Gln Leu Glu Trp Gly His Trp Cys
        355                 360                 365 aat gtc aag ggt acg ggt ttc ggt gtt aga ccc acg gct aac act ggg    1152
Asn Val Lys Gly Thr Gly Phe Gly Val Arg Pro Thr Ala Asn Thr Gly
    370                 375                 380 cat gag ttg gtt gat gca ttc gtt tgg gta aaa ccc gga gga gag tca    1200
His Glu Leu Val Asp Ala Phe Val Trp Val Lys Pro Gly Gly Glu Ser
385                 390                 395                 400 gat gga acg agt gat tct tct gct cca agg ttc gat tgg cat tgc gca    1248
Asp Gly Thr Ser Asp Ser Ser Ala Pro Arg Phe Asp Trp His Cys Ala
                405                 410                 415 tta cca gat gct ttg cag cca gca cct caa gca gga gct tgg ttc caa    1296
Leu Pro Asp Ala Leu Gln Pro Ala Pro Gln Ala Gly Ala Trp Phe Gln
            420                 425                 430 gct tat ttt gta caa tta ctg act aac gcc aat cct agt ttt cta cat    1344
```

```
Ala Tyr Phe Val Gln Leu Leu Thr Asn Ala Asn Pro Ser Phe Leu His
        435                 440                 445 cac cat cac cac cat tag                                              1362
His His His His His
        450

<210> SEQ ID NO 14
<211> LENGTH: 453
<212> TYPE: PRT
<213> ORGANISM: Artificial Sequence
<220> FEATURE:
<223> OTHER INFORMATION: Synthetic Construct

<400> SEQUENCE: 14

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Glu Gly Val
                85                  90                  95

Gln Leu Trp Ala Asn Asn Tyr Tyr Arg Ser Glu Val His Thr Leu Ala
            100                 105                 110

Ile Pro Gln Ile Thr Asp Pro Ala Leu Arg Ala Ala Ala Ser Ala Val
        115                 120                 125

Ala Glu Val Pro Ser Phe Met Trp Leu Asp Thr Leu Asp Lys Thr Pro
    130                 135                 140

Leu Met Glu Gln Thr Leu Ala Asp Ile Arg Thr Ala Asn Lys Asn Gly
145                 150                 155                 160

Gly Asn Tyr Ala Gly Gln Phe Val Val Tyr Asp Leu Pro Asp Arg Asp
                165                 170                 175

Cys Ala Ala Leu Ala Ser Asn Gly Glu Tyr Ser Ile Ala Asp Gly Gly
            180                 185                 190

Val Ala Lys Tyr Lys Asn Tyr Ile Asp Thr Ile Arg Gln Ile Val Val
        195                 200                 205

Glu Tyr Ser Asp Ile Arg Thr Leu Leu Val Ile Glu Pro Asp Ser Leu
    210                 215                 220

Ala Asn Leu Val Thr Asn Leu Gly Thr Pro Lys Cys Ala Asn Ala Gln
225                 230                 235                 240

Ser Ala Tyr Leu Glu Cys Ile Asn Tyr Ala Val Thr Gln Leu Asn Leu
                245                 250                 255

Pro Asn Val Ala Met Tyr Leu Asp Ala Gly His Ala Gly Trp Leu Gly
            260                 265                 270

Trp Pro Ala Asn Gln Asp Pro Ala Ala Gln Leu Phe Ala Asn Val Tyr
        275                 280                 285

Lys Asn Ala Ser Ser Pro Arg Ala Leu Arg Gly Leu Ala Thr Asn Val
    290                 295                 300

Ala Asn Tyr Asn Ala Trp Ser Ile Ala Ser Pro Ser Tyr Thr Ser
305                 310                 315                 320

Pro Asn Pro Asn Tyr Asp Glu Lys His Tyr Ile Glu Ala Phe Ala Pro
                325                 330                 335
```

-continued

```
Leu Leu Arg Asn Gln Gly Phe Asp Ala Lys Phe Ile Val Asp Thr Gly
         340                 345                 350

Arg Asn Gly Lys Gln Pro Thr Gly Gln Leu Glu Trp Gly His Trp Cys
         355                 360                 365

Asn Val Lys Gly Thr Gly Phe Gly Val Arg Pro Thr Ala Asn Thr Gly
         370                 375                 380

His Glu Leu Val Asp Ala Phe Val Trp Val Lys Pro Gly Gly Glu Ser
385                 390                 395                 400

Asp Gly Thr Ser Asp Ser Ser Ala Pro Arg Phe Asp Trp His Cys Ala
             405                 410                 415

Leu Pro Asp Ala Leu Gln Pro Ala Pro Gln Ala Gly Ala Trp Phe Gln
             420                 425                 430

Ala Tyr Phe Val Gln Leu Leu Thr Asn Ala Asn Pro Ser Phe Leu His
             435                 440                 445

His His His His His
         450

<210> SEQ ID NO 15
<211> LENGTH: 1362
<212> TYPE: DNA
<213> ORGANISM: Artificial Sequence
<220> FEATURE:
<223> OTHER INFORMATION: Cel6a engineered variant 1F4
<220> FEATURE:
<221> NAME/KEY: CDS
<222> LOCATION: (1)..(1362)

<400> SEQUENCE: 15 gct agc tgc tca agc gtc tgg ggc caa tgt ggt ggc cag aat tgg tcg     48
Ala Ser Cys Ser Ser Val Trp Gly Gln Cys Gly Gly Gln Asn Trp Ser
1               5                   10                  15 ggt ccg act tgc tgt gct tcc gga agc aca tgc gtc tac tcc aac gac     96
Gly Pro Thr Cys Cys Ala Ser Gly Ser Thr Cys Val Tyr Ser Asn Asp
            20                  25                  30 tat tac tcc cag tgt ctt ccc ggc gct gca agc tca agc tcg tcc acg    144
Tyr Tyr Ser Gln Cys Leu Pro Gly Ala Ala Ser Ser Ser Ser Ser Thr
        35                  40                  45 cgc gcc gcg tcg acg act tct cga gta tcc ccc aca aca tcc cgg tcg    192
Arg Ala Ala Ser Thr Thr Ser Arg Val Ser Pro Thr Thr Ser Arg Ser
    50                  55                  60 agc tcc gcg acg cct cca cct ggt tct act act acc aga gta cct cca    240
Ser Ser Ala Thr Pro Pro Pro Gly Ser Thr Thr Thr Arg Val Pro Pro
65                  70                  75                  80 gtc gga tcg gga acc gct acg tat tca ggt aac ccc ttt gaa ggt gtt    288
Val Gly Ser Gly Thr Ala Thr Tyr Ser Gly Asn Pro Phe Glu Gly Val
                85                  90                  95 cag ctg tgg gct aat aac tat tat aga tct gag gta cat aca ctg gcc    336
Gln Leu Trp Ala Asn Asn Tyr Tyr Arg Ser Glu Val His Thr Leu Ala
            100                 105                 110 att ccg caa att aca gac ccc gcg ttg cgt gcc gca gct agt gct gtg    384
Ile Pro Gln Ile Thr Asp Pro Ala Leu Arg Ala Ala Ala Ser Ala Val
        115                 120                 125 gct gag gtg cca agt ttt atg tgg ctg gat act ttg gac aaa acc ccc    432
Ala Glu Val Pro Ser Phe Met Trp Leu Asp Thr Leu Asp Lys Thr Pro
    130                 135                 140 tta atg gaa caa acg ttg gct gat ata cgt act gca aat aaa aac ggc    480
Leu Met Glu Gln Thr Leu Ala Asp Ile Arg Thr Ala Asn Lys Asn Gly
145                 150                 155                 160 ggc aat tat gct gga caa ttt gtg gtt tat gac ctg ccg gat aga gat    528
Gly Asn Tyr Ala Gly Gln Phe Val Val Tyr Asp Leu Pro Asp Arg Asp
```

```
                  165                 170                 175
tgt gct gca cta gcg agc aac ggg gag tac agc att gcg gat ggc ggt     576
Cys Ala Ala Leu Ala Ser Asn Gly Glu Tyr Ser Ile Ala Asp Gly Gly
        180                 185                 190 gtc gca aag tac aaa aac tat ata gat act atc agg caa ata gtt gtc     624
Val Ala Lys Tyr Lys Asn Tyr Ile Asp Thr Ile Arg Gln Ile Val Val
            195                 200                 205 gaa tac agt gat att cgt acg ctg ctt gta atc gaa ccc gat tcc tta     672
Glu Tyr Ser Asp Ile Arg Thr Leu Leu Val Ile Glu Pro Asp Ser Leu
    210                 215                 220 gcg aac ttg gtg aca aat cta ggt act ccg aag tgt gcg aac gcg cag     720
Ala Asn Leu Val Thr Asn Leu Gly Thr Pro Lys Cys Ala Asn Ala Gln
225                 230                 235                 240 agt gct tat ctt gag tgc atc aat tat gca gtc acc cag ttg aat ttg     768
Ser Ala Tyr Leu Glu Cys Ile Asn Tyr Ala Val Thr Gln Leu Asn Leu
                245                 250                 255 cca aac gtt gca atg tat ctt gat gct ggt cat gcc ggg tgg ttg ggt     816
Pro Asn Val Ala Met Tyr Leu Asp Ala Gly His Ala Gly Trp Leu Gly
            260                 265                 270 tgg cca gca aat cag gat ccc gct gcg cag ctg ttt gca aat gtt tac     864
Trp Pro Ala Asn Gln Asp Pro Ala Ala Gln Leu Phe Ala Asn Val Tyr
    275                 280                 285 aaa aat gcc tca agt cct aga gcg ctg agg ggt ctt gca aca aat gtt     912
Lys Asn Ala Ser Ser Pro Arg Ala Leu Arg Gly Leu Ala Thr Asn Val
290                 295                 300 gct aat tac aac gct tgg tca ata gcg agt cct cca tcg tac aca agc     960
Ala Asn Tyr Asn Ala Trp Ser Ile Ala Ser Pro Pro Ser Tyr Thr Ser
                310                 315                 320 cct aac cca aac tac gat gag aag cat tac ata gaa gca ttt gct cct    1008
Pro Asn Pro Asn Tyr Asp Glu Lys His Tyr Ile Glu Ala Phe Ala Pro
            325                 330                 335 ttg ctt cgt aac caa ggt ttt gat gca aag ttt atc gtc gat acc gga    1056
Leu Leu Arg Asn Gln Gly Phe Asp Ala Lys Phe Ile Val Asp Thr Gly
    340                 345                 350 aga aac ggc aag cag ccg aca ggg cag cta gaa tgg ggg cac tgg tgc    1104
Arg Asn Gly Lys Gln Pro Thr Gly Gln Leu Glu Trp Gly His Trp Cys
355                 360                 365 aat gtc aag ggt acg ggt ttc ggt gtt aga ccc acg gct aac act ggg    1152
Asn Val Lys Gly Thr Gly Phe Gly Val Arg Pro Thr Ala Asn Thr Gly
    370                 375                 380 cat gag ttg gtt gat gca ttc gtt tgg gta aaa ccc gga gga gag tca    1200
His Glu Leu Val Asp Ala Phe Val Trp Val Lys Pro Gly Gly Glu Ser
385                 390                 395                 400 gat gga acg agt gat tct tct gct cca agg ttc gat ttt cat tgc gca    1248
Asp Gly Thr Ser Asp Ser Ser Ala Pro Arg Phe Asp Phe His Cys Ala
                405                 410                 415 tta cca gat gct ttg cag cca gca cct caa gca gga gct tgg ttc caa    1296
Leu Pro Asp Ala Leu Gln Pro Ala Pro Gln Ala Gly Ala Trp Phe Gln
            420                 425                 430 gct tat ttt gta caa tta ctg act aac gcc aat cct agt ttt cta cat    1344
Ala Tyr Phe Val Gln Leu Leu Thr Asn Ala Asn Pro Ser Phe Leu His
    435                 440                 445 cac cat cac cac cat tag                                            1362
His His His His His
    450

<210> SEQ ID NO 16
<211> LENGTH: 453
<212> TYPE: PRT
<213> ORGANISM: Artificial Sequence
```

```
<220> FEATURE:
<223> OTHER INFORMATION: Synthetic Construct

<400> SEQUENCE: 16

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ser Ser Ser Ser Ser Ser Thr
            35                  40                  45

Arg Ala Ala Ser Thr Thr Ser Arg Val Ser Pro Thr Thr Ser Arg Ser
50                      55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Glu Gly Val
                85                  90                  95

Gln Leu Trp Ala Asn Asn Tyr Tyr Arg Ser Glu Val His Thr Leu Ala
            100                 105                 110

Ile Pro Gln Ile Thr Asp Pro Ala Leu Arg Ala Ala Ser Ala Val
            115                 120                 125

Ala Glu Val Pro Ser Phe Met Trp Leu Asp Thr Leu Asp Lys Thr Pro
130                 135                 140

Leu Met Glu Gln Thr Leu Ala Asp Ile Arg Thr Ala Asn Lys Asn Gly
145                 150                 155                 160

Gly Asn Tyr Ala Gly Gln Phe Val Val Tyr Asp Leu Pro Asp Arg Asp
                165                 170                 175

Cys Ala Ala Leu Ala Ser Asn Gly Glu Tyr Ser Ile Ala Asp Gly Gly
            180                 185                 190

Val Ala Lys Tyr Lys Asn Tyr Ile Asp Thr Ile Arg Gln Ile Val Val
            195                 200                 205

Glu Tyr Ser Asp Ile Arg Thr Leu Leu Val Ile Glu Pro Asp Ser Leu
210                 215                 220

Ala Asn Leu Val Thr Asn Leu Gly Thr Pro Lys Cys Ala Asn Ala Gln
225                 230                 235                 240

Ser Ala Tyr Leu Glu Cys Ile Asn Tyr Ala Val Thr Gln Leu Asn Leu
                245                 250                 255

Pro Asn Val Ala Met Tyr Leu Asp Ala Gly His Ala Gly Trp Leu Gly
                260                 265                 270

Trp Pro Ala Asn Gln Asp Pro Ala Ala Gln Leu Phe Ala Asn Val Tyr
            275                 280                 285

Lys Asn Ala Ser Ser Pro Arg Ala Leu Arg Gly Leu Ala Thr Asn Val
290                 295                 300

Ala Asn Tyr Asn Ala Trp Ser Ile Ala Ser Pro Ser Tyr Thr Ser
305                 310                 315                 320

Pro Asn Pro Asn Tyr Asp Glu Lys His Tyr Ile Glu Ala Phe Ala Pro
                325                 330                 335

Leu Leu Arg Asn Gln Gly Phe Asp Ala Lys Phe Ile Val Asp Thr Gly
            340                 345                 350

Arg Asn Gly Lys Gln Pro Thr Gly Gln Leu Glu Trp Gly His Trp Cys
            355                 360                 365

Asn Val Lys Gly Thr Gly Phe Gly Val Arg Pro Thr Ala Asn Thr Gly
            370                 375                 380

His Glu Leu Val Asp Ala Phe Val Trp Val Lys Pro Gly Gly Glu Ser
385                 390                 395                 400
```

```
Asp Gly Thr Ser Asp Ser Ser Ala Pro Arg Phe Asp Phe His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu His
        435                 440                 445

His His His His His
        450

<210> SEQ ID NO 17
<211> LENGTH: 1362
<212> TYPE: DNA
<213> ORGANISM: Artificial Sequence
<220> FEATURE:
<223> OTHER INFORMATION: Cel6a engineered variant 1G6
<220> FEATURE:
<221> NAME/KEY: CDS
<222> LOCATION: (1)..(1362)

<400> SEQUENCE: 17 gct agc tgc tca agc gtc tgg ggc caa tgt ggt ggc cag aat tgg tcg      48
Ala Ser Cys Ser Ser Val Trp Gly Gln Cys Gly Gly Gln Asn Trp Ser
1               5                   10                  15 ggt ccg act tgc tgt gct tcc gga agc aca tgc gtc tac tcc aac gac      96
Gly Pro Thr Cys Cys Ala Ser Gly Ser Thr Cys Val Tyr Ser Asn Asp
            20                  25                  30 tat tac tcc cag tgt ctt ccc ggc gct gca agc tca agc tcg tcc acg     144
Tyr Tyr Ser Gln Cys Leu Pro Gly Ala Ala Ser Ser Ser Ser Ser Thr
        35                  40                  45 cgc gcc gcg tcg acg act tct cga gta tcc ccc aca aca tcc cgg tcg     192
Arg Ala Ala Ser Thr Thr Ser Arg Val Ser Pro Thr Thr Ser Arg Ser
    50                  55                  60 agc tcc gcg acg cct cca cct ggt tct act act acc aga gta cct cca     240
Ser Ser Ala Thr Pro Pro Pro Gly Ser Thr Thr Thr Arg Val Pro Pro
65                  70                  75                  80 gtc gga tcg gga acc gct acg tat tca ggt aac ccc ttt gaa ggt gtt     288
Val Gly Ser Gly Thr Ala Thr Tyr Ser Gly Asn Pro Phe Glu Gly Val
                85                  90                  95 cag ctg tgg gct aat aac tat tat aga tct gag gta cat aca ctg gcc     336
Gln Leu Trp Ala Asn Asn Tyr Tyr Arg Ser Glu Val His Thr Leu Ala
            100                 105                 110 att ccg caa att aca gac ccc gcg ttg cgt gcc gca gct agt gct gtg     384
Ile Pro Gln Ile Thr Asp Pro Ala Leu Arg Ala Ala Ala Ser Ala Val
        115                 120                 125 gct gag gtg cca agt ttt atg tgg ctg gat act ttg gac aaa acc ccc     432
Ala Glu Val Pro Ser Phe Met Trp Leu Asp Thr Leu Asp Lys Thr Pro
    130                 135                 140 tta atg gaa caa acg ttg gct gat ata cgt act gcg aat aaa aac ggc     480
Leu Met Glu Gln Thr Leu Ala Asp Ile Arg Thr Ala Asn Lys Asn Gly
145                 150                 155                 160 ggc aat tat gct gga caa ttt gtg gtt tat gac ctg ccg gat aga gat     528
Gly Asn Tyr Ala Gly Gln Phe Val Val Tyr Asp Leu Pro Asp Arg Asp
                165                 170                 175 tgt gct gca cta gcg agc aac ggg gag tac agc att gcg gat ggc ggt     576
Cys Ala Ala Leu Ala Ser Asn Gly Glu Tyr Ser Ile Ala Asp Gly Gly
            180                 185                 190 gtc gca aag tac aaa aac tat ata gat act atc agg caa ata gtt gtc     624
Val Ala Lys Tyr Lys Asn Tyr Ile Asp Thr Ile Arg Gln Ile Val Val
        195                 200                 205 gaa tac agt gat att cgt acg ctg ctt gta atc gaa ccc gat tcc tta     672
```

```
                Glu Tyr Ser Asp Ile Arg Thr Leu Leu Val Ile Glu Pro Asp Ser Leu
                    210                 215                 220 gcg aac ttg gtg aca aat cta ggt act ccg aag tgt gcg aac gcg cag              720
Ala Asn Leu Val Thr Asn Leu Gly Thr Pro Lys Cys Ala Asn Ala Gln
225                 230                 235                 240 agt gct tat ctt gag tgc atc aat tat gca gtc acc cag ttg aat ttg              768
Ser Ala Tyr Leu Glu Cys Ile Asn Tyr Ala Val Thr Gln Leu Asn Leu
                245                 250                 255 cca aac gtt gca atg tat ctt gat gct ggt cat gcc ggg tgg ttg ggt              816
Pro Asn Val Ala Met Tyr Leu Asp Ala Gly His Ala Gly Trp Leu Gly
            260                 265                 270 tgg cca gca aat cag gat ccc gct gcg cag ctg ttt gca aat gtt tac              864
Trp Pro Ala Asn Gln Asp Pro Ala Ala Gln Leu Phe Ala Asn Val Tyr
        275                 280                 285 aaa aat gcc tca agt cct aga gcg ctg agg ggt ctt gca aca aat gtt              912
Lys Asn Ala Ser Ser Pro Arg Ala Leu Arg Gly Leu Ala Thr Asn Val
    290                 295                 300 gct aat tac aac gct tgg tca ata gcg agt cct cca ccg tac aca agc              960
Ala Asn Tyr Asn Ala Trp Ser Ile Ala Ser Pro Pro Pro Tyr Thr Ser
305                 310                 315                 320 cct aac cca aac tac gat gag aag cat tac ata gaa gca ttt gct cct             1008
Pro Asn Pro Asn Tyr Asp Glu Lys His Tyr Ile Glu Ala Phe Ala Pro
                325                 330                 335 ttg ctt cgt aac caa ggt ttt gat gca aag ttt atc gtc gat acc gga             1056
Leu Leu Arg Asn Gln Gly Phe Asp Ala Lys Phe Ile Val Asp Thr Gly
                340                 345                 350 aga aac ggc aag cag ccg aca ggg cag cta gaa tgg ggg cac tgg tgc             1104
Arg Asn Gly Lys Gln Pro Thr Gly Gln Leu Glu Trp Gly His Trp Cys
            355                 360                 365 aat gtc aag ggt acg ggt ttc ggt gtt aga ccc acg gct aac act ggg             1152
Asn Val Lys Gly Thr Gly Phe Gly Val Arg Pro Thr Ala Asn Thr Gly
        370                 375                 380 cat gag ttg gtt gat gca ttc gtt tgg gta aaa ccc gga gga gag tca             1200
His Glu Leu Val Asp Ala Phe Val Trp Val Lys Pro Gly Gly Glu Ser
385                 390                 395                 400 gat gga acg agt gat tct tct gct cca agg ttc gat tct cat tgc gca             1248
Asp Gly Thr Ser Asp Ser Ser Ala Pro Arg Phe Asp Ser His Cys Ala
                405                 410                 415 tta cca gat gct ttg cag cca gca cct caa gca gga gct tgg ttc caa             1296
Leu Pro Asp Ala Leu Gln Pro Ala Pro Gln Ala Gly Ala Trp Phe Gln
                420                 425                 430 gct tat ttt gta caa tta ctg act aac gcc aat cct agt ttt cta cat             1344
Ala Tyr Phe Val Gln Leu Leu Thr Asn Ala Asn Pro Ser Phe Leu His
            435                 440                 445 cac cat cac cac cat tag                                                     1362
His His His His His
    450

<210> SEQ ID NO 18
<211> LENGTH: 453
<212> TYPE: PRT
<213> ORGANISM: Artificial Sequence
<220> FEATURE:
<223> OTHER INFORMATION: Synthetic Construct

<400> SEQUENCE: 18

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30
```

Tyr Tyr Ser Gln Cys Leu Pro Gly Ala Ala Ser Ser Ser Ser Thr
            35                  40                  45

Arg Ala Ala Ser Thr Thr Ser Arg Val Ser Pro Thr Thr Ser Arg Ser
 50                  55                  60

Ser Ser Ala Thr Pro Pro Gly Ser Thr Thr Thr Arg Val Pro Pro
 65                  70                  75                  80

Val Gly Ser Gly Thr Ala Thr Tyr Ser Gly Asn Pro Phe Glu Gly Val
                     85                  90                  95

Gln Leu Trp Ala Asn Asn Tyr Tyr Arg Ser Glu Val His Thr Leu Ala
             100                 105                 110

Ile Pro Gln Ile Thr Asp Pro Ala Leu Arg Ala Ala Ser Ala Val
             115                 120                 125

Ala Glu Val Pro Ser Phe Met Trp Leu Asp Thr Leu Asp Lys Thr Pro
 130                 135                 140

Leu Met Glu Gln Thr Leu Ala Asp Ile Arg Thr Ala Asn Lys Asn Gly
 145                 150                 155                 160

Gly Asn Tyr Ala Gly Gln Phe Val Val Tyr Asp Leu Pro Asp Arg Asp
                     165                 170                 175

Cys Ala Ala Leu Ala Ser Asn Gly Glu Tyr Ser Ile Ala Asp Gly Gly
                 180                 185                 190

Val Ala Lys Tyr Lys Asn Tyr Ile Asp Thr Ile Arg Gln Ile Val Val
                 195                 200                 205

Glu Tyr Ser Asp Ile Arg Thr Leu Leu Val Ile Glu Pro Asp Ser Leu
     210                 215                 220

Ala Asn Leu Val Thr Asn Leu Gly Thr Pro Lys Cys Ala Asn Ala Gln
225                 230                 235                 240

Ser Ala Tyr Leu Glu Cys Ile Asn Tyr Ala Val Thr Gln Leu Asn Leu
                 245                 250                 255

Pro Asn Val Ala Met Tyr Leu Asp Ala Gly His Ala Gly Trp Leu Gly
                 260                 265                 270

Trp Pro Ala Asn Gln Asp Pro Ala Ala Gln Leu Phe Ala Asn Val Tyr
             275                 280                 285

Lys Asn Ala Ser Ser Pro Arg Ala Leu Arg Gly Leu Ala Thr Asn Val
 290                 295                 300

Ala Asn Tyr Asn Ala Trp Ser Ile Ala Ser Pro Pro Tyr Thr Ser
305                 310                 315                 320

Pro Asn Pro Asn Tyr Asp Glu Lys His Tyr Ile Glu Ala Phe Ala Pro
                 325                 330                 335

Leu Leu Arg Asn Gln Gly Phe Asp Ala Lys Phe Ile Val Asp Thr Gly
             340                 345                 350

Arg Asn Gly Lys Gln Pro Thr Gly Gln Leu Glu Trp Gly His Trp Cys
             355                 360                 365

Asn Val Lys Gly Thr Gly Phe Gly Val Arg Pro Thr Ala Asn Thr Gly
 370                 375                 380

His Glu Leu Val Asp Ala Phe Val Trp Val Lys Pro Gly Gly Glu Ser
385                 390                 395                 400

Asp Gly Thr Ser Asp Ser Ser Ala Pro Arg Phe Asp Ser His Cys Ala
                 405                 410                 415

Leu Pro Asp Ala Leu Gln Pro Ala Pro Gln Ala Gly Ala Trp Phe Gln
                 420                 425                 430

Ala Tyr Phe Val Gln Leu Leu Thr Asn Ala Asn Pro Ser Phe Leu His
                 435                 440                 445

His His His His His

<210> SEQ ID NO 19
<211> LENGTH: 1362
<212> TYPE: DNA
<213> ORGANISM: Artificial Sequence
<220> FEATURE:
<223> OTHER INFORMATION: Cel6a engineered variant 2B3
<220> FEATURE:
<221> NAME/KEY: CDS
<222> LOCATION: (1)..(1362)

<400> SEQUENCE: 19

| | | | | | | | | | | | | | | | | |
|---|---|---|---|---|---|---|---|---|---|---|---|---|---|---|---|---|
| gct | agc | tgc | tca | agc | gtc | tgg | ggc | caa | tgt | ggt | ggc | cag | aat | tgg | tcg | 48 |
| Ala | Ser | Cys | Ser | Ser | Val | Trp | Gly | Gln | Cys | Gly | Gly | Gln | Asn | Trp | Ser | |
| 1 | | | | 5 | | | | | 10 | | | | | 15 | | |
| ggt | ccg | acc | tgc | tgt | gct | tcc | gga | agc | aca | tgc | gtc | tac | tcc | aac | gac | 96 |
| Gly | Pro | Thr | Cys | Cys | Ala | Ser | Gly | Ser | Thr | Cys | Val | Tyr | Ser | Asn | Asp | |
| | | 20 | | | | | 25 | | | | | 30 | | | | |
| tat | tac | tcc | cag | tgt | ctt | ccc | ggc | gct | gca | agc | tca | agc | tcg | tcc | acg | 144 |
| Tyr | Tyr | Ser | Gln | Cys | Leu | Pro | Gly | Ala | Ala | Ser | Ser | Ser | Ser | Ser | Thr | |
| | | 35 | | | | | 40 | | | | | 45 | | | | |
| cgc | gcc | gcg | tcg | acg | act | tct | cga | gta | tcc | ccc | aca | aca | tcc | cgg | tcg | 192 |
| Arg | Ala | Ala | Ser | Thr | Thr | Ser | Arg | Val | Ser | Pro | Thr | Thr | Ser | Arg | Ser | |
| 50 | | | | | 55 | | | | | 60 | | | | | | |
| agc | tcc | gcg | acg | cct | cca | cct | ggt | tct | act | act | acc | aga | gta | cct | cca | 240 |
| Ser | Ser | Ala | Thr | Pro | Pro | Pro | Gly | Ser | Thr | Thr | Thr | Arg | Val | Pro | Pro | |
| 65 | | | | | 70 | | | | | 75 | | | | | 80 | |
| gtc | gga | tcg | gga | acc | gct | acg | tat | tca | ggt | aac | ccc | ttt | gaa | ggt | gtt | 288 |
| Val | Gly | Ser | Gly | Thr | Ala | Thr | Tyr | Ser | Gly | Asn | Pro | Phe | Glu | Gly | Val | |
| | | | | 85 | | | | | 90 | | | | | 95 | | |
| cag | ctg | tgg | gct | aat | aac | tat | tat | aga | tct | gag | gta | cat | aca | ctg | gcc | 336 |
| Gln | Leu | Trp | Ala | Asn | Asn | Tyr | Tyr | Arg | Ser | Glu | Val | His | Thr | Leu | Ala | |
| | | | 100 | | | | | 105 | | | | | 110 | | | |
| att | ccg | caa | att | aca | gac | ccc | gcg | ttg | cgt | gcc | gca | gct | agt | gct | gtg | 384 |
| Ile | Pro | Gln | Ile | Thr | Asp | Pro | Ala | Leu | Arg | Ala | Ala | Ala | Ser | Ala | Val | |
| | | 115 | | | | | 120 | | | | | 125 | | | | |
| gct | gag | gtg | cca | agt | ttt | atg | tgg | ctg | gat | act | ttg | gac | aaa | acc | ccc | 432 |
| Ala | Glu | Val | Pro | Ser | Phe | Met | Trp | Leu | Asp | Thr | Leu | Asp | Lys | Thr | Pro | |
| 130 | | | | | 135 | | | | | 140 | | | | | | |
| tta | atg | gaa | caa | acg | ttg | gct | gat | ata | cgt | act | gcg | aat | aaa | aac | ggc | 480 |
| Leu | Met | Glu | Gln | Thr | Leu | Ala | Asp | Ile | Arg | Thr | Ala | Asn | Lys | Asn | Gly | |
| 145 | | | | | 150 | | | | | 155 | | | | | 160 | |
| ggc | aat | tat | gct | gga | caa | ttt | gtg | gtt | tat | gac | ctg | ccg | gat | aga | gat | 528 |
| Gly | Asn | Tyr | Ala | Gly | Gln | Phe | Val | Val | Tyr | Asp | Leu | Pro | Asp | Arg | Asp | |
| | | | 165 | | | | | 170 | | | | | 175 | | | |
| tgt | gct | gca | cta | gcg | agc | aac | ggg | gag | tac | agc | att | gcg | gat | ggc | ggt | 576 |
| Cys | Ala | Ala | Leu | Ala | Ser | Asn | Gly | Glu | Tyr | Ser | Ile | Ala | Asp | Gly | Gly | |
| | | 180 | | | | | 185 | | | | | 190 | | | | |
| gtc | gca | aag | tac | aaa | aac | tat | ata | gat | act | atc | agg | caa | ata | gtt | gtc | 624 |
| Val | Ala | Lys | Tyr | Lys | Asn | Tyr | Ile | Asp | Thr | Ile | Arg | Gln | Ile | Val | Val | |
| | | 195 | | | | | 200 | | | | | 205 | | | | |
| gaa | tac | agt | gat | att | cgt | acg | ctg | ctt | gta | atc | gaa | ccc | gat | tcc | tta | 672 |
| Glu | Tyr | Ser | Asp | Ile | Arg | Thr | Leu | Leu | Val | Ile | Glu | Pro | Asp | Ser | Leu | |
| 210 | | | | | 215 | | | | | 220 | | | | | | |
| gcg | aac | ttg | gta | aca | aat | cta | ggt | act | ccg | aag | tgt | gcg | aac | gcg | cag | 720 |
| Ala | Asn | Leu | Val | Thr | Asn | Leu | Gly | Thr | Pro | Lys | Cys | Ala | Asn | Ala | Gln | |
| 225 | | | | | 230 | | | | | 235 | | | | | 240 | |
| agt | gct | tat | ctt | gag | tgc | atc | aat | tat | gca | gtc | acc | cag | ttg | aat | ttg | 768 |
| Ser | Ala | Tyr | Leu | Glu | Cys | Ile | Asn | Tyr | Ala | Val | Thr | Gln | Leu | Asn | Leu | |
| | | | 245 | | | | | 250 | | | | | 255 | | | |

| | | |
|---|---|---|
| cca aac gtt gca atg tat ctt gat gct ggt cat gcc ggg tgg ttg ggt<br>Pro Asn Val Ala Met Tyr Leu Asp Ala Gly His Ala Gly Trp Leu Gly<br>           260                        265                    270 | | 816 |
| tgg cca gca aat ctg gat ccc gct gcg cag ctg ttt gca aat gtt tac<br>Trp Pro Ala Asn Leu Asp Pro Ala Ala Gln Leu Phe Ala Asn Val Tyr<br>           275                       280                    285 | | 864 |
| aaa aat gcc tca agt cct aga gcg ctg agg ggt ctt gca aca aat gtt<br>Lys Asn Ala Ser Ser Pro Arg Ala Leu Arg Gly Leu Ala Thr Asn Val<br>    290                       295                    300 | | 912 |
| gct aat tac aac gct tgg tca ata gcg agt ccc cca ccg tac aca agc<br>Ala Asn Tyr Asn Ala Trp Ser Ile Ala Ser Pro Pro Pro Tyr Thr Ser<br>305                    310                    315                    320 | | 960 |
| cct aac cca aac tac gat gag aag cat tac ata gaa gca ttt gct cct<br>Pro Asn Pro Asn Tyr Asp Glu Lys His Tyr Ile Glu Ala Phe Ala Pro<br>                  325                    330                    335 | | 1008 |
| ttg ctt cgt aac caa ggt ttt gat gca aag ttt atc gtc gat acc gga<br>Leu Leu Arg Asn Gln Gly Phe Asp Ala Lys Phe Ile Val Asp Thr Gly<br>           340                       345                    350 | | 1056 |
| aga aac ggc aag cag ccg aca ggg cag cta gaa tgg ggg cac tgg tgc<br>Arg Asn Gly Lys Gln Pro Thr Gly Gln Leu Glu Trp Gly His Trp Cys<br>        355                       360                    365 | | 1104 |
| aat gtc aag ggt acg ggt ttc ggt gtt aga ccc acg gct aac act ggg<br>Asn Val Lys Gly Thr Gly Phe Gly Val Arg Pro Thr Ala Asn Thr Gly<br>370                    375                    380 | | 1152 |
| cat gag ttg gtt gat gca ttc gtt tgg gta aaa ccc gga gga gag tca<br>His Glu Leu Val Asp Ala Phe Val Trp Val Lys Pro Gly Gly Glu Ser<br>385                    390                    395                    400 | | 1200 |
| gat gga acg agt gat tct tct gct cca agg ttc gat tct cat tgc gca<br>Asp Gly Thr Ser Asp Ser Ser Ala Pro Arg Phe Asp Ser His Cys Ala<br>                  405                    410                    415 | | 1248 |
| tta cca gat gct ttg cag cca gca cct caa gca gga gct tgg ttc caa<br>Leu Pro Asp Ala Leu Gln Pro Ala Pro Gln Ala Gly Ala Trp Phe Gln<br>           420                       425                    430 | | 1296 |
| gct tat ttt gta caa tta ctg act aac gcc aat cct agt ttt cta cat<br>Ala Tyr Phe Val Gln Leu Leu Thr Asn Ala Asn Pro Ser Phe Leu His<br>        435                       440                    445 | | 1344 |
| cac cat cac cac cat tag<br>His His His His His<br>    450 | | 1362 |

<210> SEQ ID NO 20
<211> LENGTH: 453
<212> TYPE: PRT
<213> ORGANISM: Artificial Sequence
<220> FEATURE:
<223> OTHER INFORMATION: Synthetic Construct

<400> SEQUENCE: 20

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Glu Gly Val
                85                  90                  95

Gln Leu Trp Ala Asn Asn Tyr Tyr Arg Ser Glu Val His Thr Leu Ala
            100                 105                 110

Ile Pro Gln Ile Thr Asp Pro Ala Leu Arg Ala Ala Ser Ala Val
        115                 120                 125

Ala Glu Val Pro Ser Phe Met Trp Leu Asp Thr Leu Asp Lys Thr Pro
130                 135                 140

Leu Met Glu Gln Thr Leu Ala Asp Ile Arg Thr Ala Asn Lys Asn Gly
145                 150                 155                 160

Gly Asn Tyr Ala Gly Gln Phe Val Val Tyr Asp Leu Pro Asp Arg Asp
                165                 170                 175

Cys Ala Ala Leu Ala Ser Asn Gly Glu Tyr Ser Ile Ala Asp Gly Gly
                180                 185                 190

Val Ala Lys Tyr Lys Asn Tyr Ile Asp Thr Ile Arg Gln Ile Val Val
            195                 200                 205

Glu Tyr Ser Asp Ile Arg Thr Leu Leu Val Ile Glu Pro Asp Ser Leu
    210                 215                 220

Ala Asn Leu Val Thr Asn Leu Gly Thr Pro Lys Cys Ala Asn Ala Gln
225                 230                 235                 240

Ser Ala Tyr Leu Glu Cys Ile Asn Tyr Ala Val Thr Gln Leu Asn Leu
                245                 250                 255

Pro Asn Val Ala Met Tyr Leu Asp Ala Gly His Ala Gly Trp Leu Gly
                260                 265                 270

Trp Pro Ala Asn Leu Asp Pro Ala Ala Gln Leu Phe Ala Asn Val Tyr
            275                 280                 285

Lys Asn Ala Ser Ser Pro Arg Ala Leu Arg Gly Leu Ala Thr Asn Val
    290                 295                 300

Ala Asn Tyr Asn Ala Trp Ser Ile Ala Ser Pro Pro Tyr Thr Ser
305                 310                 315                 320

Pro Asn Pro Asn Tyr Asp Glu Lys His Tyr Ile Glu Ala Phe Ala Pro
                325                 330                 335

Leu Leu Arg Asn Gln Gly Phe Asp Ala Lys Phe Ile Val Asp Thr Gly
            340                 345                 350

Arg Asn Gly Lys Gln Pro Thr Gly Gln Leu Glu Trp Gly His Trp Cys
    355                 360                 365

Asn Val Lys Gly Thr Gly Phe Gly Val Arg Pro Thr Ala Asn Thr Gly
370                 375                 380

His Glu Leu Val Asp Ala Phe Val Trp Val Lys Pro Gly Gly Glu Ser
385                 390                 395                 400

Asp Gly Thr Ser Asp Ser Ser Ala Pro Arg Phe Asp Ser His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu His
    435                 440                 445

His His His His
    450

<210> SEQ ID NO 21
<211> LENGTH: 1362
<212> TYPE: DNA
<213> ORGANISM: Artificial Sequence
<220> FEATURE:
<223> OTHER INFORMATION: Cel6a engineered variant 2F4
<220> FEATURE:
<221> NAME/KEY: CDS

<222> LOCATION: (1)..(1362)

<400> SEQUENCE: 21

| | | | | | | | | | | | | | | | | |
|---|---|---|---|---|---|---|---|---|---|---|---|---|---|---|---|---|
| gct | agc | tgc | tca | agc | gtc | tgg | ggc | caa | tgt | ggt | ggc | cag | aat | tgg | tcg | 48 |
| Ala | Ser | Cys | Ser | Ser | Val | Trp | Gly | Gln | Cys | Gly | Gly | Gln | Asn | Trp | Ser | |
| 1 | | | | 5 | | | | | 10 | | | | | 15 | | |

| ggt | ccg | act | tgc | tgt | gct | tcc | gga | agc | aca | tgc | gtc | tac | tcc | aac | gac | 96 |
|---|---|---|---|---|---|---|---|---|---|---|---|---|---|---|---|---|
| Gly | Pro | Thr | Cys | Cys | Ala | Ser | Gly | Ser | Thr | Cys | Val | Tyr | Ser | Asn | Asp | |
| | | 20 | | | | | 25 | | | | | 30 | | | | |

| tat | tac | tcc | cag | tgt | ctt | ccc | ggc | gct | gca | agc | tca | agc | tcg | tcc | acg | 144 |
|---|---|---|---|---|---|---|---|---|---|---|---|---|---|---|---|---|
| Tyr | Tyr | Ser | Gln | Cys | Leu | Pro | Gly | Ala | Ala | Ser | Ser | Ser | Ser | Ser | Thr | |
| | | 35 | | | | 40 | | | | | 45 | | | | | |

| cgc | gcc | gcg | tcg | acg | act | tct | cga | gta | tcc | ccc | aca | aca | tcc | cgg | tcg | 192 |
|---|---|---|---|---|---|---|---|---|---|---|---|---|---|---|---|---|
| Arg | Ala | Ala | Ser | Thr | Thr | Ser | Arg | Val | Ser | Pro | Thr | Thr | Ser | Arg | Ser | |
| 50 | | | | | 55 | | | | | 60 | | | | | | |

| agc | tcc | gcg | acg | cct | cca | cct | ggt | tct | act | act | acc | aga | gta | cct | cca | 240 |
|---|---|---|---|---|---|---|---|---|---|---|---|---|---|---|---|---|
| Ser | Ser | Ala | Thr | Pro | Pro | Pro | Gly | Ser | Thr | Thr | Thr | Arg | Val | Pro | Pro | |
| 65 | | | | 70 | | | | | 75 | | | | | 80 | | |

| gtc | gga | tcg | gga | acc | gct | acg | tat | tca | ggt | aac | ccc | ttt | gaa | ggt | gtt | 288 |
|---|---|---|---|---|---|---|---|---|---|---|---|---|---|---|---|---|
| Val | Gly | Ser | Gly | Thr | Ala | Thr | Tyr | Ser | Gly | Asn | Pro | Phe | Glu | Gly | Val | |
| | | | | 85 | | | | | 90 | | | | | 95 | | |

| cag | ctg | tgg | gct | aat | aac | tat | tat | aga | tct | gag | gta | cat | aca | ctg | gcc | 336 |
|---|---|---|---|---|---|---|---|---|---|---|---|---|---|---|---|---|
| Gln | Leu | Trp | Ala | Asn | Asn | Tyr | Tyr | Arg | Ser | Glu | Val | His | Thr | Leu | Ala | |
| | | | 100 | | | | | 105 | | | | | 110 | | | |

| att | ccg | caa | att | aca | gac | ccc | gcg | ttg | cgt | gcc | gca | gct | agt | gct | gtg | 384 |
|---|---|---|---|---|---|---|---|---|---|---|---|---|---|---|---|---|
| Ile | Pro | Gln | Ile | Thr | Asp | Pro | Ala | Leu | Arg | Ala | Ala | Ala | Ser | Ala | Val | |
| | | | 115 | | | | | 120 | | | | | 125 | | | |

| gct | gag | gtg | cca | agt | ttt | ttg | tgg | ctg | gat | act | ttg | gac | aaa | acc | ccc | 432 |
|---|---|---|---|---|---|---|---|---|---|---|---|---|---|---|---|---|
| Ala | Glu | Val | Pro | Ser | Phe | Leu | Trp | Leu | Asp | Thr | Leu | Asp | Lys | Thr | Pro | |
| 130 | | | | | 135 | | | | | 140 | | | | | | |

| tta | atg | gaa | caa | acg | ttg | gct | gat | ata | cgt | act | gcg | aat | aaa | aac | ggc | 480 |
|---|---|---|---|---|---|---|---|---|---|---|---|---|---|---|---|---|
| Leu | Met | Glu | Gln | Thr | Leu | Ala | Asp | Ile | Arg | Thr | Ala | Asn | Lys | Asn | Gly | |
| 145 | | | | | 150 | | | | | 155 | | | | | 160 | |

| ggc | aat | tat | gct | gga | caa | ttt | gtg | gtt | tat | gac | ctg | ccg | gat | aga | gat | 528 |
|---|---|---|---|---|---|---|---|---|---|---|---|---|---|---|---|---|
| Gly | Asn | Tyr | Ala | Gly | Gln | Phe | Val | Val | Tyr | Asp | Leu | Pro | Asp | Arg | Asp | |
| | | | | 165 | | | | | 170 | | | | | 175 | | |

| tgt | gct | gca | cta | gcg | agc | aac | ggg | gag | tac | agc | att | gcg | gat | ggc | ggt | 576 |
|---|---|---|---|---|---|---|---|---|---|---|---|---|---|---|---|---|
| Cys | Ala | Ala | Leu | Ala | Ser | Asn | Gly | Glu | Tyr | Ser | Ile | Ala | Asp | Gly | Gly | |
| | | | | 180 | | | | | 185 | | | | | 190 | | |

| gtc | gca | aag | tac | aaa | aac | tat | ata | gat | act | atc | agg | caa | ata | gtt | gtc | 624 |
|---|---|---|---|---|---|---|---|---|---|---|---|---|---|---|---|---|
| Val | Ala | Lys | Tyr | Lys | Asn | Tyr | Ile | Asp | Thr | Ile | Arg | Gln | Ile | Val | Val | |
| | | 195 | | | | | 200 | | | | | 205 | | | | |

| gaa | tac | agt | gat | att | cgt | acg | ctg | ctt | gta | atc | gaa | ccc | gat | tcc | tta | 672 |
|---|---|---|---|---|---|---|---|---|---|---|---|---|---|---|---|---|
| Glu | Tyr | Ser | Asp | Ile | Arg | Thr | Leu | Leu | Val | Ile | Glu | Pro | Asp | Ser | Leu | |
| 210 | | | | | 215 | | | | | 220 | | | | | | |

| gcg | aac | ttg | gtg | aca | aat | cta | ggt | act | ccg | aag | tgt | gcg | aac | gcg | cag | 720 |
|---|---|---|---|---|---|---|---|---|---|---|---|---|---|---|---|---|
| Ala | Asn | Leu | Val | Thr | Asn | Leu | Gly | Thr | Pro | Lys | Cys | Ala | Asn | Ala | Gln | |
| 225 | | | | | 230 | | | | | 235 | | | | | 240 | |

| agt | gct | tat | ctt | gag | tgc | atc | aat | tat | gca | gtc | acc | cag | ttg | aat | ttg | 768 |
|---|---|---|---|---|---|---|---|---|---|---|---|---|---|---|---|---|
| Ser | Ala | Tyr | Leu | Glu | Cys | Ile | Asn | Tyr | Ala | Val | Thr | Gln | Leu | Asn | Leu | |
| | | | | 245 | | | | | 250 | | | | | 255 | | |

| cca | aac | gtt | gca | atg | tat | ctt | gat | gct | ggt | cat | gcc | ggg | tgg | ttg | ggt | 816 |
|---|---|---|---|---|---|---|---|---|---|---|---|---|---|---|---|---|
| Pro | Asn | Val | Ala | Met | Tyr | Leu | Asp | Ala | Gly | His | Ala | Gly | Trp | Leu | Gly | |
| | | | | 260 | | | | | 265 | | | | | 270 | | |

| tgg | cca | gca | aat | cag | gat | ccc | gct | gcg | cag | ctg | ttt | gca | aat | gtt | tac | 864 |
|---|---|---|---|---|---|---|---|---|---|---|---|---|---|---|---|---|
| Trp | Pro | Ala | Asn | Gln | Asp | Pro | Ala | Ala | Gln | Leu | Phe | Ala | Asn | Val | Tyr | |
| | | 275 | | | | | 280 | | | | | 285 | | | | |

| aaa | aat | gcc | tca | agt | cct | aga | gcg | ctg | agg | ggt | ctt | gca | aca | aat | gtt | 912 |
|---|---|---|---|---|---|---|---|---|---|---|---|---|---|---|---|---|
| Lys | Asn | Ala | Ser | Ser | Pro | Arg | Ala | Leu | Arg | Gly | Leu | Ala | Thr | Asn | Val | |
| | 290 | | | | | 295 | | | | | 300 | | | | | |

```
gct aat tac aac gct tgg tca ata gcg agt cct cca ccg tac aca agc      960
Ala Asn Tyr Asn Ala Trp Ser Ile Ala Ser Pro Pro Pro Tyr Thr Ser
305                 310                 315                 320 cct aac cca aac tac gat gag aag cat tac ata gaa gca ttt gct cct     1008
Pro Asn Pro Asn Tyr Asp Glu Lys His Tyr Ile Glu Ala Phe Ala Pro
                325                 330                 335 ttg ctt cgt aac caa ggt ttt gat gca aag ttt atc gtc gat acc gga     1056
Leu Leu Arg Asn Gln Gly Phe Asp Ala Lys Phe Ile Val Asp Thr Gly
            340                 345                 350 aga aac ggc aag cag ccg aca ggg cag cta gaa tgg ggg cac tgg tgc     1104
Arg Asn Gly Lys Gln Pro Thr Gly Gln Leu Glu Trp Gly His Trp Cys
        355                 360                 365 aat gtc aag ggt acg ggt ttc ggt gtt aga ccc acg gct aac act ggg     1152
Asn Val Lys Gly Thr Gly Phe Gly Val Arg Pro Thr Ala Asn Thr Gly
    370                 375                 380 cat gag ttg gtt gat gca ttc gtt tgg gta aaa ccc gga gga gag tca     1200
His Glu Leu Val Asp Ala Phe Val Trp Val Lys Pro Gly Gly Glu Ser
385                 390                 395                 400 gat gga acg agt gat tct tct gct cca agg ttc gat tct cat tgc gca     1248
Asp Gly Thr Ser Asp Ser Ser Ala Pro Arg Phe Asp Ser His Cys Ala
                405                 410                 415 tta cca gat gct ttg cag cca gca cct caa gca gga gct tgg ttc caa     1296
Leu Pro Asp Ala Leu Gln Pro Ala Pro Gln Ala Gly Ala Trp Phe Gln
            420                 425                 430 gct tat ttt gta caa tta ctg act aac gcc aat cct agt ttt cta cat     1344
Ala Tyr Phe Val Gln Leu Leu Thr Asn Ala Asn Pro Ser Phe Leu His
        435                 440                 445 cac cat cac cac cat tag                                             1362
His His His His His
    450

<210> SEQ ID NO 22
<211> LENGTH: 453
<212> TYPE: PRT
<213> ORGANISM: Artificial Sequence
<220> FEATURE:
<223> OTHER INFORMATION: Synthetic Construct

<400> SEQUENCE: 22

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Glu Gly Val
                85                  90                  95

Gln Leu Trp Ala Asn Asn Tyr Tyr Arg Ser Glu Val His Thr Leu Ala
            100                 105                 110

Ile Pro Gln Ile Thr Asp Pro Ala Leu Arg Ala Ala Ser Ala Val
        115                 120                 125

Ala Glu Val Pro Ser Phe Leu Trp Leu Asp Thr Leu Asp Lys Thr Pro
    130                 135                 140

Leu Met Glu Gln Thr Leu Ala Asp Ile Arg Thr Ala Asn Lys Asn Gly
```

```
                145                 150                 155                 160
        Gly Asn Tyr Ala Gly Gln Phe Val Val Tyr Asp Leu Pro Asp Arg Asp
                        165                 170                 175

Cys Ala Ala Leu Ala Ser Asn Gly Glu Tyr Ser Ile Ala Asp Gly Gly
                        180                 185                 190

Val Ala Lys Tyr Lys Asn Tyr Ile Asp Thr Ile Arg Gln Ile Val Val
                        195                 200                 205

Glu Tyr Ser Asp Ile Arg Thr Leu Leu Val Ile Glu Pro Asp Ser Leu
                210                 215                 220

Ala Asn Leu Val Thr Asn Leu Gly Thr Pro Lys Cys Ala Asn Ala Gln
        225                 230                 235                 240

Ser Ala Tyr Leu Glu Cys Ile Asn Tyr Ala Val Thr Gln Leu Asn Leu
                        245                 250                 255

Pro Asn Val Ala Met Tyr Leu Asp Ala Gly His Ala Gly Trp Leu Gly
                        260                 265                 270

Trp Pro Ala Asn Gln Asp Pro Ala Ala Gln Leu Phe Ala Asn Val Tyr
                        275                 280                 285

Lys Asn Ala Ser Ser Pro Arg Ala Leu Arg Gly Leu Ala Thr Asn Val
                        290                 295                 300

Ala Asn Tyr Asn Ala Trp Ser Ile Ala Ser Pro Pro Tyr Thr Ser
        305                 310                 315                 320

Pro Asn Pro Asn Tyr Asp Glu Lys His Tyr Ile Glu Ala Phe Ala Pro
                        325                 330                 335

Leu Leu Arg Asn Gln Gly Phe Asp Ala Lys Phe Ile Val Asp Thr Gly
                        340                 345                 350

Arg Asn Gly Lys Gln Pro Thr Gly Gln Leu Glu Trp Gly His Trp Cys
                        355                 360                 365

Asn Val Lys Gly Thr Gly Phe Gly Val Arg Pro Thr Ala Asn Thr Gly
                        370                 375                 380

His Glu Leu Val Asp Ala Phe Val Trp Val Lys Pro Gly Gly Glu Ser
        385                 390                 395                 400

Asp Gly Thr Ser Asp Ser Ser Ala Pro Arg Phe Asp Ser His Cys Ala
                        405                 410                 415

Leu Pro Asp Ala Leu Gln Pro Ala Pro Gln Ala Gly Ala Trp Phe Gln
                        420                 425                 430

Ala Tyr Phe Val Gln Leu Leu Thr Asn Ala Asn Pro Ser Phe Leu His
                        435                 440                 445

His His His His His
                450

<210> SEQ ID NO 23
<211> LENGTH: 1362
<212> TYPE: DNA
<213> ORGANISM: Artificial Sequence
<220> FEATURE:
<223> OTHER INFORMATION: Cel6a engineered variant 2G6
<220> FEATURE:
<221> NAME/KEY: CDS
<222> LOCATION: (1)..(1362)

<400> SEQUENCE: 23 gct agc tgc tca agc gtc tgg ggc caa tgt ggt ggc cag aat tgg tcg        48
Ala Ser Cys Ser Ser Val Trp Gly Gln Cys Gly Gly Gln Asn Trp Ser
1               5                   10                  15 ggt ccg act tgc tgt gct tcc gga agc aca tgc gtc tac tcc aac gac        96
Gly Pro Thr Cys Cys Ala Ser Gly Ser Thr Cys Val Tyr Ser Asn Asp
                20                  25                  30
```

```
tat tac tcc cag tgt ctt ccc ggc gct gca agc tca agc tcg tcc acg      144
Tyr Tyr Ser Gln Cys Leu Pro Gly Ala Ala Ser Ser Ser Ser Ser Thr
             35                  40                  45 cgc gcc gcg tcg acg act tct cga gta tcc ccc aca aca tcc cgg tcg      192
Arg Ala Ala Ser Thr Thr Ser Arg Val Ser Pro Thr Thr Ser Arg Ser
 50                  55                  60 agc tcc gcg acg cct cca cct ggt tct act act acc aga gta cct cca      240
Ser Ser Ala Thr Pro Pro Pro Gly Ser Thr Thr Thr Arg Val Pro Pro
 65                  70                  75                  80 gtc gga tcg gga acc gct acg tat tca ggt aac ccc ttt gaa ggt gtt      288
Val Gly Ser Gly Thr Ala Thr Tyr Ser Gly Asn Pro Phe Glu Gly Val
                     85                  90                  95 cag ctg tgg gct aat aac tat tat aga tct gag gta cat aca ctg gcc      336
Gln Leu Trp Ala Asn Asn Tyr Tyr Arg Ser Glu Val His Thr Leu Ala
                100                 105                 110 att ccg caa att aca gac ccc gcg ttg cgt gcc gca gct agt gct gtg      384
Ile Pro Gln Ile Thr Asp Pro Ala Leu Arg Ala Ala Ala Ser Ala Val
            115                 120                 125 gct gag gtg cca agt ttt atg tgg ctg gat act ttg gac aaa acc ccc      432
Ala Glu Val Pro Ser Phe Met Trp Leu Asp Thr Leu Asp Lys Thr Pro
130                 135                 140 tta atg gaa caa acg ttg gct gat ata cgt act gcg aat aaa aac ggc      480
Leu Met Glu Gln Thr Leu Ala Asp Ile Arg Thr Ala Asn Lys Asn Gly
145                 150                 155                 160 ggc aat tat gct gga caa ttt gtg gtt tat gac ctg ccg gat aga gat      528
Gly Asn Tyr Ala Gly Gln Phe Val Val Tyr Asp Leu Pro Asp Arg Asp
                165                 170                 175 tgt gct gca cta gcg agc aac ggg gag tac agc att gcg gat ggc ggt      576
Cys Ala Ala Leu Ala Ser Asn Gly Glu Tyr Ser Ile Ala Asp Gly Gly
                180                 185                 190 gtc gca aag tac aaa aac tat ata gat act atc agg caa ata gtt gtc      624
Val Ala Lys Tyr Lys Asn Tyr Ile Asp Thr Ile Arg Gln Ile Val Val
            195                 200                 205 gaa tac agt gat att cgt acg ctg ctt gta atc gaa ccc gat tcc tta      672
Glu Tyr Ser Asp Ile Arg Thr Leu Leu Val Ile Glu Pro Asp Ser Leu
210                 215                 220 gcg aac ttg gtg aca aat cta ggt act ccg aag tgt gcg aac gcg cag      720
Ala Asn Leu Val Thr Asn Leu Gly Thr Pro Lys Cys Ala Asn Ala Gln
225                 230                 235                 240 agt gct tat ctt gag tgc atc aat tat gca gtc acc cag ttg aat ttg      768
Ser Ala Tyr Leu Glu Cys Ile Asn Tyr Ala Val Thr Gln Leu Asn Leu
                245                 250                 255 cca aac gtt gca atg tat ctt gat gct ggt cat gcc ggg tgg ttg ggt      816
Pro Asn Val Ala Met Tyr Leu Asp Ala Gly His Ala Gly Trp Leu Gly
                260                 265                 270 tgg cca gca aat cag gat ccc gct gcg cag ctg ttt gca aat gtt tac      864
Trp Pro Ala Asn Gln Asp Pro Ala Ala Gln Leu Phe Ala Asn Val Tyr
            275                 280                 285 aaa aat gcc tca agt cct aga gcg ctg agg ggt ctt gca aca aat gtt      912
Lys Asn Ala Ser Ser Pro Arg Ala Leu Arg Gly Leu Ala Thr Asn Val
290                 295                 300 gct aat tac aac gct tgg tca ata gcg agt cct cca ccg tac aca agc      960
Ala Asn Tyr Asn Ala Trp Ser Ile Ala Ser Pro Pro Pro Tyr Thr Ser
305                 310                 315                 320 cct aac cca aac tac gat gag aag cat tac ata gaa gca ttt gct cct     1008
Pro Asn Pro Asn Tyr Asp Glu Lys His Tyr Ile Glu Ala Phe Ala Pro
                325                 330                 335 ttg ctt cgt aac caa ggt ttt gat gca aag ttt atc gtc gat acc gga     1056
Leu Leu Arg Asn Gln Gly Phe Asp Ala Lys Phe Ile Val Asp Thr Gly
```

```
                    340                 345                 350
aga aac ggc aag cag ccg aca ggg cag cta gaa tgg ggg cac tgg tgc    1104
Arg Asn Gly Lys Gln Pro Thr Gly Gln Leu Glu Trp Gly His Trp Cys
        355                 360                 365 aat gtc aag ggt acg ggt ttc ggt gtt aga ccc acg gct aac act ggg    1152
Asn Val Lys Gly Thr Gly Phe Gly Val Arg Pro Thr Ala Asn Thr Gly
370                 375                 380 cat gag ttg gtt gat gca ttc gtt tgg gta aaa ccc gga gga gag tca    1200
His Glu Leu Val Asp Ala Phe Val Trp Val Lys Pro Gly Gly Glu Ser
385                 390                 395                 400 gat gga acg agt gat cct tct gct cca agg ttc gat tct cat tgc gca    1248
Asp Gly Thr Ser Asp Pro Ser Ala Pro Arg Phe Asp Ser His Cys Ala
            405                 410                 415 tta cca gat gct ttg cag cca gca cct caa gca gga gct tgg ttc caa    1296
Leu Pro Asp Ala Leu Gln Pro Ala Pro Gln Ala Gly Ala Trp Phe Gln
                420                 425                 430 gct tat ttt gta caa tta ctg act aac gcc aat cct agt ttt cta cat    1344
Ala Tyr Phe Val Gln Leu Leu Thr Asn Ala Asn Pro Ser Phe Leu His
            435                 440                 445 cac cat cac cac cat tag                                             1362
His His His His His
    450

<210> SEQ ID NO 24
<211> LENGTH: 453
<212> TYPE: PRT
<213> ORGANISM: Artificial Sequence
<220> FEATURE:
<223> OTHER INFORMATION: Synthetic Construct

<400> SEQUENCE: 24

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Glu Gly Val
                85                  90                  95

Gln Leu Trp Ala Asn Asn Tyr Tyr Arg Ser Glu Val His Thr Leu Ala
            100                 105                 110

Ile Pro Gln Ile Thr Asp Pro Ala Leu Arg Ala Ala Ser Ala Val
        115                 120                 125

Ala Glu Val Pro Ser Phe Met Trp Leu Asp Thr Leu Asp Lys Thr Pro
    130                 135                 140

Leu Met Glu Gln Thr Leu Ala Asp Ile Arg Thr Ala Asn Lys Asn Gly
145                 150                 155                 160

Gly Asn Tyr Ala Gly Gln Phe Val Val Tyr Asp Leu Pro Asp Arg Asp
                165                 170                 175

Cys Ala Ala Leu Ala Ser Asn Gly Glu Tyr Ser Ile Ala Asp Gly Gly
            180                 185                 190

Val Ala Lys Tyr Lys Asn Tyr Ile Asp Thr Ile Arg Gln Ile Val Val
        195                 200                 205
```

```
Glu Tyr Ser Asp Ile Arg Thr Leu Leu Val Ile Glu Pro Asp Ser Leu
    210                 215                 220

Ala Asn Leu Val Thr Asn Leu Gly Thr Pro Lys Cys Ala Asn Ala Gln
225                 230                 235                 240

Ser Ala Tyr Leu Glu Cys Ile Asn Tyr Ala Val Thr Gln Leu Asn Leu
                245                 250                 255

Pro Asn Val Ala Met Tyr Leu Asp Ala Gly His Ala Gly Trp Leu Gly
            260                 265                 270

Trp Pro Ala Asn Gln Asp Pro Ala Gln Leu Phe Ala Asn Val Tyr
        275                 280                 285

Lys Asn Ala Ser Ser Pro Arg Ala Leu Arg Gly Leu Ala Thr Asn Val
    290                 295                 300

Ala Asn Tyr Asn Ala Trp Ser Ile Ala Ser Pro Pro Tyr Thr Ser
305                 310                 315                 320

Pro Asn Pro Asn Tyr Asp Glu Lys His Tyr Ile Glu Ala Phe Ala Pro
                325                 330                 335

Leu Leu Arg Asn Gln Gly Phe Asp Ala Lys Phe Ile Val Asp Thr Gly
            340                 345                 350

Arg Asn Gly Lys Gln Pro Thr Gly Gln Leu Glu Trp Gly His Trp Cys
    355                 360                 365

Asn Val Lys Gly Thr Gly Phe Gly Val Arg Pro Thr Ala Asn Thr Gly
370                 375                 380

His Glu Leu Val Asp Ala Phe Val Trp Val Lys Pro Gly Gly Glu Ser
385                 390                 395                 400

Asp Gly Thr Ser Asp Pro Ser Ala Pro Arg Phe Asp Ser His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu His
        435                 440                 445

His His His His
    450

<210> SEQ ID NO 25
<211> LENGTH: 1362
<212> TYPE: DNA
<213> ORGANISM: Artificial Sequence
<220> FEATURE:
<223> OTHER INFORMATION: Cel6a engineered variant 3C6
<220> FEATURE:
<221> NAME/KEY: CDS
<222> LOCATION: (1)..(1362)

<400> SEQUENCE: 25 gct agc tgc tca agc gtc tgg ggc caa tgt ggt ggc cag aat tgg tcg      48
Ala Ser Cys Ser Ser Val Trp Gly Gln Cys Gly Gly Gln Asn Trp Ser
1               5                   10                  15 ggt ccg acc tgc tgt gct tcc gga agc aca tgc gtc tac ttc aac gac      96
Gly Pro Thr Cys Cys Ala Ser Gly Ser Thr Cys Val Tyr Phe Asn Asp
            20                  25                  30 tat tac tcc cag tgt ctt ccc ggc gct gca agc tca agc tcg tcc acg     144
Tyr Tyr Ser Gln Cys Leu Pro Gly Ala Ala Ser Ser Ser Ser Ser Thr
        35                  40                  45 cgc gcc gcg tcg acg act tct cga gta tcc ccc aca aca tcc cgg tcg     192
Arg Ala Ala Ser Thr Thr Ser Arg Val Ser Pro Thr Thr Ser Arg Ser
    50                  55                  60 agc tcc gcg acg cct cca cct ggt tct act act acc aga gta cct cca     240
Ser Ser Ala Thr Pro Pro Pro Gly Ser Thr Thr Thr Arg Val Pro Pro
```

```
              65                  70                  75                  80
gtc gga tcg gga acc gct acg tat tca ggt aac ccc ttt gaa ggt gtt         288
Val Gly Ser Gly Thr Ala Thr Tyr Ser Gly Asn Pro Phe Glu Gly Val
                85                  90                  95 cag ctg tgg gct aat aac tat tat aga tct gag gta cat aca ctg gcc         336
Gln Leu Trp Ala Asn Asn Tyr Tyr Arg Ser Glu Val His Thr Leu Ala
            100                 105                 110 att ccg caa att aca gac ccc gcg ttg cgt gcc gca gct agt gct gcg         384
Ile Pro Gln Ile Thr Asp Pro Ala Leu Arg Ala Ala Ala Ser Ala Ala
            115                 120                 125 gct gag gtg cca agt ttt ttg tgg ctg gat act ttg gac aaa acc ccc         432
Ala Glu Val Pro Ser Phe Leu Trp Leu Asp Thr Leu Asp Lys Thr Pro
        130                 135                 140 tta atg gaa caa acg ttg gct gat ata cgt act gcg aat aaa aac ggc         480
Leu Met Glu Gln Thr Leu Ala Asp Ile Arg Thr Ala Asn Lys Asn Gly
145                 150                 155                 160 ggc aat tat gct gga caa ttt gtg gtt tat gac ctg ccg gat aga gat         528
Gly Asn Tyr Ala Gly Gln Phe Val Val Tyr Asp Leu Pro Asp Arg Asp
                165                 170                 175 tgt gct gca cta gcg agc aac ggg gag tac agc att gcg gat ggc ggt         576
Cys Ala Ala Leu Ala Ser Asn Gly Glu Tyr Ser Ile Ala Asp Gly Gly
            180                 185                 190 gtc gca aag tac aaa aac tat ata gat act atc agg caa ata gtt gtc         624
Val Ala Lys Tyr Lys Asn Tyr Ile Asp Thr Ile Arg Gln Ile Val Val
            195                 200                 205 gaa tac agt gat att cgt acg ctg ctt gta atc gaa ccc gat tcc tta         672
Glu Tyr Ser Asp Ile Arg Thr Leu Leu Val Ile Glu Pro Asp Ser Leu
        210                 215                 220 gcg aac ttg gtg aca aat cta ggt act ccg aag tgt gcg aac gcg cag         720
Ala Asn Leu Val Thr Asn Leu Gly Thr Pro Lys Cys Ala Asn Ala Gln
225                 230                 235                 240 agt gct tat ctt gag tgc atc aat tat gca gtc acc cag ttg aat ttg         768
Ser Ala Tyr Leu Glu Cys Ile Asn Tyr Ala Val Thr Gln Leu Asn Leu
                245                 250                 255 cca aac gtt gca atg tat ctt gat gct ggt cat gcc ggg tgg ttg ggt         816
Pro Asn Val Ala Met Tyr Leu Asp Ala Gly His Ala Gly Trp Leu Gly
            260                 265                 270 tgg cca gca aat ctg gat ccc gct gcg cag ctg ttt gca aat gtt tac         864
Trp Pro Ala Asn Leu Asp Pro Ala Ala Gln Leu Phe Ala Asn Val Tyr
            275                 280                 285 aaa aat gcc tca agt cct aga gcg ctg agg ggt ctt gca aca aat gtt         912
Lys Asn Ala Ser Ser Pro Arg Ala Leu Arg Gly Leu Ala Thr Asn Val
        290                 295                 300 gct aat tac aac gct tgg tca ata gcg agt ccc cca ccg tac aca agc         960
Ala Asn Tyr Asn Ala Trp Ser Ile Ala Ser Pro Pro Pro Tyr Thr Ser
305                 310                 315                 320 cct aac cca aac tac gat gag aag cat tac ata gaa gca ttt gct cct        1008
Pro Asn Pro Asn Tyr Asp Glu Lys His Tyr Ile Glu Ala Phe Ala Pro
                325                 330                 335 ttg ctt cgt aac caa ggt ttt gat gca aag ttt atc gtc gat acc gga        1056
Leu Leu Arg Asn Gln Gly Phe Asp Ala Lys Phe Ile Val Asp Thr Gly
            340                 345                 350 aga aac ggc aag cag ccg aca ggg cag cta gaa tgg ggg cac tgg tgc        1104
Arg Asn Gly Lys Gln Pro Thr Gly Gln Leu Glu Trp Gly His Trp Cys
            355                 360                 365 aat gtc aag ggt acg ggt ttc ggt gtt aga ccc acg gct aac act ggg        1152
Asn Val Lys Gly Thr Gly Phe Gly Val Arg Pro Thr Ala Asn Thr Gly
        370                 375                 380 cat gag ttg gtt gat gca ttc gtt tgg gta aaa ccc gga gga gag tca        1200
```

```
His Glu Leu Val Asp Ala Phe Val Trp Val Lys Pro Gly Gly Glu Ser
385                 390                 395                 400 gat gga acg agt gat cct tct gct cca agg ttc gat tct cat tgc gca   1248
Asp Gly Thr Ser Asp Pro Ser Ala Pro Arg Phe Asp Ser His Cys Ala
            405                 410                 415 tta cca gat gct ttg cag cca gca cct caa gca gga gct tgg ttc caa   1296
Leu Pro Asp Ala Leu Gln Pro Ala Pro Gln Ala Gly Ala Trp Phe Gln
        420                 425                 430 gct tat ttt gta caa tta ctg act aac gcc aat cct agt ttt cta cat   1344
Ala Tyr Phe Val Gln Leu Leu Thr Asn Ala Asn Pro Ser Phe Leu His
            435                 440                 445 cac cat cac cac cat tag                                            1362
His His His His His
        450

<210> SEQ ID NO 26
<211> LENGTH: 453
<212> TYPE: PRT
<213> ORGANISM: Artificial Sequence
<220> FEATURE:
<223> OTHER INFORMATION: Synthetic Construct

<400> SEQUENCE: 26

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Phe Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Glu Gly Val
                85                  90                  95

Gln Leu Trp Ala Asn Asn Tyr Tyr Arg Ser Glu Val His Thr Leu Ala
            100                 105                 110

Ile Pro Gln Ile Thr Asp Pro Ala Leu Arg Ala Ala Ser Ala Ala
        115                 120                 125

Ala Glu Val Pro Ser Phe Leu Trp Leu Asp Thr Leu Asp Lys Thr Pro
    130                 135                 140

Leu Met Glu Gln Thr Leu Ala Asp Ile Arg Thr Ala Asn Lys Asn Gly
145                 150                 155                 160

Gly Asn Tyr Ala Gly Gln Phe Val Val Tyr Asp Leu Pro Asp Arg Asp
                165                 170                 175

Cys Ala Ala Leu Ala Ser Asn Gly Glu Tyr Ser Ile Ala Asp Gly Gly
            180                 185                 190

Val Ala Lys Tyr Lys Asn Tyr Ile Asp Thr Ile Arg Gln Ile Val Val
        195                 200                 205

Glu Tyr Ser Asp Ile Arg Thr Leu Leu Val Ile Glu Pro Asp Ser Leu
    210                 215                 220

Ala Asn Leu Val Thr Asn Leu Gly Thr Pro Lys Cys Ala Asn Ala Gln
225                 230                 235                 240

Ser Ala Tyr Leu Glu Cys Ile Asn Tyr Ala Val Thr Gln Leu Asn Leu
                245                 250                 255

Pro Asn Val Ala Met Tyr Leu Asp Ala Gly His Ala Gly Trp Leu Gly
            260                 265                 270
```

-continued

```
Trp Pro Ala Asn Leu Asp Pro Ala Gln Leu Phe Ala Asn Val Tyr
        275                 280                 285
Lys Asn Ala Ser Ser Pro Arg Ala Leu Arg Gly Leu Ala Thr Asn Val
290                 295                 300
Ala Asn Tyr Asn Ala Trp Ser Ile Ala Ser Pro Pro Tyr Thr Ser
305                 310                 315                 320
Pro Asn Pro Asn Tyr Asp Glu Lys His Tyr Ile Glu Ala Phe Ala Pro
                    325                 330                 335
Leu Leu Arg Asn Gln Gly Phe Asp Ala Lys Phe Ile Val Asp Thr Gly
                340                 345                 350
Arg Asn Gly Lys Gln Pro Thr Gly Gln Leu Glu Trp Gly His Trp Cys
            355                 360                 365
Asn Val Lys Gly Thr Gly Phe Gly Val Arg Pro Thr Ala Asn Thr Gly
        370                 375                 380
His Glu Leu Val Asp Ala Phe Val Trp Val Lys Pro Gly Gly Glu Ser
385                 390                 395                 400
Asp Gly Thr Ser Asp Pro Ser Ala Pro Arg Phe Asp Ser His Cys Ala
                    405                 410                 415
Leu Pro Asp Ala Leu Gln Pro Ala Pro Gln Ala Gly Ala Trp Phe Gln
                420                 425                 430
Ala Tyr Phe Val Gln Leu Leu Thr Asn Ala Asn Pro Ser Phe Leu His
            435                 440                 445
His His His His His
        450

<210> SEQ ID NO 27
<211> LENGTH: 1362
<212> TYPE: DNA
<213> ORGANISM: Artificial Sequence
<220> FEATURE:
<223> OTHER INFORMATION: Cel6a engineered variant 3C6P
<220> FEATURE:
<221> NAME/KEY: CDS
<222> LOCATION: (1)..(1362)

<400> SEQUENCE: 27 gct agc tgc tca agc gtc tgg ggc caa tgt ggt ggc cag aat tgg tcg      48
Ala Ser Cys Ser Ser Val Trp Gly Gln Cys Gly Gly Gln Asn Trp Ser
1               5                   10                  15 ggt ccg acc tgc tgt gct tcc gga agc aca tgc gtc tac ttc aac gac      96
Gly Pro Thr Cys Cys Ala Ser Gly Ser Thr Cys Val Tyr Phe Asn Asp
                20                  25                  30 tat tac tcc cag tgt ctt ccc ggc gct gca agc tca agc tcg tcc acg     144
Tyr Tyr Ser Gln Cys Leu Pro Gly Ala Ala Ser Ser Ser Ser Ser Thr
            35                  40                  45 cgc gcc gcg tcg acg act tct cga gta tcc ccc aca aca tcc cgg tcg     192
Arg Ala Ala Ser Thr Thr Ser Arg Val Ser Pro Thr Thr Ser Arg Ser
        50                  55                  60 agc tcc gcg acg cct cca cct ggt tct act act acc aga gta cct cca     240
Ser Ser Ala Thr Pro Pro Pro Gly Ser Thr Thr Thr Arg Val Pro Pro
65                  70                  75                  80 gtc gga tcg gga acc gct acg tat tca ggt aac ccc ttt gaa ggt gtt     288
Val Gly Ser Gly Thr Ala Thr Tyr Ser Gly Asn Pro Phe Glu Gly Val
                85                  90                  95 cag ctg tgg gct aat aac tat tat aga tct gag gta cat aca ctg gcc     336
Gln Leu Trp Ala Asn Asn Tyr Tyr Arg Ser Glu Val His Thr Leu Ala
                100                 105                 110 att ccg caa att aca gac ccc gcg ttg cgt gcc gca gct agt gct gcg     384
```

```
Ile Pro Gln Ile Thr Asp Pro Ala Leu Arg Ala Ala Ser Ala Ala
            115                 120                 125 gct gag gtg cca agt ttt ttg tgg ctg gat act ttg gac aaa acc ccc     432
Ala Glu Val Pro Ser Phe Leu Trp Leu Asp Thr Leu Asp Lys Thr Pro
130                 135                 140 tta atg gaa caa acg ttg gct gat ata cgt act gcg aat aaa aac ggc     480
Leu Met Glu Gln Thr Leu Ala Asp Ile Arg Thr Ala Asn Lys Asn Gly
145                 150                 155                 160 ggc aat tat gct gga caa ttt gtg gtt tat gac ctg ccg gat aga gat     528
Gly Asn Tyr Ala Gly Gln Phe Val Val Tyr Asp Leu Pro Asp Arg Asp
            165                 170                 175 tgt gct gca cta gcg agc aac ggg gag tac agc att gcg gat ggc ggt     576
Cys Ala Ala Leu Ala Ser Asn Gly Glu Tyr Ser Ile Ala Asp Gly Gly
            180                 185                 190 gtc gca aag tac aaa aac tat ata gat act atc agg caa ata gtt gtc     624
Val Ala Lys Tyr Lys Asn Tyr Ile Asp Thr Ile Arg Gln Ile Val Val
            195                 200                 205 gaa tac agt gat att cgt acg ctg ctt gta atc gaa ccc gat tcc tta     672
Glu Tyr Ser Asp Ile Arg Thr Leu Leu Val Ile Glu Pro Asp Ser Leu
210                 215                 220 gcg aac ttg gtg aca aat cta ggt act ccg aag tgt gcg aac gcg cag     720
Ala Asn Leu Val Thr Asn Leu Gly Thr Pro Lys Cys Ala Asn Ala Gln
225                 230                 235                 240 agt gct tat ctt gag tgc atc aat tat gca gtc acc cag ttg aat ttg     768
Ser Ala Tyr Leu Glu Cys Ile Asn Tyr Ala Val Thr Gln Leu Asn Leu
            245                 250                 255 cca aac gtt gca atg tat ctt gat gct ggt cat gcc ggg tgg ttg ggt     816
Pro Asn Val Ala Met Tyr Leu Asp Ala Gly His Ala Gly Trp Leu Gly
            260                 265                 270 tgg cca gca aat ctg gat ccc gct gcg cag ctg ttt gca aat gtt tac     864
Trp Pro Ala Asn Leu Asp Pro Ala Ala Gln Leu Phe Ala Asn Val Tyr
            275                 280                 285 aaa aat gcc tca agt cct aga gcg ctg agg ggt ctt gca aca aat gtt     912
Lys Asn Ala Ser Ser Pro Arg Ala Leu Arg Gly Leu Ala Thr Asn Val
290                 295                 300 gct aat tac aac gct tgg tca ata gcg agt ccc cca ccg tac aca agc     960
Ala Asn Tyr Asn Ala Trp Ser Ile Ala Ser Pro Pro Pro Tyr Thr Ser
305                 310                 315                 320 cct aac cca aac tac gat gag aag cat tac ata gaa gca ttt gct cct    1008
Pro Asn Pro Asn Tyr Asp Glu Lys His Tyr Ile Glu Ala Phe Ala Pro
            325                 330                 335 ttg ctt cgt aac caa ggt ttt gat gca aag ttt atc gtc gat acc gga    1056
Leu Leu Arg Asn Gln Gly Phe Asp Ala Lys Phe Ile Val Asp Thr Gly
            340                 345                 350 aga aac ggc aag cag ccg aca ggg cag cta gaa tgg ggg cac tgg tgc    1104
Arg Asn Gly Lys Gln Pro Thr Gly Gln Leu Glu Trp Gly His Trp Cys
            355                 360                 365 aat gtc aag ggt acg ggt ttc ggt gtt aga ccc acg gct aac act ggg    1152
Asn Val Lys Gly Thr Gly Phe Gly Val Arg Pro Thr Ala Asn Thr Gly
370                 375                 380 cat gag ttg gtt gat gca ttc gtt tgg gta aaa ccc gga gga gag tca    1200
His Glu Leu Val Asp Ala Phe Val Trp Val Lys Pro Gly Gly Glu Ser
385                 390                 395                 400 gat gga acg agt gat cct tct gct cca agg ttc gat cct cat tgc gca    1248
Asp Gly Thr Ser Asp Pro Ser Ala Pro Arg Phe Asp Pro His Cys Ala
            405                 410                 415 tta cca gat gct ttg cag cca gca cct caa gca gga gct tgg ttc caa    1296
Leu Pro Asp Ala Leu Gln Pro Ala Pro Gln Ala Gly Ala Trp Phe Gln
            420                 425                 430
```

```
gct tat ttt gta caa tta ctg act aac gcc aat cct agt ttt cta cat    1344
Ala Tyr Phe Val Gln Leu Leu Thr Asn Ala Asn Pro Ser Phe Leu His
    435                 440                 445 cac cat cac cac cat tag                                            1362
His His His His His
450
```

<210> SEQ ID NO 28
<211> LENGTH: 453
<212> TYPE: PRT
<213> ORGANISM: Artificial Sequence
<220> FEATURE:
<223> OTHER INFORMATION: Synthetic Construct

<400> SEQUENCE: 28

```
Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Phe Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Glu Gly Val
                85                  90                  95

Gln Leu Trp Ala Asn Asn Tyr Tyr Arg Ser Glu Val His Thr Leu Ala
            100                 105                 110

Ile Pro Gln Ile Thr Asp Pro Ala Leu Arg Ala Ala Ala Ser Ala Ala
        115                 120                 125

Ala Glu Val Pro Ser Phe Leu Trp Leu Asp Thr Leu Asp Lys Thr Pro
    130                 135                 140

Leu Met Glu Gln Thr Leu Ala Asp Ile Arg Thr Ala Asn Lys Asn Gly
145                 150                 155                 160

Gly Asn Tyr Ala Gly Gln Phe Val Val Tyr Asp Leu Pro Asp Arg Asp
                165                 170                 175

Cys Ala Ala Leu Ala Ser Asn Gly Glu Tyr Ser Ile Ala Asp Gly Gly
            180                 185                 190

Val Ala Lys Tyr Lys Asn Tyr Ile Asp Thr Ile Arg Gln Ile Val Val
        195                 200                 205

Glu Tyr Ser Asp Ile Arg Thr Leu Leu Val Ile Glu Pro Asp Ser Leu
    210                 215                 220

Ala Asn Leu Val Thr Asn Leu Gly Thr Pro Lys Cys Ala Asn Ala Gln
225                 230                 235                 240

Ser Ala Tyr Leu Glu Cys Ile Asn Tyr Ala Val Thr Gln Leu Asn Leu
                245                 250                 255

Pro Asn Val Ala Met Tyr Leu Asp Ala Gly His Ala Gly Trp Leu Gly
            260                 265                 270

Trp Pro Ala Asn Leu Asp Pro Ala Ala Gln Leu Phe Ala Asn Val Tyr
        275                 280                 285

Lys Asn Ala Ser Ser Pro Arg Ala Leu Arg Gly Leu Ala Thr Asn Val
    290                 295                 300

Ala Asn Tyr Asn Ala Trp Ser Ile Ala Ser Pro Pro Tyr Thr Ser Pro
305                 310                 315                 320

Pro Asn Pro Asn Tyr Asp Glu Lys His Tyr Ile Glu Ala Phe Ala Pro
```

```
              325                 330                 335
Leu Leu Arg Asn Gln Gly Phe Asp Ala Lys Phe Ile Val Asp Thr Gly
        340                 345                 350

Arg Asn Gly Lys Gln Pro Thr Gly Gln Leu Glu Trp Gly His Trp Cys
        355                 360                 365

Asn Val Lys Gly Thr Gly Phe Gly Val Arg Pro Thr Ala Asn Thr Gly
    370                 375                 380

His Glu Leu Val Asp Ala Phe Val Trp Val Lys Pro Gly Gly Glu Ser
385                 390                 395                 400

Asp Gly Thr Ser Asp Pro Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu His
            435                 440                 445

His His His His His
        450

<210> SEQ ID NO 29
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 29
cgggttattg tttataaata ctactattgc cag                             33

<210> SEQ ID NO 30
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 30
gacatgggag atcgaattca actcc                                      25

<210> SEQ ID NO 31
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 31
gcacatgcgt ctacttcaac gactattact cc                              32

<210> SEQ ID NO 32
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 32
ggagtaatag tcgttgaagt agacgcatgt gc                              32

<210> SEQ ID NO 33
<211> LENGTH: 32
<212> TYPE: DNA
<213> ORGANISM: Artificial Sequence
```

```
<220> FEATURE:
<223> OTHER INFORMATION: Oligonucleotide Primer

<400> SEQUENCE: 33
gcacatgcgt ctactccaac gactattact cc                                32

<210> SEQ ID NO 34
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 34
ggagtaatag tcgttggagt agacgcatgt gc                                32

<210> SEQ ID NO 35
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 35
gcagctagtg ctgcggctga ggtgccaagt tttatgtggc tggatac                47

<210> SEQ ID NO 36
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 36
gtatccagcc acataaaact tggcacctca gccgcagcac tagctgc                47

<210> SEQ ID NO 37
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 37
gcagctagtg ctgtggctga ggagccaagt tttatgtggc tggatac                47

<210> SEQ ID NO 38
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 38
gtatccagcc acataaaact tggctcctca gccacagcac tagctgc                47

<210> SEQ ID NO 39
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 39
gcagctagtg ctgtggctga ggtgccaagt ttttgtggc tggatac                 47
```

<210> SEQ ID NO 40
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 40
gtatccagcc acaaaaaact tggcacctca gccacagcac tagctgc        47

<210> SEQ ID NO 41
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 41
gcagctagtg ctgcggctga ggagccaagt tttatgtggc tggatac        47

<210> SEQ ID NO 42
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 42
gtatccagcc acataaaact tggctcctca gccgcagcac tagctgc        47

<210> SEQ ID NO 43
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 43
gcagctagtg ctgcggctga ggtgccaagt tttttgtggc tggatac        47

<210> SEQ ID NO 44
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 44
gtatccagcc acaaaaaact tggcacctca gccgcagcac tagctgc        47

<210> SEQ ID NO 45
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 45
gcagctagtg ctgtggctga ggagccaagt tttttgtggc tggatac        47

<210> SEQ ID NO 46
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 46
gtatccagcc acaaaaaact tggctcctca gccacagcac tagctgc       47

<210> SEQ ID NO 47
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 47
gcagctagtg ctgcggctga ggagccaagt tttttgtggc tggatac       47

<210> SEQ ID NO 48
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 48
gtatccagcc acaaaaaact tggctcctca gccgcagcac tagctgc       47

<210> SEQ ID NO 49
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 49
gcagctagtg ctgtggctga ggtgccaagt tttatgtggc tggatac       47

<210> SEQ ID NO 50
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 50
gtatccagcc acataaaact tggcacctca gccacagcac tagctgc       47

<210> SEQ ID NO 51
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 51
caaaaatgcc tcaagaccta gagcgctg       28

<210> SEQ ID NO 52
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 52
cagcgctcta ggtcttgagg cattttg       28

<210> SEQ ID NO 53

```
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 53
caaaaatgcc tcaagtccta gagcgctg                                          28

<210> SEQ ID NO 54
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 54
cagcgctcta ggacttgagg cattttg                                           28

<210> SEQ ID NO 55
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 55
gatggaacga gtgatccttc tgctccaag                                         29

<210> SEQ ID NO 56
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 56
cttggagcag aaggatcact cgttccatc                                         29

<210> SEQ ID NO 57
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 57
gatggaacga gtgattcttc tgctccaag                                         29

<210> SEQ ID NO 58
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 58
cttggagcag aagaatcact cgttccatc                                         29

<210> SEQ ID NO 59
<211> LENGTH: 35
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
```

```
<222> LOCATION: (19)..(20)
<223> OTHER INFORMATION: n is a, c, g, or t

<400> SEQUENCE: 59
ggccaatgtg gtggccagnn ktggtcgggt ccgac                              35

<210> SEQ ID NO 60
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 60
ctggccacca cattggcc                                                 18

<210> SEQ ID NO 61
<211> LENGTH: 43
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (21)..(22)
<223> OTHER INFORMATION: n is a, c, g, or t

<400> SEQUENCE: 61
ccggaagcac atgcgtctac nnkaacgact attactccca gtg                     43

<210> SEQ ID NO 62
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 62
gtagacgcat gtgcttccgg                                               20

<210> SEQ ID NO 63
<211> LENGTH: 35
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (19)..(20)
<223> OTHER INFORMATION: n is a, c, g, or t

<400> SEQUENCE: 63
cgtgccgcag ctagtgctnn kgctgaggtg ccaag                              35

<210> SEQ ID NO 64
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 64
agcactagct gcggcacg                                                 18

<210> SEQ ID NO 65
<211> LENGTH: 42
<212> TYPE: DNA
```

```
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (22)..(23)
<223> OTHER INFORMATION: n is a, c, g, or t

<400> SEQUENCE: 65
gcagctagtg ctgtggctga gnnkccaagt tttatgtggc tg            42

<210> SEQ ID NO 66
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 66
ctcagccaca gcactagctg c                                    21

<210> SEQ ID NO 67
<211> LENGTH: 40
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (22)..(23)
<223> OTHER INFORMATION: n is a, c, g, or t

<400> SEQUENCE: 67
gtggctgagg tgccaagttt tnnktggctg gatactttgg               40

<210> SEQ ID NO 68
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 68
aaaacttggc acctcagcca c                                    21

<210> SEQ ID NO 69
<211> LENGTH: 37
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (20)..(21)
<223> OTHER INFORMATION: n is a, c, g, or t

<400> SEQUENCE: 69
gttgggttgg ccagcaaatn nkgatcccgc tgcgcag                   37

<210> SEQ ID NO 70
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 70
atttgctggc caacccaac                                       19
```

<210> SEQ ID NO 71
<211> LENGTH: 42
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (25)..(26)
<223> OTHER INFORMATION: n is a, c, g, or t

<400> SEQUENCE: 71
gcaaatgttt acaaaaatgc ctcannkcct agagcgctga gg         42

<210> SEQ ID NO 72
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 72
tgaggcattt ttgtaaacat ttgc         24

<210> SEQ ID NO 73
<211> LENGTH: 43
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (24)..(25)
<223> OTHER INFORMATION: n is a, c, g, or t

<400> SEQUENCE: 73
cttggtcaat agcgagtcct ccannktaca caagccctaa ccc         43

<210> SEQ ID NO 74
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 74
ggaggactcg ctattgacca ag         22

<210> SEQ ID NO 75
<211> LENGTH: 43
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (25)..(26)
<223> OTHER INFORMATION: n is a, c, g, or t

<400> SEQUENCE: 75
ggagagtcag atggaacgag tgatnnktct gctccaaggt tcg         43

<210> SEQ ID NO 76
<211> LENGTH: 24
<212> TYPE: DNA
<213> ORGANISM: Artificial Sequence
<220> FEATURE:

<223> OTHER INFORMATION: Oligonucleotide Primer

<400> SEQUENCE: 76
atcactcgtt ccatctgact ctcc                                              24

<210> SEQ ID NO 77
<211> LENGTH: 43
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (25)..(26)
<223> OTHER INFORMATION: n is a, c, g, or t

<400> SEQUENCE: 77
gattcttctg ctccaaggtt cgatnnkcat tgcgcattac cag                         43

<210> SEQ ID NO 78
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 78
atcgaacctt ggagcagaag aatc                                              24

<210> SEQ ID NO 79
<211> LENGTH: 46
<212> TYPE: DNA
<213> ORGANISM: Artificial Sequence
<220> FEATURE:
<223> OTHER INFORMATION: Oligonucleotide Primer

<400> SEQUENCE: 79
ctttgaaggt gttcagctgt atgctaataa ctattataga tctgag                      46

<210> SEQ ID NO 80
<211> LENGTH: 46
<212> TYPE: DNA
<213> ORGANISM: Artificial Sequence
<220> FEATURE:
<223> OTHER INFORMATION: Oligonucleotide Primer

<400> SEQUENCE: 80
ctcagatcta atagttat tagcatacag ctgaacacct tcaaag                        46

<210> SEQ ID NO 81
<211> LENGTH: 41
<212> TYPE: DNA
<213> ORGANISM: Artificial Sequence
<220> FEATURE:
<223> OTHER INFORMATION: Oligonucleotide Primer

<400> SEQUENCE: 81
cagctgtggg ctaatccata ttatagatct gaggtacata c                           41

<210> SEQ ID NO 82
<211> LENGTH: 41
<212> TYPE: DNA
<213> ORGANISM: Artificial Sequence
<220> FEATURE:
<223> OTHER INFORMATION: Oligonucleotide Primer

<400> SEQUENCE: 82

```
gtatgtacct cagatctata atatggatta gcccacagct g                         41

<210> SEQ ID NO 83
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 83
gaccccgcgt tggctgccgc agctagtg                                         28

<210> SEQ ID NO 84
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 84
cactagctgc ggcagccaac gcggggtc                                         28

<210> SEQ ID NO 85
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 85
gcgttgcgtg ccaaagctag tgctgcgg                                         28

<210> SEQ ID NO 86
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 86
ccgcagcact agctttggca cgcaacgc                                         28

<210> SEQ ID NO 87
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 87
gacaaaaccc ccttattgga acaaacgttg gc                                    32

<210> SEQ ID NO 88
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 88
gccaacgttt gttccaataa gggggttttg tc                                    32

<210> SEQ ID NO 89
<211> LENGTH: 36
<212> TYPE: DNA
```

```
<213> ORGANISM: Artificial Sequence
<220> FEATURE:
<223> OTHER INFORMATION: Oligonucleotide Primer

<400> SEQUENCE: 89
caaacgttgg ctgatgctcg tactgcgaat aaaaac                              36

<210> SEQ ID NO 90
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 90
gtttttattc gcagtacgag catcagccaa cgtttg                              36

<210> SEQ ID NO 91
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 91
gagcaacggg gagttgagca ttgcggatg                                      29

<210> SEQ ID NO 92
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 92
catccgcaat gctcaactcc ccgttgctc                                      29

<210> SEQ ID NO 93
<211> LENGTH: 38
<212> TYPE: DNA
<213> ORGANISM: Artificial Sequence
<220> FEATURE:
<223> OTHER INFORMATION: Oligonucleotide Primer

<400> SEQUENCE: 93
cagagtgctt atcttgaggg tatcaattat gcagtcac                            38

<210> SEQ ID NO 94
<211> LENGTH: 38
<212> TYPE: DNA
<213> ORGANISM: Artificial Sequence
<220> FEATURE:
<223> OTHER INFORMATION: Oligonucleotide Primer

<400> SEQUENCE: 94
gtgactgcat aattgatacc ctcaagataa gcactctg                            38

<210> SEQ ID NO 95
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 95
gtgcatcaat tatgcattga cccagttgaa tttg                                34
```

<210> SEQ ID NO 96
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 96
caaattcaac tgggtcaatg cataattgat gcac                              34

<210> SEQ ID NO 97
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 97
gtttacaaaa atgccggtag tcctagagcg ctg                               33

<210> SEQ ID NO 98
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 98
cagcgctcta ggactaccgg cattttgta aac                                33

<210> SEQ ID NO 99
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 99
ctcaagtcct agagcggtta ggggtcttgc aac                               33

<210> SEQ ID NO 100
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 100
gttgcaagac ccctaaccgc tctaggactt gag                               33

<210> SEQ ID NO 101
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 101
ccaccgtaca caagctggaa cccaaactac gatg                              34

<210> SEQ ID NO 102
<211> LENGTH: 34
<212> TYPE: DNA
<213> ORGANISM: Artificial Sequence
<220> FEATURE:

<223> OTHER INFORMATION: Oligonucleotide Primer

<400> SEQUENCE: 102
catcgtagtt tgggttccag cttgtgtacg gtgg                              34

<210> SEQ ID NO 103
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 103
gcattacata gaagcattgg ctcctttgct tcg                               33

<210> SEQ ID NO 104
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 104
cgaagcaaag gagccaatgc ttctatgtaa tgc                               33

<210> SEQ ID NO 105
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 105
gaaacggcaa gcagggtaca gggcagctag aatg                              34

<210> SEQ ID NO 106
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 106
cattctagct gccctgtacc ctgcttgccg tttc                              34

<210> SEQ ID NO 107
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 107
caagcagccg acaagacagc tagaatgggg                                   30

<210> SEQ ID NO 108
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 108
ccccattcta gctgtcttgt cggctgcttg                                   30

```
<210> SEQ ID NO 109
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 109
cagccgacag ggagactaga atgggggc                                              28

<210> SEQ ID NO 110
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 110
gcccccattc tagtctccct gtcggctg                                              28

<210> SEQ ID NO 111
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 111
gcaatgtcaa gggtgctggt ttcggtgtta gac                                        33

<210> SEQ ID NO 112
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 112
gtctaacacc gaaaccagca cccttgacat tgc                                        33
```